US012780923B2

(12) United States Patent
Felices et al.

(10) Patent No.: US 12,780,923 B2
(45) Date of Patent: Nov. 3, 2026

(54) B7H3-TARGETING PROTEINS AND METHODS OF USE THEREOF

(71) Applicant: REGENTS OF THE UNIVERSITY OF MINNESOTA, Minneapolis, MN (US)

(72) Inventors: Martin Felices, Circle Pines, MN (US); Jeffrey S. Miller, North Oaks, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 847 days.

(21) Appl. No.: 17/925,574

(22) PCT Filed: Jun. 3, 2021

(86) PCT No.: PCT/US2021/035591

§ 371 (c)(1),
(2) Date: Nov. 15, 2022

(87) PCT Pub. No.: WO2021/247794

PCT Pub. Date: Dec. 9, 2021

(65) Prior Publication Data

US 2023/0203166 A1 Jun. 29, 2023

Related U.S. Application Data

(60) Provisional application No. 63/033,989, filed on Jun. 3, 2020.

(51) Int. Cl.

*C07K 16/28* (2006.01)
*A61P 35/00* (2006.01)
*C07K 14/54* (2006.01)

(52) U.S. Cl.

CPC .......... *C07K 16/2827* (2013.01); *A61P 35/00* (2018.01); *C07K 14/5443* (2013.01); *C07K 16/283* (2013.01); *C07K 2317/31* (2013.01); *C07K 2317/55* (2013.01); *C07K 2317/565* (2013.01); *C07K 2317/622* (2013.01)

(58) Field of Classification Search

CPC ............ C07K 16/2827; C07K 14/5443; C07K 16/283; C07K 2317/31; C07K 14/70503; C07K 2317/569; C07K 2319/33

See application file for complete search history.

(56) References Cited

U.S. PATENT DOCUMENTS

| | | | |
|---|---|---|---|
| 5,234,809 | A | 8/1993 | Boom et al. |
| 7,776,616 | B2 | 8/2010 | Heath et al. |
| 7,957,913 | B2 | 6/2011 | Chinitz et al. |
| 2002/0190663 | A1 | 12/2002 | Rasmussen |
| 2005/0239170 | A1 | 10/2005 | Hedley et al. |
| 2010/0285578 | A1 | 11/2010 | Selden et al. |
| 2016/0207996 | A1 | 7/2016 | Ulrichts et al. |
| 2017/0362322 | A1 | 12/2017 | DuBridge et al. |
| 2018/0282386 | A1 | 10/2018 | Vallera et al. |
| 2019/0010242 | A1* | 1/2019 | Eckelman ............ C07K 16/468 |
| 2019/0127471 | A1* | 5/2019 | Loo .................... C07K 16/2827 |

FOREIGN PATENT DOCUMENTS

| | | | |
|---|---|---|---|
| CN | 108697736 | A | 10/2018 |
| WO | WO 2006/016276 | A2 | 2/2006 |
| WO | WO 2016/044383 | A1 | 3/2016 |
| WO | WO 2017/062604 | A1 | 4/2017 |
| WO | WO 2019/051102 | A2 | 3/2019 |
| WO | WO 2020/081841 | A1 | 4/2020 |
| WO | WO 2022/098925 | A1 | 5/2022 |
| WO | WO 2022/266341 | A1 | 12/2022 |

OTHER PUBLICATIONS

European Patent Application No. 21818473.7, filed Dec. 21, 2022; Partial Supplementary European Search Report issued May 10, 2024; 14 pages.

Behar et al., "Isolation and characterization of anti-FcgammaRIII (CD16) llama single-domain antibodies that activate natural killer cells," 2008. *Protein Eng Des Sel.* 21(1): 1-10).

Geller et al., "Intraperitoneal delivery of human natural killer cells for treatment of ovarian cancer in a mouse xenograft model," 2013. *Cytotherapy* 15(10):1297-1306.

GenBank Sequence EF561291, Lama glama clone C21 immunoglobulin heavy chain variable region mRNA, partial cds,' 2007, 1 page.

PCT Patent Application No. PCT/US2021/035591, filed Jun. 3, 2021, International Search Report and Written Opinion mailed Nov. 26, 2021, 12 pages.

PCT Patent Application No. PCT/US2021/035591, filed Jun. 3, 2021, International Preliminary Report on Patentability, issued Dec. 6, 2022, 7 pages.

Tatusova et al., "Blast 2 Sequences, a new tool for comparing protein and nucleotide sequences," *FEMS Microbial Lett*, 174, 247-250 (1999).

Vallera et al., "IL15 Trispecific Killer Engagers (TriKE) Make Natural Killer Cells Specific to CD33+ Targets While Also Inducing Persistence, In Vivo Expansion, and Enhanced Function," *Clin Cancer Res.* 2016;22(14):3440-50.

(Continued)

*Primary Examiner* — Laura B Goddard
*Assistant Examiner* — Alyssa Rae Stonebraker
(74) *Attorney, Agent, or Firm* — Mueting Raasch Group

(57) ABSTRACT

Multispecific B7H3 targeting compounds and methods of use thereof are provided. The multispecific compounds include bispecific targeting proteins including a B7H3 targeting domain and an immune cell engaging domain; and trispecific targeting proteins including a B7H3 targeting domain, an immune cell engaging domain and an immune cell activating domain. The methods of use include methods of inducing NK-mediates cell killing, methods of inducing NK expansion in vivo, and methods of treating cancer.

23 Claims, 21 Drawing Sheets

Specification includes a Sequence Listing.

(56) References Cited

OTHER PUBLICATIONS

Vincke et al., "General strategy to humanize a camelid single-domain antibody and identification of a universal humanized nanobody scaffold," 2009. *J Biol Chem.* 284(5):3273-3284.
Yang et al., "B7-H3, a checkpoint molecule, as a target for cancer immunotherapy," *Int J Biol Sci* 2020; 25 16(11):1767-1773.
Japanese Office Action mailed Apr. 8, 2025—English language translation included for Japanese Patent Application No. 2022-574532, (22 pages).
Kontos et al, "IL-15/B7-H3 TriKEs-Based Immunotherapy for Pancreatic Ductal Adenocarcinoma" Journal of the American College of Surgeons, 2019; 229(4) Supplement 1, p. S176.
Chinese Office Action mailed Sep. 30, 2025—English language translation included—for Chinese Patent Application No. 202180049778.X, (16 pages).
Manganaro et al., Genbank database Accession No. NP_751915.1 interleukin-15 isoform 2 preproprotein [*Homo sapiens*], 3 pages. Retrieved from the internet on Oct. 22, 2025 at <ncbi.nlm.nih.gov/protein/NP_751915.1>.

* cited by examiner

FIGURE 1B

```
                      1                               CDR1              50
CD276-new-1   (1)    HVQLVESGGGLVQPGRSLRLSCAASGFTFS[SYWMY]WVRQTPGKGLEWVST     SEQ ID NO:1
CD276-new-2   (1)    QVQLVESGGGLVQPGGSLRLSCAASGFTFS[SYWMY]WVRQTPGKGLEWVST     SEQ ID NO:2
  Consensus   (1)     VQLVESGGGLVQPG SLRLSCAASGFTFSSYWMYWVRQTPGKGLEWVST       SEQ ID NO:3

                     51         CDR2                                    100
CD276-new-1   (51)   [INRDGSATWYADSVKGRFT]ISRDNAKNTGYLQMNSLEPDDTAVYYCVS[DP]   SEQ ID NO:1 (cont.)
CD276-new-2   (51)   [INRDGSATWYADSVKGRFT]ISRDNAKNTGYLQMNSLKPDDTAVYYCVS[DP]   SEQ ID NO:2 (cont.)
  Consensus   (51)   INRDGSATWYADSVKGRFTISRDNAKNTGYLQMNSL PDDTAVYYCVSDP       SEQ ID NO:3 (cont.)

                     101     CDR3          122
CD276-new-1   (101)  [DNYSSDEMVPY]WGQGTQVTVSS      SEQ ID NO:1 (cont.)
CD276-new-2   (101)  [DNYSSDEMVPY]WGQGTQVTVSS      SEQ ID NO:2 (cont.)
  Consensus   (101)  DNYSSDEMVPYWGQGTQVTVSS        SEQ ID NO:3 (cont.)
```

B7H3-TARGETING PROTEINS AND METHODS OF USE THEREOF

CROSS-REFERENCE TO RELATED APPLICATIONS

This application is the § 371 U.S. National Stage of International Application No. PCT/US2021/035591, filed Jun. 3, 2021, which claims the benefit of priority under 35 U.S.C. § 119(e) of U.S. Provisional Application No. 63/033,989, filed Jun. 3, 2020, each of which is incorporated by reference herein in its entirety.

SEQUENCE LISTING

This application contains a Sequence Listing electronically submitted via EFS-Web to the United States Patent and Trademark Office as an ASCII text file entitled "0110-000661WO01_ST25.txt" having a size of 40 kilobytes and created on Jun. 2, 2021. The information contained in the Sequence Listing is incorporated by reference herein.

SUMMARY

In one aspect, this disclosure describes an anti-B7H3 protein that includes at least one of SEQ ID NO:4, SEQ ID NO:5, or SEQ ID NO:6, or a functional variant thereof.

In another aspect, this disclosure describes an anti-B7H3 protein that includes SEQ ID NO:1, SEQ ID NO:2, SEQ ID NO:3 a CDR region of SEQ ID NO:1, a CDR region of SEQ ID NO:2, a CDR region of SEQ ID NO:3, or a functional variant thereof.

In another aspect, this disclosure describes a multispecific compound. Generally, the multispecific compound includes a targeting domain and an immune cell engaging domain operably linked to the targeting domain. The targeting domain includes an anti-B7H3 protein.

In some embodiments, the immune cell is a T cell or a Natural Killer (NK) cell. In embodiments in which the immune cell is an NK cell, the immune cell engaging domain can include a ligand or antibody that specifically binds to CD16. In embodiments in which the immune cell engaging domain includes an antibody that specifically binds to CD16, the antibody can be an scFv, a $F(ab)_2$, a Fab, or a single domain antibody (sdAb).

In some embodiments, the immune cell engaging domain can include SEQ ID NO:19. In some embodiments, the targeting domain can include SEQ ID NO:1, SEQ ID NO:2, or SEQ ID NO:3. In some embodiments, the immune cell engaging domain can include SEQ ID NO:19 and the targeting domain can include SEQ ID NO:1, SEQ ID NO:2, or SEQ ID NO:3.

In some embodiments, the immune cell engaging domain and the targeting domain are linked by a linker having the amino acid sequence of any one of SEQ ID NOs: 12-18. In some of these embodiments, the immune cell engaging domain and the targeting domain are linked by a linker having the amino acid sequence of SEQ ID NO:14.

In some embodiments, the anti-B7H3 multispecific compound includes amino acids 19-294 of SEQ ID NO:20 or amino acids 19-284 of SEQ ID NO:21.

In some embodiments, the anti-B7H3 multispecific compound can be a trispecific compound that further include an immune cell activating domain. In embodiments in which the immune cell is an NK cell, the immune cell activating domain includes a cytokine or a functional portion thereof. In some of these embodiments, the cytokine is IL-15, or a functional variant thereof.

In some embodiments, the trispecific compound can include the amino acids of SEQ ID NO:19 as the immune cell engaging domain, the amino acids of SEQ ID NO:19 as the immune cell activating domain, and the amino acids of any one of SEQ ID NOs:1-3 as the targeting domain. The functional domains may be linked by any one or combination of two or more linkers reflected in SEQ ID NOs: 12-18. In some of these embodiments, the immune cell engaging domain may be linked to the immune cell activating domain by a linker having the amino acid sequence of SEQ ID NO:14. In some embodiments, the immune cell activating domain and the targeting domain may be linked by a linker having the amino acid sequence of SEQ ID NO:15.

In some embodiments, the anti-B7H3 trispecific compound can include the amino acid sequence of SEQ ID NO:22 or SEQ ID NO:23.

In some embodiments, the functional variant of IL-15 includes an N72D or N72A amino acid substitution compared to SEQ ID NO:11.

In another aspect, this disclosure describes an isolated nucleic acid sequence encoding any embodiment of the anti-B7H3 multispecific compound described herein.

In another aspect, this disclosure describes a host cell that includes any embodiment of the isolated nucleic acid summarized above. In some embodiments, the host cell is a T cell, an NK cell, or a macrophage.

In another aspect, this disclosure describes a pharmaceutical composition that includes an anti-B7H3 multispecific compound and a pharmaceutically acceptable carrier.

In another aspect, this disclosure describes a method that generally includes administering to a subject an anti-B7H3 multispecific compound in an amount effective to induce natural killer (NK)-mediated killing of a cell. The anti-B7H3 multispecific compound includes a targeting domain that includes the anti-B7H3 protein, and an NK engaging domain operably linked to the targeting domain.

In another aspect, this disclosure describes a method for stimulating expansion of natural killer (NK) cells in vivo. Generally, the method includes administering to a subject an effective amount of an anti-B7H3 multispecific compound. The anti-B7H3 multispecific compound includes a targeting domain that includes the anti-B7H3 protein, and an NK engaging domain operably linked to the targeting domain.

In another aspect, this disclosure describes a method of treating a subject having, or at risk of having cancer. Generally, the method includes administering to a subject an effective amount of an anti-B7H3 multispecific compound. The anti-B7H3 multispecific compound includes a targeting domain that includes the anti-B7H3 polypeptide, and an NK engaging domain operably linked to the targeting domain. In some embodiments, the cancer cells express B7H3.

In another aspect, this disclosure describes a chimeric antigen receptor compound that includes an anti-B7H3 polypeptide.

In another aspect, this disclosure describes a targeted therapeutic compound that includes a targeting domain and a therapeutic domain linked to the targeting domain. The targeting domain includes an anti-B7H3 polypeptide. In some embodiments, the targeted therapeutic provides targeted immunotherapy. In some embodiments, the therapeutic domain includes a drug, a therapeutic radioisotope, a toxin, a cytokine, or a chemokine.

In another aspect, this disclosure describes a targeted imaging compound that includes a targeting domain and an imaging domain linked to the targeting domain. The targeting domain includes an anti-B7H3 polypeptide. In some embodiments, the imagining domain includes a colorimetric label, a fluorescent label, a radioactive label, a magnetic label, or an enzymatic label.

In another aspect, this disclosure describes a capture assay device that includes an anti-B7H3 polypeptide immobilized to a substrate.

BRIEF DESCRIPTION OF THE DRAWINGS

FIGS. 1A-1B illustrate schematic of trispecific killer engager incorporating exemplary embodiments of anti-B7H3 protein. FIG. 1A illustrates a schematic of an exemplary anti-B7H3 protein sequence (e.g., a sdAb) incorporated into the trispecific killer engager backbone, which also includes recombinant human IL-15 and an anti-CD16 single domain antibody (sdAb) arm, all connected through short linkers. FIG. 1B illustrates the amino acid sequences for the novel anti-B7H3 proteins.

FIG. 2A is a graph bar illustrating NK cell degranulation (% CD107a+) when trispecific killer engagers (30 nM) were incubated with peripheral blood mononuclear cells (PBMCs) alone. FIG. 2B is a graph bar illustrating NK cell degranulation when trispecific killer engagers (30 nM) were co-cultured with PBMCs and prostate cancer cells (PC3). FIG. 2C is a graph bar illustrating NK cell degranulation when trispecific killer engagers (30 nM) were co-cultured with PBMCs and prostate cancer cells (DU145). FIG. 2D is a graph bar illustrating IFN-7 production when trispecific killer engagers (30 nM) were incubated with PBMCs alone. FIG. 2E is a graph bar illustrating IFN-γ production when trispecific killer engagers (30 nM) were co-cultured with PBMCs and PC3 cells. FIG. 2F is a graph bar illustrating IFN-γ production when trispecific killer engagers (30 nM) were co-cultured with PBMCs and DU145 cells.

FIG. 3A is a graph bar illustrating NK cell degranulation (% CD107a+) when trispecific killer engagers (30 nM) were co-cultured with PBMCs and prostate cancer cells (LnCAP). FIG. 3B is a graph bar illustrating NK cell degranulation when trispecific killer engagers (30 nM) were co-cultured with PBMCs and prostate cancer cells (C4-2). FIG. 3C is a graph bar illustrating IFN-γ production when trispecific killer engagers (30 nM) were co-cultured with PBMCs and LnCAP cells. FIG. 3D is a graph bar illustrating IFN-γ production when trispecific killer engagers (30 nM) were co-cultured with PBMCs and C4-2 cells.

FIG. 4A is a graph bar illustrating NK cell degranulation when trispecific killer engagers (30 nM) were incubated with PBMCs alone. FIG. 4B is a graph bar illustrating NK cell degranulation when trispecific killer engagers (30 nM) were co-cultured with PBMCs and C4-2 cells. FIG. 4C is a graph bar illustrating NK cell degranulation when trispecific killer engagers (30 nM) were co-cultured with PBMCs and lung cancer cells (A549). FIG. 4D is a graph bar illustrating IFN-γ production when trispecific killer engagers (30 nM) were incubated with PBMCs alone. FIG. 4E is a graph bar illustrating IFN-γ production when trispecific killer engagers (30 nM) were co-cultured with PBMCs and C4-2 cells. FIG. 4F is a graph bar illustrating IFN-γ production when trispecific killer engagers (30 nM) were co-cultured with PBMCs and A549 cells.

FIG. 5A is a graph bar illustrating NK cell degranulation when trispecific killer engagers (30 nM) were co-cultured with PBMCs and lung cancer cells (NCI-H460s). FIG. 5B is a graph bar illustrating NK cell degranulation when trispecific killer engagers (30 nM) were co-cultured with PBMCs and ovarian cancer cells (OVCAR8). FIG. 5C is a graph bar illustrating NK cell degranulation when trispecific killer engagers (30 nM) were co-cultured with PBMCs and ovarian cancer cells (MA148). FIG. 5D is a graph bar illustrating IFN-γ production when trispecific killer engagers (30 nM) were co-cultured with PBMCs and NCI-H460s cells. FIG. 5E is a graph bar illustrating IFN-γ production when trispecific killer engagers (30 nM) were co-cultured with PBMCs and OVCAR8 cells. FIG. 5F is a graph bar illustrating IFN-γ production when trispecific killer engagers (30 nM) were co-cultured with PBMCs and MA148 cells.

FIG. 6A is a graph bar illustrating NK cell degranulation when trispecific killer engagers (0.3 nM) were incubated with PBMCs alone. FIG. 6B is a graph bar illustrating NK cell degranulation when trispecific killer engagers (3 nM) were incubated with PBMCs alone. FIG. 6C is a graph bar illustrating NK cell degranulation when trispecific killer engagers (30 nM) were incubated with PBMCs alone. FIG. 6D is a graph bar illustrating NK cell degranulation when trispecific killer engagers (0.3 nM) were co-cultured with PBMCs and C4-2 cells. FIG. 6E is a graph bar illustrating NK cell degranulation when trispecific killer engagers (3 nM) were co-cultured with PBMCs and C4-2 cells. FIG. 6F is a graph bar illustrating NK cell degranulation when trispecific killer engagers (30 nM) were co-cultured with PBMCs and C4-2 cells.

FIG. 7A is a graph bar illustrating IFN-γ production when trispecific killer engagers (0.3 nM) were incubated with PBMCs alone. FIG. 7B is a graph bar illustrating IFN-γ production when trispecific killer engagers (3 nM) were incubated with PBMCs alone. FIG. 7C is a graph bar illustrating IFN-γ production when trispecific killer engagers (30 nM) were incubated with PBMCs alone. FIG. 7D is a graph bar illustrating IFN-γ production when trispecific killer engagers (0.3 nM) were co-cultured with PBMCs and C4-2 cells. FIG. 7E is a graph bar illustrating IFN-γ production when trispecific killer engagers (3 nM) were co-cultured with PBMCs and C4-2 cells. FIG. 7F is a graph bar illustrating IFN-γ production when trispecific killer engagers (30 nM) were co-cultured with PBMCs and C4-2 cells.

DETAILED DESCRIPTION OF ILLUSTRATIVE EMBODIMENTS

Figure 1A:
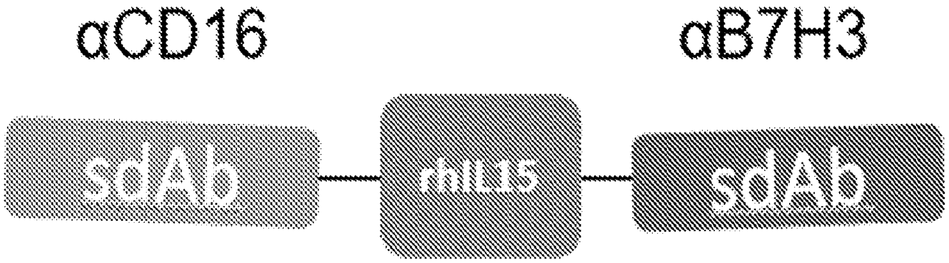

This disclosure describes anti-B7H3 polypeptides, compounds and devices that include anti-B7H3 polypeptides, and methods of suing such compounds and devices. Exemplary platforms in which an anti-B7H3 polypeptide may be used include, but are not limited to, chimeric antigen receptor therapies (e.g., CAR-NK therapy, CAR-T therapy, CAR-macrophage therapy, etc.), multispecific immune cell engager technologies (e.g., bispecific killer engagers, trispecific killer engagers, bispecific T cell engagers, trispecific T cell engagers, etc.), targeted immunotherapies (e.g., targeted ADAM17 blocker (TAB) therapy), delivery of therapeutics (e.g., delivery of antibody-drug conjugates, delivery of therapeutic radioisotopes, delivery of toxins, delivery of cytokines, delivery of chemokines), imaging technologies (delivery of labeling constructs and/or labeling radioisotopes), cell and/or ligand capture technologies (e.g., ELISA, etc.)

B7 Homolog 3 (B7H3), also known as cluster of differentiation 276 (CD276), is a human protein encoded by the CD276 gene. The B7H3 protein is a 316 amino acid-long type I transmembrane protein existing in two isoforms determined by its extracellular domain. In mice, the extracellular domain consists of a single pair of immunoglobulin variable (IgV)-like and immunoglobulin constant (IgC)-like domains, whereas in humans it consists of one pair (2Ig-B7H3) or two identical pairs (4Ig-B7H3) due to exon duplication. B7H3 mRNA is expressed in most normal tissues. In contrast, B7H3 protein has a very limited expression on normal tissues because of its post-transcriptional regulation by microRNAs. In normal tissues, B7H3 has a predominantly inhibitory role in adaptive immunity, suppressing T cell activation and proliferation.

B7H3 is overexpressed among several kinds of human cancer cells. In malignant tissues, B7H3 is an immune checkpoint molecule that inhibits tumor antigen-specific immune responses. B7H3 also possesses non-immunological pro-tumorigenic functions such as promoting migration, invasion, angiogenesis, chemoresistance, epithelial-to-mesenchymal transition, and affecting tumor cell metabolism. B7H3 is recognized as a co-stimulatory molecule for immune reactions including, but not limited to, T cell activation and IFN-γ production. In the presence of anti-CD3 antibody mimicking the TCR signal, human B7H3-Ig fusion protein increases the proliferation of both $CD4^+$ and $CD8^+$ T cells and enhances the cytotoxic T lymphocyte (CTL) activity in vitro. B7H3 also has an antitumor effect on adenocarcinoma of the colon. B7H3 is also expressed in pancreatic cancer and is associated with increased treatment efficacy. Pancreatic cancer patients with high tumor B7H3 levels have a significantly better postoperative prognosis than patients with low tumor B7H3 levels (Yang et al., *Int J Biol Sci* 2020; 16(11):1767-1773). Due to its selective expression on solid tumors and its pro-tumorigenic function, B7H3 is the target of several anti-cancer agents including enoblituzumab, omburtamab, MGD009, MGC018, DS-7300a, and CAR-T cells.

In one aspect, therefore, an anti-B7H3 polypeptide may be incorporated into an immunotherapeutic compound. Immunotherapeutic compounds can provide individualized treatment that activates or suppresses the immune system to amplify or diminish an immune response and is developing rapidly for treating various forms of cancer. Immunotherapy for cancer, such as chimeric antigen receptor (CAR)-T cells, CAR-natural killer (NK) cells, PD-1 and PD-L1 inhibitor, aims to help a subject's immune system fight cancer. The activation of T cells depends on both the specific combination of T cell receptor (TCR) and peptide-bound major histocompatibility complex (MHC), and the interplay of co-stimulatory molecules of T cell with ligands on antigen presenting cells (APCs). The B7 families, peripheral membrane proteins on activated APCs, have been shown to participate in regulation of T cell responses. Recent studies indicate that the upregulation of inhibitory B7 molecules in the cancer microenvironment is highly related to the immune evasion of tumors. As a newly identified member of the B7 family, B7H3 could promote the activation of T cells and the production of IFN-7.

In one embodiment, this disclosure describes an anti-B7H3 polypeptide that includes at least one complementarity-determining region (CDR) as reflected in SEQ ID NO:4, SEQ ID NO:5, and SEQ ID NO:6. Exemplary anti-B7H3 polypeptides that include each of these CDRs is reflected in the amino acid sequences of SEQ ID NO:1, SEQ ID NO:2, and SEQ ID NO:3. As used herein, the terms "peptide," "polypeptide," and "protein" refer interchangeably to any chain of at least two amino acids, linked by a covalent chemical bound. Thus, as used herein, the term "polypeptide" can refer to the complete amino acid sequence coding for an entire protein or to a portion thereof. As used herein, the terms "anti-B7H3 peptide," "anti-B7H3 protein," "B7H3 binding peptide," and "B7H3 targeting peptide" generally refer to any peptide or polypeptide (including a protein or a fusion protein) that can specifically bind to B7H3.

In some embodiments, the anti-B7H3 polypeptide can be an antibody or an antibody fragment that includes a CDR region. As used herein, "CDR region" refers to one or more of the three complementarity-determining regions (CDRs) of SEQ ID NO:1, SEQ ID NO:2, and SEQ ID NO:3. The CDRs are identified separately as SEQ ID NO:4, SEQ ID NO:5, and SEQ ID NO:6. In some aspects, the polypeptide encodes the light chain and the heavy chain of a B7H3 targeting protein.

A "protein coding sequence" or a sequence that "encodes" a particular polypeptide is a nucleic acid sequence that is transcribed (in the case of DNA) and is translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, cDNA from prokaryotic or eukaryotic mRNA, genomic DNA sequences from prokaryotic or eukaryotic DNA, and even synthetic DNA sequences. A transcription termination sequence will usually be located 3' to the coding sequence.

The term "antibody" refers to a molecule that contains at least one antigen binding site that immunospecifically binds to a particular antigen target of interest. The term "antibody" thus includes but is not limited to a full length antibody and/or its variants, a fragment thereof, peptibodies and variants thereof, monoclonal antibodies (including full-length monoclonal antibodies), multispecific antibodies (e.g., bispecific antibodies) formed from at least two intact antibodies, human antibodies, humanized antibodies, and antibody mimetics that mimic the structure and/or function of an antibody or a specified fragment or portion thereof, including single chain antibodies and fragments thereof. Thus, as used herein, the term "antibody" encompasses antibody fragments capable of binding to a biological molecule (such as an antigen or receptor) or a portion thereof, including but not limited to Fab, Fab' and $F(ab')_2$, pFc', Fd, a single domain antibody (sdAb), a variable fragment (Fv), a single-chain variable fragment (scFv) or a disulfide-linked Fv (sdFv); a diabody or a bivalent diabody; a linear antibody; a single-chain antibody molecule; and a multispecific antibody (e.g., a tribody) formed from antibody fragments.

The antibody can be of any type (e.g., IgG, IgE, IgM, IgD, IgA and IgY), class (e.g., IgG1, IgG2, IgG3, IgG4, IgAQ1 and IgA2), or subclass.

The anti-B7H3 protein described herein can be any protein that selectively binds to B7H3. Exemplary anti-B7H3 proteins include SEQ ID NO:1, SEQ ID NO:2, SEQ ID NO:3, and functional variants thereof. As used herein, a protein is a "functional variant" to a reference protein if the amino acid sequence of the protein possesses a specified amount of identity compared to the reference protein and retains the activity of the reference protein. Structural similarity of two proteins can be determined by aligning the residues of the two proteins (for example, a candidate protein and the protein of, for example, SEQ ID NO:1 SEQ ID NO:2, or SEQ ID NO:3) to optimize the number of identical amino acids along the lengths of their sequences; gaps in either or both sequences are permitted in making the alignment in order to optimize the number of identical amino acids, although the amino acids in each sequence must nonetheless remain in their proper order. A candidate protein is the protein being compared to the reference protein (e.g., SEQ ID NO:1, SEQ ID NO:2, or SEQ ID NO:3). A candidate protein can be isolated, for example, from an animal, or can be produced using recombinant techniques, or chemically or enzymatically synthesized.

A pair-wise comparison analysis of amino acid sequences can be carried out using, for example, the BESTFIT algorithm in the GCG package (version 10.2, Madison WI). Alternatively, proteins may be compared using the Blastp program of the BLAST 2 search algorithm, as described by Tatiana et al., (*FEMS Microbiol Lett,* 174, 247-250 (1999)), and available on the National Center for Biotechnology Information (NCBI) website. The default values for all BLAST 2 search parameters may be used, including matrix=BLOSUM62; open gap penalty=11, extension gap penalty=1, gap x_dropoff=50, expect=10, wordsize=3, and filter on.

In the comparison of two amino acid sequences, structural similarity may be referred to by percent "identity" or may be referred to by percent "similarity." "Identity" refers to the presence of identical amino acids. "Similarity" refers to the presence of not only identical amino acids but also the presence of conservative substitutions. A conservative substitution for an amino acid in an anti-B7H3 protein may be selected from other members of the class to which the amino acid belongs. For example, it is well-known in the art of protein biochemistry that an amino acid belonging to a grouping of amino acids having a particular size or characteristic (such as charge, hydrophobicity and hydrophilicity) can be substituted for another amino acid without altering the activity of a protein, particularly in regions of the protein that are not directly associated with biological activity. For example, nonpolar (hydrophobic) amino acids include alanine, leucine, isoleucine, valine, proline, phenylalanine, tryptophan, and tyrosine. Polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Conservative substitutions include, for example, Lys for Arg and vice versa to maintain a positive charge; Glu for Asp and vice versa to maintain a negative charge; Ser for Thr so that a free —OH is maintained; and Gln for Asn to maintain a free —$NH_2$. Likewise, biologically active analogs of a protein containing deletions or additions of one or more contiguous or noncontiguous amino acids that do not eliminate a functional activity of the protein are also contemplated.

Generally, portions of SEQ ID NO:1, SEQ ID NO:2, and SEQ ID NO:3 outside of the CDRs are more amenable to variation while maintaining anti-B7H3 functionality—i.e., specifically bind to B7H3. Thus, an anti-B7H3 protein can include one, two, or all three of the CDRs of SEQ ID NO:1, SEQ ID NO:2, and SEQ ID NO:3 i.e., the amino acids of SEQ ID NO:4 (CDR1), SEQ ID NO:5 (CDR2), and SEQ ID NO:6 (CDR3).

An anti-B7H3 protein as described herein can include a protein with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence similarity to SEQ ID NO:1, SEQ ID NO:2, or SEQ ID NO:3.

An anti-B7H3 protein as described herein can include a protein with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO:1, SEQ ID NO:2, or SEQ ID NO:3.

Variants of the disclosed sequences also include proteins, or full-length protein, that contain substitutions, deletions, or insertions into the protein backbone, that would still leave at least about 70% homology to the original protein over the corresponding portion. A yet greater degree of departure from homology is allowed if like-amino acids, i.e., conservative amino acid substitutions, do not count as a change in the sequence. Examples of conservative substitutions involve amino acids that have the same or similar properties. Illustrative amino acid conservative substitutions include the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; valine to isoleucine to leucine.

In some aspects, an anti-B7H3 protein can include additional sequences, such as, for example, amino acids appended to the C-terminal or N-terminal of the anti-B7H3 protein. Such modifications can, for example, facilitate purification by trapping on columns, the use of antibodies, or facilitate recovery when expressed recombinantly in a microbe. Such tags include, for example, a histidine-rich tag (e.g., SEQ ID NO:8) that allows purification of proteins on nickel columns and/or a leader sequence (e.g., SEQ ID NO:7) that can traffic recombinantly-expressed protein to the membrane of the cell in which it is recombinantly expressed. Such gene modification techniques and suitable additional sequences are well known in the molecular biology arts. In some embodiments, the C-terminal and/or N-terminal modification may be cleaved from the anti-B7H3 protein before being incorporated into, for example, a pharmaceutical composition. In other embodiments, retaining a C-terminal or N-terminal modification may be desired for a given application—i.e., to facilitate immobilization to a substrate.

In another aspect, this disclosure describes a multispecific compound that includes a targeting domain that includes an anti-B7H3 protein. The anti-B7H3 protein includes at least one CDR from SEQ ID NO:1. SEQ ID NO:2, or SEQ ID NO:3 such as, for example, the amino acid sequence of SEQ ID NO:4, SEQ ID NO:5, or SEQ ID NO:6. The multispecific compound further includes an immune cell engaging domain operably linked to the targeting domain.

The terms "multispecific compound" and "multispecific protein" refer to a "fusion molecule" or "fusion protein" and refer to a biologically active polypeptide, including two or more binding domains, with or without a further effector molecule, covalently linked (e.g., fused) by recombinant, chemical, or other suitable method. For example, a binding domain can be linked to another binding domain through a peptide linker sequence. Alternatively, a peptide linker may be used to assist in the construction of the fusion molecule.

As used herein, the term "operably linked" refers to a direct or indirect covalent linking between the domains of the multispecific compound. Thus, two domains that are operably linked may be directly covalently coupled to one another. Conversely, two operably linked domains may be connected by mutual covalent linking to an intervening moiety (e.g., a flanking sequence or linker). Two domains may be considered operably linked if, for example, they are separated by the third domain, with or without one or more intervening flanking sequences.

Domains of a multispecific compound can be in assembled operable linkage with one another using one or more linkers. The term "linker" as used herein refers any bond, small molecule, peptide sequence, or other vehicle that physically links the domains. Linkers can be susceptible to or be substantially resistant to acid-induced cleavage, light-induced cleavage, peptidase-induced cleavage, esterase-induced cleavage and disulfide bond cleavage at conditions under which the compound or the antibody remains active. Linkers are classified upon their chemical motifs, well known in the art, including disulfide groups, hydrazine or peptides (cleavable), or thioester groups (non-cleavable). Linkers also include charged linkers, and hydrophilic forms thereof as known in the art.

Suitable linker for linking domains of a multispecific anti-B7H3 compound can include natural linkers, empirical linkers, or a combination of natural and empirical linkers. Natural linkers are derived from multi-domain proteins, which are naturally present between protein domains. Properties of natural linkers such as, for example, length, hydrophobicity, amino acid residues, and/or secondary structure can be exploited to confer desirable properties to a multi-domain compound that includes natural linkers connecting functional domains.

The studies of linkers in natural multi-domain proteins have led to the generation of many empirical linkers with various sequences and conformations for the construction of recombinant fusion proteins. Empirical linkers can be classified in three types: flexible linkers, rigid linkers, and cleavable linkers. Flexible linkers can provide a certain degree of movement or interaction at the joined domains. Flexible linkers typically include small, non-polar (e.g., Gly) or polar (e.g., Ser or Thr) amino acids, which provide flexibility, and allow for mobility of the connected functional domains. Rigid linkers can successfully keep a fixed distance between domains to maintain their independent functions, which can provide efficient separation of the protein domains and/or sufficiently reduce interference between functional domains. Cleavable linkers can allow one to control release of functional domains in vivo. By taking advantage of unique in vivo processes, cleavable linkers can be cleaved under specific conditions such as the presence of reducing reagents or proteases. This type of linker can reduce steric hindrance, improve bioactivity, and/or achieve independent actions/metabolism of individual domains of recombinant fusion proteins after linker cleavage.

Exemplary linkers are reflected in the amino acid sequences of SEQ ID NOs:12-18.

In one exemplary application, an anti-B7H3 polypeptide can be incorporated into a multispecific NK engager compound that includes, at a minimum, the anti-B7H3 protein and an NK engager domain.

Natural killer (NK) cells are cytotoxic lymphocytes of the innate immune system capable of immune surveillance. Like T cells, NK cells deliver a store of membrane penetrating and apoptosis-inducing granzyme and perforin granules. Unlike T cells, NK cells do not require antigen priming and recognize targets by engaging activating receptors in the absence of MHC recognition.

NK cells express CD16, an activation receptor that binds to the Fc portion of IgG antibodies and is involved in antibody-dependent cell-mediated cytotoxicity (ADCC). NK cells are regulated by IL-15, which can induce increased antigen-dependent cytotoxicity, lymphokine-activated killer activity, and/or mediate interferon (IFN), tumor-necrosis factor (TNF) and/or granulocyte-macrophage colony-stimulating factor (GM-CSF) responses. IL-15 can also drive NK cell proliferation and survival, thus enhancing expansion and persistence of NK cells. All of these IL-15-activated functions contribute to improved cancer defense.

Therapeutically, adoptive transfer of NK cells can, for example, induce remission in subjects with refractory acute myeloid leukemia (AML) when combined with lymphodepleting chemotherapy and IL-2 to stimulate survival and in vivo expansion of NK cells. This therapy can be limited by lack of antigen specificity and IL-2-mediated induction of regulatory T (Treg) cells that suppress NK cell proliferation and function. Generating a reagent that drives NK cell antigen specificity, expansion, and/or persistence, while bypassing the negative effects of Treg inhibition, can enhance NK-cell-based immunotherapies.

In one aspect, therefore, this disclosure describes the design, construction, and use of a trispecific molecule that includes two domains capable of driving NK-cell-mediated killing of $B7H3^+$ tumor cells and an intramolecular NK activating domain capable of generating an NK cell self-sustaining signal. The trispecific molecule can drive NK cell proliferation and/or enhance NK-cell-driven cytotoxicity against, for example, $B7H3^+$ cancer cells or $B7H3^+$ cancer cell-derived cell lines.

This disclosure describes, in one aspect, trispecific killer engager molecules that generally include a targeting domain that selectively targets B7H3, an NK cell engager domain (e.g., CD16, CD16+CD2, CD16+DNAM, NKp46, CD16+NKp46, NKG2D, NK2C), and an NK activating domains (e.g., IL-15, IL-12, IL-18, IL-21, or other NK cell enhancing cytokine, chemokine, and/or activating molecule), with each domain operably linked to the other domains. As used herein, the terms "selectively targets" and "selectively binds" refer to the ability to differentiate between two or more alternatives such as, for example, having differential affinity, to any degree, for a particular target. Particularly in the context of a trispecific compound, the term "operably linked" includes domains connected by mutual covalent linking to an intervening moiety (e.g., a flanking sequence, multiple flanking sequences, and/or another functional domain). Thus, two domains may be considered operably linked if, for example, they are separated by a third functional domain, with or without one or more intervening flanking sequences.

The targeting domain can include any moiety that selectively binds to a B7H3$^{+}$ target such as, for example, a tumor cell, a target in the cancer stroma, or an immobilized B7H3$^{+}$ cell. Thus, a targeting domain can include, for example, an anti-B7H3 antibody. In some embodiments, an anti-B7H3 antibody can include an anti-B7H3 polypeptide as described in detail herein. In one exemplary embodiment, the anti-B7H3 polypeptide can include one or more of the complementarity-determining regions (CDRs) of SEQ ID NO:1, SEQ ID NO:2, and SEQ ID NO:3. In some embodiments, the anti-B7H3 protein can include two or all three of the CDRs of SEQ ID NO:1, SEQ ID NO:2, and SEQ ID NO:3. In some embodiments, the anti-B7H3 protein can include SEQ ID NO:1, SEQ ID NO:2, or a variant thereof (e.g., SEQ ID NO:3). Suitable alternative variants are described herein.

The NK engaging domain can include any moiety that binds to and/or activates an NK cell and/or any moiety that blocks inhibition of an NK cell. In some embodiments, the NK engaging domain can include an antibody that selectively binds to a component of the surface of an NK cell. In other embodiments, the NK engaging domain can include a ligand or small molecule that selectively binds to a component of the surface of an NK cell. Thus, for brevity, reference to an antibody that selectively binds to a component of the surface of an NK cell includes any antibody fragment that exhibits the described binding character. Similarly, reference to a ligand that selectively binds to a component of the surface of an NK cell includes any fragment of the ligand that exhibits the described binding character.

In some embodiments, the NK engaging domain can selectively bind to a receptor at least partially located at the surface of an NK cell. In certain embodiments, the NK engaging domain can serve a function of binding an NK cell and thereby bring the NK cell into spatial proximity with a target to which the targeting domain selectively binds. In certain embodiments, however, the NK engaging domain can selectively bind to a receptor that activates the NK cell and, therefore, also possess an activating function. As described above, activation of the CD16 receptor can elicit antibody-dependent cell-mediated cytotoxicity. Thus, in certain embodiments, the NK engaging domain can include at least a portion of an anti-CD16 receptor antibody effective to selectively bind to the CD16 receptor. In other embodiments, the NK engager cell domain may interrupt mechanisms that inhibit NK cells. In such embodiments, the NK engager domain can include, for example, anti-PD1/PDL1, anti-NKG2A, anti-TIGIT, anti-killer-immunoglobulin receptor (KIR), and/or any other inhibition blocking domain.

One can design the NK engaging domain to possess a desired degree of NK selectivity and, therefore, a desired immune engaging character. For example, CD16 has been identified as Fc receptors FcγRIIIa (CD16a) and FcγRIIIb (CD16b). These receptors bind to the Fc portion of IgG antibodies that then activates the NK cell for antibody-dependent cell-mediated cytotoxicity. Anti-CD16 antibodies selectively bind to NK cells, but also can bind to neutrophils. Anti-CD16a antibodies selectively bind to NK cells, but do not bind to neutrophils. A trispecific killer engager compound that includes an NK engaging domain that includes an anti-CD16a antibody can bind to NK cells but not bind to neutrophils. Thus, in circumstances where one may want to engage NK cells but not engage neutrophils, one can design the NK engaging domain of the trispecific killer engager compound to include an anti-CD16a antibody.

In some embodiments, the NK cell engaging domain can involve the use of a humanized CD16 engager derived from an animal nanobody. While an scFv has a heavy variable chain component and a light variable chain component joined by a linker, a nanobody consists of a single monomeric variable chain—i.e., a variable heavy chin or a variable light chain—that is capable of specifically engaging a target. A single domain antibody (sdAb) may be derived from an antibody of any suitable animal such as, for example, a camelid (e.g., a llama or camel) or a cartilaginous fish. A single domain antibody can provide superior physical stability, an ability to bind deep grooves, and increased production yields compared to larger antibody fragments.

In one exemplary embodiment, an sdAb-based NK engager molecule can involve a humanized CD16 nanobody derived from a llama nanobody (GeneBank sequence FF561291; Behar et al., 2008. *Protein Eng Des Sel.* 21(1): 1-10), termed EF91. Upon confirming functionality of the molecule, the CDRs were cloned into a humanized camelid scaffold (Vincke et al., 2009. *J Biol Chem.* 284(5):3273-3284) to humanize the CD16 engager (SEQ ID NO:19). The use of a humanized camelid sdAb in the NK engaging domain of a trispecific killer engager compound can increase drug yield, increase stability, and/or increase NK-cell-mediated antibody-dependent cellular cytotoxicity (ADCC) efficacy.

While described herein in the context of various embodiments in which the NK engaging domain includes an anti-CD16 sdAb or anti-CD16 scFv, the NK engaging domain can include any antibody or other ligand that selectively binds to CD16. Moreover, the NK engaging domain can include an antibody or ligand that selectively binds to any NK cell receptor such as, for example, the cell cytotoxicity receptor 2B4, low affinity Fc receptor CD16, killer immunoglobulin like receptors (KIR), CD2, NKG2A, TIGIT, NKG2C, LIR-1, and/or DNAM-1.

In one aspect, the immune cell is a T cell or a natural killer (NK) cell. In another aspect, the immune cell is an NK cell; and the immune cell engaging domain includes a ligand or antibody that specifically binds to CD16. In some aspects, the antibody that specifically binds to CD16 includes a an scFv, a $F(ab)_2$, a Fab, or a single domain antibody.

As explained in more detail above, "antibody" refers generally an immunoglobulin or a fragment thereof and thus encompasses a monoclonal antibody, a fragment thereof (e.g., scFv, Fab, $F(ab')_2$, Fv, sdAb, or other modified form of an antibody, including a humanized form of an antibody or fragment thereof). Thus, for brevity, reference to an antibody that selectively binds to B7H3 includes any antibody or antibody fragment that exhibits the described binding character. Similarly, reference to an antibody that selectively binds to CD16 (or any other NK cell receptor) includes any antibody or antibody fragment that exhibits the described binding character. In some aspects, the immune cell engaging domain includes a ligand or antibody that specifically binds to CD16 such as, for example, an antibody fragment having the amino acid sequence set forth in SEQ ID NO:19.

In some embodiments, the NK engaging domain and the targeting domain can be linked using any one of the linkers reflected in SEQ ID NOs: 12-18. In particular embodiments, a bispecific anti-B7H3 compound can include the amino acid sequence of SEQ ID NO:20 or SEQ ID NO:21. In some embodiments, a bispecific anti-B7H3 compound can include the amino acid sequence of SEQ ID NO:20 or SEQ ID NO:21 with deletion of the leader sequence, a deletion of the VDE linker and HIS tag, or a deletion of both the leader sequence and the VDE linker and HIS tag.

In another aspect, the multispecific anti-B7H3 compound further includes an immune cell activating domain. In some embodiments, the immune cell can be an NK cell and the immune cell activating domain includes a NK activating cytokine or a functional portion thereof.

The NK activating domain can include a "immune cell activating domain", e.g., an amino acid sequence that activates NK cells, promotes sustaining NK cells, or otherwise promotes NK cell activity. For example, NK cells are responsive to a variety of cytokines including, but not limited to, IL-15, which is involved in NK cell homeostasis, proliferation, survival, activation, and/or development. IL-15 and IL-2 share several signaling components, including the IL-2/IL-15RD (CD122) and the common gamma chain (CD132). Unlike IL-2, IL-15 does not stimulate Tregs, allowing for NK cell activation while bypassing Treg inhibition of the immune response. Besides promoting NK cell homeostasis and proliferation, IL-15 can rescue NK cell functional defects that can occur in the post-transplant setting. IL-15 also can stimulate $CD8^+$ T cell function, further enhancing its immunotherapeutic potential. In addition, based on pre-clinical studies, toxicity profiles of IL-15 may be more favorable than IL-2 at low doses.

Therefore, the NK activating domain can be, or can be derived from, one or more cytokines that can activate and/or sustain NK cells. As used herein, the term "derived from" refers to an amino acid fragment of a cytokine (e.g., IL-15) that is sufficient to provide NK cell activating and/or sustaining activity. In embodiments that include more than one NK activating domain, the NK activating domains may be provided in series or in any other combination. Additionally, each cytokine-based NK activating domain can include either the full amino acid sequence of the cytokine or may be an amino acid fragment, independent of the nature of other NK activating domains included in the trispecific killer engager compound. Exemplary cytokines on which an NK activating domain may be based include, for example, IL-15, IL-18, IL-12, and IL-21. Thus, while described in detail herein in the context of an exemplary model embodiment in which the NK activating domain is derived from IL-15, a trispecific killer engager compound may be designed using an NK activating domain that is, or is derived from, any suitable cytokine.

For brevity in this description, reference to an NK activating domain by identifying the cytokine on which it is based includes both the full amino acid sequence of the cytokine, any suitable amino acid fragment of the cytokine, and or a modified version of the cytokine that includes one or more amino acid substitutions. Thus, reference to an "IL-15" NK activating domain includes an NK activating domain that includes the full amino acid sequence of IL-15, an NK activating domain that includes a fragment of IL-15 (e.g., SEQ ID NO:11), a functional variant thereof, or an NK activating domain that includes an amino acid substitution compared to the wild-type IL-15 amino acid sequence. For example, an NK activating domain can include a fragment of IL-15 that includes an N-to-D or an N-to-A amino acid substitution at position 72 of SEQ ID NO:11. Reference to position 72 of SEQ ID NO:11 merely refers to the location of the amino acid substitution regardless of the particular fragment of IL-15 that may be used as the NK activating domain. Thus, the NK activating domain can include a fragment of TL-15 other than the fragment reflected in SEQ ID NO:11 and that fragment can have an N-to-D or an N-to-A amino acid substitution at the position of the alternative IL-15 fragment that corresponds to position 72 of SEQ ID NO:11.

In some embodiments, trispecific anti-B7H3 compounds include domains linked by one or more of the linkers reflected in SEQ ID NOs:12-18 or a combination of the linkers reflected in SEQ ID NOs:12-18. In specific exemplary embodiments, the NK engaging domain is linked to the NK activating domain using the linker of SEQ ID NO:14, while the NK activating domain is linked to the targeting domain using the linker of SEQ ID NO:15 (e.g., SEQ ID NOs:22-25).

In another aspect, this disclosure describes an isolated nucleic acid sequence that encodes any embodiment of an anti-B7H3 compound. one of the compounds described herein. In some embodiments, the isolated nucleic is the nucleic acid sequence of any one of SEQ ID NOs: 26-33. Given the amino acid sequence of any anti-B7H3 polypeptide, or multispecific anti-B7H3 compound that includes an anti-B7H3 polypeptide, a person of ordinary skill in the art can determine the full scope of polynucleotides that encode that amino acid sequence using conventional, routine methods.

In another aspect, this disclosure describes an isolated nucleic acid sequence that encodes any embodiment of an anti-B7H3 compound. one of the compounds described herein. In some embodiments, the isolated nucleic acid sequence is the nucleic acid sequence of any one of SEQ ID NOs: 26-33. Given the amino acid sequence of any anti-B7H3 polypeptide, or multispecific anti-B7H3 compound that includes an anti-B7H3 polypeptide, a person of ordinary skill in the art can determine the full scope of polynucleotides that encode that amino acid sequence using conventional, routine methods.

As used herein "amplified DNA" or "PCR product" refers to an amplified fragment of DNA of defined size. Various techniques are available and well known in the art to detect PCR products. PCR product detection methods include, but are not restricted to, gel electrophoresis using agarose or polyacrylamide gel and adding ethidium bromide staining (a DNA intercalant), labeled probes (radioactive or non-radioactive labels, southern blotting), labeled deoxyribonucleotides (for the direct incorporation of radioactive or non-radioactive labels) or silver staining for the direct visualization of the amplified PCR products; restriction endonuclease digestion, that relies agarose or polyacrylamide gel or high-performance liquid chromatography (HPLC); dot blots, using the hybridization of the amplified DNA on specific labeled probes (radioactive or non-radioactive labels); high-pressure liquid chromatography using ultraviolet detection; electro-chemiluminescence coupled with voltage-initiated chemical reaction/photon detection; and direct sequencing using radioactive or fluorescently labeled deoxyribonucleotides for the determination of the precise order of nucleotides with a DNA fragment of interest, oligo ligation assay (OLA), PCR, qPCR, DNA sequencing, fluorescence, gel electrophoresis, magnetic beads, allele specific primer extension (ASPE) and/or direct hybridization.

Generally, nucleic acid can be extracted, isolated, amplified, or analyzed by a variety of techniques such as those described by Green and Sambrook, Molecular Cloning: A Laboratory Manual (Fourth Edition), Cold Spring Harbor Laboratory Press, Woodbury, NY 2,028 pages (2012); or as described in U.S. Pat. Nos. 7,957,913; 7,776,616; 5,234,809; U.S. Pub. 2010/0285578; and U.S. Pub. 2002/0190663. Examples of nucleic acid analysis include, but are not limited to, sequencing and DNA-protein interaction. Sequencing may be by any method known in the art. DNA sequencing techniques include classic dideoxy sequencing reactions (Sanger method) using labeled terminators or primers and gel separation in slab or capillary, and next generation sequencing methods such as sequencing by synthesis using reversibly terminated labeled nucleotides, pyrosequencing, 454 sequencing, Illumina/Solexa sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, polony sequencing, and SOLiD sequencing. Separated molecules may be sequenced by sequential or single extension reactions using polymerases or ligases as well as by single or sequential differential hybridizations with libraries of probes.

In another aspect, this disclosure describes proteins encoded by any of the nucleic acid sequences described herein. In some embodiments, the protein can have an amino acid sequence that includes the amino acid sequence of SEQ ID NO:1, SEQ ID NO:2, SEQ ID NO:9, SEQ ID NO:10, SEQ ID NO:20, SEQ ID NO:21, SEQ ID NO:22, SEQ ID NO:23, SEQ ID NO:24, SEQ ID NO:25, or any protein having 90% or greater amino acid identity thereto.

In another aspect, this disclosure describes a host cell including any of the isolated nucleic acid sequences and/or proteins described herein.

The nucleic acid constructs of the present invention may be introduced into a host cell to be altered, thus allowing expression of the chimeric protein within the cell, thereby generating a genetically engineered cell. A variety of methods are known in the art and suitable for introduction of nucleic acid into a cell, including viral and non-viral mediated techniques. Examples of typical non-viral mediated techniques include, but are not limited to, electroporation, calcium phosphate mediated transfer, nucleofection, sonoporation, heat shock, magnetofection, liposome mediated transfer, microinjection, microprojectile mediated transfer (nanoparticles), cationic polymer mediated transfer (DEAE-dextran, polyethylenimine, polyethylene glycol (PEG) and the like) or cell fusion. Other methods of transfection include proprietary transfection reagents such as LIPOFECTAMINE (Thermo Fisher Scientific, Inc., Waltham, MA), HILYMAX (Dojindo Molecular Technologies, Inc., Rockville, MD), FUGENE (Promega Corp., Madison, WI), JETPEI (Polyplus Transfection, Illkirch, France), EFFECTENE (Qiagen, Hilden, Germany) and DREAMFECT (OZ Biosciences, Inc USA, San Diego, CA).

The nucleic acid constructs described herein may be introduced into a host cell to be altered, thus allowing expression within the cell of the protein encoded by the nucleic acid. A variety of host cells are known in the art and suitable for protein expression. Examples of typical cell used for transfection and protein expression include, but are not limited to, a bacterial cell, a eukaryotic cell, a yeast cell, an insect cell, or a plant cell such as, for example, *E. coli, Bacillus, Streptomyces, Pichia pastoris, Salmonella typhimurium, Drosophila* S2, *Spodoptera* SJ9, CHO, COS (e.g., COS-7),3T3-F442A, HeLa, HUVEC, HUAEC, NIH 3T3, Jurkat, 293, 293H, or 293F.

In some aspects, the host cell is a T cell, an NK cell, or a macrophage.

In a further aspect, this disclosure describes a pharmaceutical composition that includes any one of the multispecific anti-B7H3 compounds described herein and a pharmaceutically acceptable carrier.

A multispecific anti-B7H3 compound, such as a trispecific killer engager compound as described herein may be formulated with a pharmaceutically acceptable carrier. As used herein, "carrier" includes any solvent, dispersion medium, vehicle, coating, diluent, antibacterial, and/or antifungal agent, isotonic agent, absorption delaying agent, buffer, carrier solution, suspension, colloid, and the like. The use of such media and/or agents for pharmaceutical active substances is well known in the art. Except insofar as any conventional media or agent is incompatible with the active ingredient, its use in the therapeutic compositions is contemplated. Supplementary active ingredients also can be incorporated into the compositions. As used herein, "pharmaceutically acceptable" refers to a material that is not biologically or otherwise undesirable, i.e., the material may be administered to an individual along with a trispecific killer engager compound without causing any undesirable biological effects or interacting in a deleterious manner with any of the other components of the pharmaceutical composition in which it is contained.

A multispecific compound, such as a trispecific killer engager compound may therefore be formulated into a pharmaceutical composition. The pharmaceutical composition may be formulated in a variety of forms adapted to a preferred route of administration. Thus, a composition can be administered via known routes including, for example, oral, parenteral (e.g., intradermal, transcutaneous, subcutaneous, intramuscular, intravenous, intraperitoneal, etc.), or topical (e.g., intranasal, intrapulmonary, intramammary, intravaginal, intrauterine, intradermal, transcutaneous, rectally, etc.). A pharmaceutical composition can be administered to a mucosal surface, such as by administration to, for example, the nasal or respiratory mucosa (e.g., by spray or aerosol). A composition also can be administered via a sustained or delayed release.

Thus, a multispecific compound, such as a trispecific killer engager compound may be provided in any suitable form including but not limited to a solution, a suspension, an emulsion, a spray, an aerosol, or any form of mixture. The composition may be delivered in formulation with any pharmaceutically acceptable excipient, carrier, or vehicle. For example, the formulation may be delivered in a conventional topical dosage form such as, for example, a cream, an ointment, an aerosol formulation, a non-aerosol spray, a gel, a lotion, and the like. The formulation may further include one or more additives including such as, for example, an adjuvant, a skin penetration enhancer, a colorant, a fragrance, a flavoring, a moisturizer, a thickener, and the like.

A formulation may be conveniently presented in unit dosage form and may be prepared by methods well known in the art of pharmacy. Methods of preparing a composition with a pharmaceutically acceptable carrier include the step of bringing a multispecific compound or trispecific killer engager compound into association with a carrier that constitutes one or more accessory ingredients. In general, a formulation may be prepared by uniformly and/or intimately bringing the active molecule into association with a liquid carrier, a finely divided solid carrier, or both, and then, if necessary, shaping the product into the desired formulations.

The amount of multispecific compound or trispecific killer engager compound administered can vary depending on various factors including, but not limited to, the specific trispecific killer engager compound being used, the weight, physical condition, and/or age of the subject, and/or the route of administration. Thus, the absolute weight of trispecific killer engager compound included in a given unit dosage form can vary widely, and depends upon factors such as the species, age, weight and physical condition of the subject, and/or the method of administration. Accordingly, it is not practical to set forth generally the amount that constitutes an amount of multispecific compound or trispecific killer engager compound effective for all possible applications. Those of ordinary skill in the art, however, can readily determine the appropriate amount with due consideration of such factors.

In some embodiments, the method can include administering sufficient multispecific compound or trispecific killer engager compound to provide a dose of, for example, from about 100 ng/kg to about 50 mg/kg to the subject, although in some embodiments the methods may be performed by administering the multispecific compound or trispecific killer engager compound in a dose outside this range. In some of these embodiments, the method includes administering sufficient the multispecific compound or trispecific killer engager compound to provide a dose of from about 10 μg/kg to about 5 mg/kg to the subject, for example, a dose of from about 100 μg/kg to about 1 mg/kg.

Alternatively, the dose may be calculated using actual body weight obtained just prior to the beginning of a treatment course. For the dosages calculated in this way, body surface area ($m^2$) is calculated prior to the beginning of the treatment course using the Dubois method: $m^2$=(wt $kg^{0.425}$×height $cm^{00.725}$)×0.007184.

In some embodiments, the method can include administering sufficient the multispecific compound or trispecific killer engager compound to provide a dose of, for example, from about 0.01 $mg/m^2$ to about 10 $mg/m^2$.

In another aspect, this disclosure describes a method including administering to a subject a multispecific compound in an amount effective to induce NK-mediated killing of a cell, the multispecific compound including a targeting domain including one of the anti-B7H3 proteins described herein; and an NK engaging domain operably linked to the anti-B7H3 protein.

In another aspect, this disclosure describes a method for stimulating expansion of NK cells in vivo including administering to a subject an effective amount of multispecific compound including a targeting domain including one of the anti-B7H3 proteins described herein; and an NK engaging domain operably linked to the anti-B7H3 protein.

In another aspect, this disclosure describes methods of killing a target cell in a subject. Generally, the method includes administering to the subject an anti-B7H3 multispecific compound in an amount effective to induce NK-mediated killing of the target cells. "Treat" or variations thereof refer to reducing, limiting progression, ameliorating, or resolving, to any extent, the symptoms or signs related to a condition. As used herein, "ameliorate" refers to any reduction in the extent, severity, frequency, and/or likelihood of a symptom or clinical sign characteristic of a particular condition; "symptom" refers to any subjective evidence of disease or of a subject's condition; and "sign" or "clinical sign" refers to an objective physical finding relating to a particular condition capable of being found by one other than the subject.

A "treatment" may be therapeutic or prophylactic. "Therapeutic" and variations thereof refer to a treatment that ameliorates one or more existing symptoms or clinical signs associated with a condition. "Prophylactic" and variations thereof refer to a treatment that limits, to any extent, the development and/or appearance of a symptom or clinical sign of a condition. Generally, a "therapeutic" treatment is initiated after the condition manifests in a subject, while "prophylactic" treatment is initiated before a condition manifests in a subject. Thus, in certain embodiments, the method can involve prophylactic treatment of a subject at risk of developing a condition. "At risk" refers to a subject that may or may not actually possess the described risk. Thus, for example, a subject "at risk" for developing a specified condition is a subject that possesses one or more indicia of increased risk of having, or developing, the specified condition compared to individuals who lack the one or more indicia, regardless of the whether the subject manifests any symptom or clinical sign of having or developing the condition. Exemplary indicia of a condition can include, for example, genetic predisposition, ancestry, age, sex, geographical location, lifestyle, or medical history. Treatment may also be continued after symptoms have resolved, for example to prevent or delay their recurrence.

In some cases, the treatment can involve administering the anti-B7H3 multispecific compound to a subject so that the anti-B7H3 multispecific compound can stimulate endogenous NK cells in vivo. Using an anti-B7H3 multispecific compound as a part of an in vivo can make NK cells antigen specific with simultaneous co-stimulation, enhancement of survival, and expansion, which may be antigen specific. In other cases, the anti-B7H3 multispecific compound can be used in vitro as an adjuvant to NK cell adoptive transfer therapy. The terms "administration of" and or "administering" should be understood to mean providing a pharmaceutical composition in a therapeutically effective amount to the subject in need of treatment. Administration routes can be enteral, topical, or parenteral. As such, administration routes include but are not limited to intracutaneous, subcutaneous, intravenous, intraperitoneal, intraarterial, intrathecal, intracapsular, intraorbital, intracardiac, intradermal, transdermal, transtracheal, subcuticular, intraarticular, subcapsular, subarachnoid, intraspinal, intrasternal, oral, sublingual buccal, rectal, vaginal, nasal ocular administrations, as well infusion, inhalation, and nebulization. The phrases "parenteral administration" and "administered parenterally" as used herein means modes of administration other than enteral and topical administration.

Accordingly, an anti-B7H3 multispecific compound may be administered before, during, or after the subject first exhibits a symptom or clinical sign of the condition. Treatment initiated before the subject first exhibits a symptom or clinical sign associated with the condition may result in decreasing the likelihood that the subject experiences clinical evidence of the condition compared to a subject to which the anti-B7H3 multispecific compound is not administered, decreasing the severity of symptoms and/or clinical signs of the condition, and/or completely resolving the condition. Treatment initiated after the subject first exhibits a symptom or clinical sign associated with the condition may result in decreasing the severity of symptoms and/or clinical signs of the condition compared to a subject to which the composition is not administered, and/or completely resolving the condition.

The anti-B7H3 multispecific compound can be any embodiment of the anti-B7H3 multispecific compound described above having a targeting domain that selectively binds to an appropriate target cell population. In some cases, the target cell can include a tumor cell so that the method can involve treating cancer associated with the tumor cells. Thus, in some embodiments, the method can include ameliorating at least one symptom or clinical sign of the tumor.

In embodiments in which the target cell includes a tumor cell, the method can further include surgically resecting the tumor and/or reducing the size of the tumor through chemical (e.g., chemotherapeutic) and/or radiation therapy. Exemplary tumors that may be treated include tumors associated with prostate cancer, lung cancer, colon cancer, rectum cancer, urinary bladder cancer, melanoma, kidney cancer, renal cancer, oral cavity cancer, pharynx cancer, pancreas cancer, uterine cancer, thyroid cancer, skin cancer, head and neck cancer, cervical cancer, ovarian cancer and/or hematopoietic cancer.

Thus, in some embodiments, treating a subject includes a subject having, or at risk of having cancer. Generally, the method includes administering to the subject an effective amount of multispecific compound including a targeting domain including one of the anti-B7H3 proteins described herein and an NK engaging domain operably linked to the anti-B7H3 protein. As used herein, the term "cancer" refers to a group of diseases characterized by abnormal and uncontrolled cell proliferation starting at one site (primary site) with the potential to invade and to spread to other sites (secondary sites, metastases) which differentiates cancer (malignant tumor) from benign tumor. Virtually any organ can be affected, meaning more than 100 types of cancer can affect humans. Cancers can result from many causes including genetic predisposition, viral infection, exposure to ionizing radiation, exposure to an environmental pollutant, tobacco and/or alcohol use, obesity, poor diet, lack of physical activity, or any combination thereof. As used herein, "neoplasm" or "tumor" (and grammatical variations thereof) means new and abnormal growth of tissue, which may be benign or cancerous. In a related aspect, the neoplasm is indicative of a neoplastic disease or disorder, including but not limited, to various cancers. For example, such cancers can include prostate, pancreatic, biliary, colon, rectal, liver, kidney, lung, testicular, breast, ovarian, brain, and head and neck cancers, melanoma, sarcoma, multiple myeloma, leukemia, lymphoma, and the like.

Exemplary cancers described by the national cancer institute include: Acute Lymphoblastic Leukemia, Adult; Acute Lymphoblastic Leukemia, Childhood; Acute Myeloid Leukemia, Adult; Adrenocortical Carcinoma; Adrenocortical Carcinoma, Childhood; AIDS-Related Lymphoma; AIDS-Related Malignancies; Anal Cancer; Astrocytoma, Childhood Cerebellar; Astrocytoma, Childhood Cerebral; Bile Duct Cancer, Extrahepatic; Bladder Cancer; Bladder Cancer, Childhood; Bone Cancer, Osteosarcoma/Malignant Fibrous Histiocytoma; Brain Stem Glioma, Childhood; Brain Tumor, Adult; Brain Tumor, Brain Stem Glioma, Childhood; Brain Tumor, Cerebellar Astrocytoma, Childhood; Brain Tumor, Cerebral Astrocytoma/Malignant Glioma, Childhood; Brain Tumor, Ependymoma, Childhood; Brain Tumor, Medulloblastoma, Childhood; Brain Tumor, Supratentorial Primitive Neuroectodermal Tumors, Childhood; Brain Tumor, Visual Pathway and Hypothalamic Glioma, Childhood; Brain Tumor, Childhood (Other); Breast Cancer; Breast Cancer and Pregnancy; Breast Cancer, Childhood; Breast Cancer, Male; Bronchial Adenomas/Carcinoids, Childhood: Carcinoid Tumor, Childhood; Carcinoid Tumor, Gastrointestinal; Carcinoma, Adrenocortical; Carcinoma, Islet Cell; Carcinoma of Unknown Primary; Central Nervous System Lymphoma, Primary; Cerebellar Astrocytoma, Childhood; Cerebral Astrocytoma/Malignant Glioma, Childhood; Cervical Cancer; Childhood Cancers; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer, Childhood; Cutaneous T-Cell Lymphoma; Endometrial Cancer; Ependymoma, Childhood; Epithelial Cancer, Ovarian; Esophageal Cancer; Esophageal Cancer, Childhood; Ewing's Family of Tumors; Extracranial Germ Cell Tumor, Childhood; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer, Childhood; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma. Childhood Brain Stem; Glioma. Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma, Adult; Hodgkin's Lymphoma, Childhood; Hodgkin's Lymphoma During Pregnancy; Hypopharyngeal Cancer; Hypothalamic and Visual Pathway Glioma, Childhood; Intraocular Melanoma; Islet Cell Carcinoma (Endocrine Pancreas); Kaposi's Sarcoma; Kidney Cancer; Laryngeal Cancer; Laryngeal Cancer, Childhood; Leukemia, Acute Lymphoblastic, Adult; Leukemia, Acute Lymphoblastic, Childhood; Leukemia, Acute Myeloid, Adult; Leukemia, Acute Myeloid, Childhood; Leukemia, Chronic Lymphocytic; Leukemia, Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoblastic Leukemia, Adult Acute; Lymphoblastic Leukemia, Childhood Acute; Lymphocytic Leukemia, Chronic; Lymphoma, AIDS Related; Lymphoma, Central Nervous System (Primary); Lymphoma, Cutaneous T-Cell; Lymphoma, Hodgkin's, Adult; Lymphoma, Hodgkin's; Childhood; Lymphoma, Hodgkin's During Pregnancy; Lymphoma, Non-Hodgkin's, Adult; Lymphoma, Non-Hodgkin's, Childhood; Lymphoma, Non-Hodgkin's During Pregnancy; Lymphoma, Primary Central Nervous System; Macroglobulinemia, Waldenstrom's; Male Breast Cancer; Malignant Mesothelioma, Adult; Malignant Mesothelioma, Childhood; Malignant Thymoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplasia Syndromes; Myelogenous Leukemia, Chronic; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer, Childhood; Neuroblastoma; Non-Hodgkin's Lymphoma, Adult; Non-Hodgkin's Lymphoma, Childhood; Non-Hodgkin's Lymphoma During Pregnancy; Non-Small Cell Lung Cancer; Oral Cancer, Childhood; Oral Cavity and Lip Cancer; Oropharyngeal Cancer; Osteosarcoma/Malignant Fibrous Histiocytoma of Bone; Ovarian Cancer, Childhood; Ovarian Epithelial Cancer; Ovarian Germ Cell Tumor; Ovarian Low Malignant Potential Tumor; Pancreatic Cancer; Pancreatic Cancer, Childhood, Pancreatic Cancer, Islet Cell; Paranasal Sinus and Nasal Cavity Cancer; Parathyroid Cancer; Penile Cancer; Pheochromocytoma; Pineal and Supratentorial Primitive Neuroectodermal Tumors, Childhood; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer, Adult; Primary Liver Cancer, Childhood; Prostate Cancer; Rectal Cancer; Renal Cell (Kidney) Cancer; Renal Cell Cancer, Childhood; Renal Pelvis and Ureter, Transitional Cell Cancer; Retinoblastoma; Rhabdomyosarcoma, Childhood; Salivary Gland Cancer; Salivary Gland's Cancer, Childhood; Sarcoma, Ewing's Family of Tumors; Sarcoma, Kaposi's;

Sarcoma (Osteosarcoma) Malignant Fibrous Histiocytoma of Bone; Sarcoma, Rhabdomyosarcoma, Childhood; Sarcoma, Soft Tissue, Adult; Sarcoma, Soft Tissue, Childhood; Sezary Syndrome; Skin Cancer; Skin Cancer, Childhood; Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Neck Cancer with Occult Primary, Metastatic; Stomach (Gastric) Cancer; Stomach (Gastric) Cancer, Childhood; Supratentorial Primitive Neuroectodermal Tumors, Childhood; T-Cell Lymphoma, Cutaneous; Testicular Cancer; Thymoma, Childhood; Thymoma, Malignant; Thyroid Cancer; Thyroid Cancer, Childhood; Transitional Cell Cancer of the Renal Pelvis and Ureter; Trophoblastic Tumor, Gestational; Unknown Primary Site, Cancer of, Childhood; Unusual Cancers of Childhood; Ureter and Renal Pelvis, Transitional Cell Cancer; Urethral Cancer; Uterine Sarcoma; Vaginal Cancer; Visual Pathway and Hypothalamic Glioma, Childhood; Vulvar Cancer; Waldenstrom's Macro globulinemia; and Wilms' Tumor.

In some embodiments, the cancer can include or involve prostate cancer, lung cancer, colon cancer, rectum cancer, urinary bladder cancer, melanoma, kidney cancer, renal cancer, oral cavity cancer, pharynx cancer, pancreas cancer, uterine cancer, thyroid cancer, skin cancer, head and neck cancer, cervical cancer, ovarian cancer, and/or hematopoietic cancer.

In one aspect, the multispecific compound is administered prior to, simultaneously with, or following chemotherapy, surgical resection of a tumor, or radiation therapy.

In some embodiments, a multispecific compound or trispecific killer engager compound may be administered, for example, from a single dose to multiple doses per week, although in some embodiments the method can be performed by administering a trispecific killer engager compound at a frequency outside this range. In certain embodiments, a multispecific compound or trispecific killer engager compound may be administered from about once per month to about five times per week.

In some embodiments, the method further includes administering one or more additional therapeutic agents. The one or more additional therapeutic agents may be administered before, after, and/or coincident to the administration of a multispecific compound or trispecific killer engager compound. A multispecific compound or trispecific killer engager compound and the additional therapeutic agents may be co-administered. As used herein, "co-administered" refers to two or more components of a combination administered so that the therapeutic or prophylactic effects of the combination can be greater than the therapeutic or prophylactic effects of either component administered alone. Two components may be co-administered simultaneously or sequentially. Simultaneously co-administered components may be provided in one or more pharmaceutical compositions. Sequential co-administration of two or more components includes cases in which the components are administered so that each component can be present at the treatment site at the same time. Alternatively, sequential co-administration of two components can include cases in which at least one component has been cleared from a treatment site, but at least one cellular effect of administering the component (e.g., cytokine production, activation of a certain cell population, etc.) persists at the treatment site until one or more additional components are administered to the treatment site. Thus, a co-administered combination can, in certain circumstances, include components that never exist in a chemical mixture with one another. In other embodiments, the multispecific compound or trispecific killer engager compound and the additional therapeutic agent may be administered as part of a mixture or cocktail. In some aspects, the administration of the multispecific compound or trispecific killer engager compound may allow for the effectiveness of a lower dosage of other therapeutic modalities when compared to the administration of the other therapeutic agent or agents alone, thereby decreasing the likelihood, severity, and/or extent of the toxicity observed when a higher dose of the other therapeutic agent or agents is administered.

The term "chemotherapeutic agent" as used herein refers to any therapeutic agent used to treat cancer. Examples of chemotherapeutic agents include, but are not limited to, actinomycin, azacitidine, azathioprine, bleomycin, bortezomib, carboplatin, capecitabine, cisplatin, chlorambucil, cyclophosphamide, cytarabine, daunorubicin, docetaxel, doxifluridine, doxorubicin, epirubicin, epothilone, etoposide, fluorouracil, gemcitabine, hydroxyurea, idarubicin, imatinib, irinotecan, mechlorethamine, mercaptopurine, methotrexate, mitoxantrone, oxaliplatin, paclitaxel, pemetrexed, teniposide, tioguanine, topotecan, valrubicin, vinblastine, vincristine, vindesine, vinorelbine, panitumamab, ERBITUX™ (cetuximab), matuzumab, IMC-JJF 8, TheraCIM hR3, denosumab, AVASTIN™ (bevacizumab), HUMIRA™ (adalimumab), HERCEPTIN™ (trastuzumab), REMICADE™ (infliximab), rituximab, SYNAGIS™ (palivizumab), MYLOTARG™ (gemtuzumab oxogamicin), RAPTIVA™ (efalizumab), TYSABRI™ (natalizumab), ZENAPAX™ (dacliximab), NEUTROSPEC™ (Technetium (99mTc) fanolesomab), tocilizumab, PROSTASCINT™ (Indium-III labeled Capromab Pendetide), BEXXAR™ (tositumomab), ZEVALIN™ (ibritumomab tiuxetan (IDEC-Y2B8) conjugated to yttrium 90), XOLAIR™ (omalizumab), MABTHERA™ (Rituximab), REOPRO™ (abciximab), MABCAMPATH™ (alemtuzumab), SIMULECT™ (basiliximab), LEUKOSCAN™ (sulesomab), CEA-SCAN™ (arcitumomab), VERLUMA™ (nofetumomab), PANOREX™ (Edrecolomab), alemtuzumab, CDP 870, natalizumab GILOTRIF™ (afatinib), LYNPARZA™ (olaparib), PERJETA™ (pertuzumab), OTDIVO™ (nivolumab), BOSULIF™ (bosutinib), CABOMETYX™ (cabozantinib), OGIVRI™ (trastuzumab-dkst), SUTENT™ (sunitinib malate), ADCETRIS™ (brentuximab vedotin), ALECENSA™ (alectinib), CALQUENCE™ (acalabrutinib), YESCARTA™ (ciloleucel), VERZENIO™ (abemaciclib), KEYTRUDA™ (pembrolizumab), ALIQOPA™ (copanlisib), Nerlynx™ (neratinib), IMFINZI™ (durvalumab), DARZALEX™ (daratumumab), TECENTRIQ™ (atezolizumab), and TARCEVA™ (erlotinib). Examples of immunotherapeutic agent include, but are not limited to, interleukins (I1-2, I1-7, I1-12), cytokines (Interferons, G-CSF, imiquimod), chemokines (CCL3, CC126, CXCL7), immunomodulatory imide drugs (thalidomide and its analogues).

In some aspects, the chemotherapy is selected from the group consisting of altretamine, amsacrine, L-asparaginase, colaspase, bleomycin, busulfan, capecitabine, carboplatin, carmustine, chlorambucil, cisplatin, cladribine, cyclophosphamide, cytophosphane, cytarabine, dacarbazine, dactinomycin, daunorubicin, docetaxel, doxorubicin, epirubicin, etoposide, fluorouracil, fludarabine, fotemustine, ganciclovir, gemcitabine, hydroxyurea, idarubicin, ifosfamaide, irinotecan, lomustine, melphalan, mercaptopurine, methotrexate, mitoxantrone, mitomycin C, nimustine, oxaliplatin, paclitaxel, pemetrexed, procarbazine, raltitrexed, temozolomide, teniposide, tioguanine, thiotepa, topotecan, vinblastine, vincristine, vindesine, and vinorelbine.

In some embodiments, of the method can include administering sufficient multispecific compound or trispecific killer engager compound as described herein and administering the at least one additional therapeutic agent demonstrates therapeutic synergy. In some aspects of the methods of the present invention, a measurement of response to treatment observed after administering both a multispecific compound or trispecific killer engager compound as described herein and the additional therapeutic agent is improved over the same measurement of response to treatment observed after administering either the multispecific compound or trispecific killer engager compound or the additional therapeutic agent alone.

The term "subject" as used herein refers to any individual or subject to which the subject methods are performed. In many embodiments, the subject is human, although the subject may be any non-human animal. Suitable non-human animals include, but are limited to, a vertebrate such as a rodent (including a mouse, a rat, a hamster, or a guinea pig), a cat, a dog, a rabbit, a farm animal (including a cow, a horse, a goat, a sheep, a pig, a chicken, etc.), or a primate (including a monkey, a chimpanzee, an orangutan, or a gorilla).

In some embodiments of this aspect, the anti-B7H3 multispecific compound can include an immune cell activating domain that includes IL-15, or a functional portion thereof, operably linked to the NK engaging domain. In some embodiments, the multispecific anti-B7H3 compound can have the amino acid sequence as set forth in any one of SEQ ID NOs:20-25.

In another aspect, this disclosure describes a chimeric antigen receptor compound that includes one of the anti-B7H3 proteins described herein. Chimeric antigen receptors (CARs, also known as chimeric immunoreceptors, chimeric T cell receptors, or artificial T cell receptors) are receptor proteins that have been engineered to give T cells the new ability to target a specific protein. The receptors are chimeric because they combine both antigen binding and T cell activating functions into a single receptor.

CAR-T cell therapy uses T cells engineered with CARs for cancer therapy. The premise of CAR-T immunotherapy is to modify T cells to recognize cancer cells to target and destroy the cancer cells more effectively. T cells are harvested from a donor (autologous or allogeneic), genetically altered, then the resulting CAR-T cells are infused into a subject to attack the subject's tumor. CAR-T cells can be either derived from T cells in a subject's own blood (autologous) or derived from the T cells of a donor (allogeneic). Once isolated from a person, these T cells are genetically engineered to express a specific CAR that programs the T cells to target an antigen that is present on the surface of a tumor. For safety, CAR-T cells are engineered to be specific to an antigen expressed on a tumor that is not expressed on healthy cells. After CAR-T cells are infused into a subject, they act as a "living drug" against cancer cells. When the CAR-T cells contact their targeted antigen on a cell, CAR-T cells bind to the antigen, become activated, proliferate, and become cytotoxic. CAR-T cells destroy cells through several mechanisms including extensive stimulated cell proliferation, increasing the degree to which they are toxic to other living cells (cytotoxicity), and by inducing increased secretion of factors that can affect other cells (e.g., cytokines, interleukins, and/or growth factors).

In another aspect, this disclosure describes a targeted therapeutic compound that includes a targeting domain and a therapeutic domain linked to the targeting domain. The targeting domain includes any embodiment of the anti-B7H3 proteins described herein. In some embodiments, the targeted therapeutic compound can provide immunotherapy and, therefore, be a targeted immunotherapeutic compound. In some embodiments, the therapeutic domain can include a drug, a therapeutic radioisotope, a toxin, a cytokine, or a chemokine.

As used herein, the term "drug" refers to any chemical substance, which, when administered to a living organism, produces a biological effect. A pharmaceutical drug is a chemical substance used to treat, cure, prevent, or diagnose a disease or to promote well-being. Drugs can be obtained through extraction from medicinal plants, or by organic synthesis. Pharmaceutical drugs may be used for a limited duration, or on a regular basis for chronic disorders.

A "radioisotope" or "radionuclide" is an atom that has excess nuclear energy, making it unstable. This excess energy can be used in one of three ways: emitted from the nucleus as gamma radiation; transferred to one of its electrons to release it as a conversion electron; or used to create and emit a new particle (alpha particle or beta particle) from the nucleus. During those processes, the radionuclide is said to undergo radioactive decay. These emissions are considered ionizing radiation because they are powerful enough to liberate an electron from another atom. The radioactive decay can produce a stable nuclide or will sometimes produce a new unstable radionuclide that may undergo further decay.

As used herein, the term "toxin" refers to a substance harmful to cells. Toxins can be small molecules, peptides, or proteins that are capable of causing disease or cell death on contact with, or absorption by, body tissues. Toxins vary greatly in their toxicity. Toxins are largely secondary metabolites, which are organic compounds that are not directly involved in an organism's growth, development, or reproduction, instead often aiding the organism in matters of defense. In some applications, a toxin may be used therapeutically by targeting the effect of the toxin toward an undesirable cell or cells (e.g., tumor cells).

Cytokines are a broad category of small proteins (~5-20 kDa) involved in cell signaling. Cytokines are peptides and cannot cross the lipid bilayer of cells to enter the cytoplasm, but are nevertheless involved in autocrine, paracrine, and endocrine signaling as immunomodulating agents. Cytokines include chemokines, interferons, interleukins, lymphokines, and tumor necrosis factors, but generally not hormones or growth factors (despite some overlap in the terminology). Cytokines are produced by a broad range of cells, including immune cells such as macrophages, B lymphocytes, T lymphocytes, mast cells, endothelial cells, fibroblasts, and various stromal cells. Cytokines modulate the balance between humoral and cell-based immune responses, and they regulate the maturation, growth, and responsiveness of particular cell populations.

In a further aspect, this disclosure describes a targeted imaging compound that includes a targeting domain and an imaging domain linked to the targeting domain. The targeting domain includes any embodiment of one of the anti-B7H3 proteins described herein. The imaging domain can include any moiety that can produce a detectable signal. Exemplary imaging moieties include, but are not limited to a colorimetric label, a fluorescent label, a radioactive label, a magnetic label, or an enzymatic label.

In yet another aspect, this disclosure describes a capture assay device including any embodiment of one of the anti-B7H3 proteins described herein immobilized to a substrate. For example, an anti-B7H3 protein described herein can be incorporated into cell and/or ligand capture technology such as, for example, an ELISA-based assay. A substrate to immobilize the anti-B7H3 proteins can include, for example, a cell culture plate or dish, a glass slide, or any other support than can be used to perform an assay requiring an immobilized anti-B7H3 protein.

In the preceding description and following claims, the term "and/or" means one or all of the listed elements or a combination of any two or more of the listed elements; the terms "comprises," "comprising," and variations thereof are to be construed as open ended i.e., additional elements or steps are optional and may or may not be present; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

Presented below are examples discussing trispecific compounds including a B7H3 binding protein contemplated for the discussed applications. The following examples are provided to further illustrate the embodiments of the present invention but are not intended to limit the scope of the invention. While they are typical of those that might be used, other procedures, methodologies, or techniques known to those skilled in the art may alternatively be used.

EXAMPLES

Example 1

Construction of Cam1615B7H3 Trispecific Killer Engager Compounds

The CDR regions from a camelid (llama) anti-CD16 (Behar et al., *Protein Eng Des Sel.* 2008; 21(1):1-10. doi: 10.1093/protein/gzm064. PubMed PMID: 18073223) were spliced into a universal, humanized, heavy chain scaffold (Vincke et al., *J Biol Chem.* 2009; 284(5):3273-84. doi: 10.1074/jbc.M806889200. PubMed PMID: 19010777). This new, humanized camelid sequence was used to manufacture sdAb B7H3 trispecific killer engager. A hybrid coding region encoding cam16, an $(SGGGG)_4$ linker (SEQ ID NO:27), wild type rhLL-15, a whitlow linker, and the noted (FIG. 1B "CD276-new-2", SEQ ID NO:2) anti-B71H3 sdAb was synthesized using Hi-fi DNA cloning techniques. The Biomedical Genomics Center, University of Minnesota, St. Paul, MN verified the gene sequence and the in-frame accuracy of the construct. Gene products were amplified, and the vector was transfected in Expi-293 cells. Supernatants were isolated 4-7 days later and enriched using HIS-columns in an AKTA PURE (Cytiva Sweden AB Upsala, Sweden) platform. Protein purity was determined with sodium dodecyl sulfate polyacrylamide gel electrophoresis (SDS-PAGE) stained with SIMPLYBLUE Safe Stain (Invitrogen, Carlsbad, CA).

Cancer Cell Lines

MA-148 (Geller et al., 2013. *Cytotherapy* 15(10):1297-1306) is a human epithelial high grade serous ovarian carcinoma cell line. For in vivo experiments, lines were transfected with a luciferase reporter construct using transfection reagent (LIPOFECTAMINE reagent, Invitrogen, Carlsbad, CA) and selective pressure applied with 10 μg/mL of blasticidin. Ovarian carcinoma cells OVCAR-8 (RRID: CVCL_1629) were obtained from the DTP, DCTD Tumor Repository sponsored by the Biological Testing Branch, Developmental Therapeutics Program, NCI, NIH. Other cell lines were obtained from the American Type Culture Collection including C4-2 (prostate; RRID:CVCL_4782), DU145 (prostate; RRID:CVCL_0105), LNCaP (prostate; RRID:CVCL_0395), PC-3 (prostate; RRID:CVCL_0035), A549 (lung; RRID:CVCL_0023), and NCI-H460 (lung; RRID:CVCL_0459). All lines were maintained in RPMI 1640 RPMI supplemented with 10-20% fetal bovine serum (FBS) and 2 mmol/L L-glutamine. Lines were incubated at a humidified atmosphere containing 5% $CO_2$ at a constant 37° C. When adherent cells were more than 90% confluent, they were passaged using trypsin-EDTA for detachment. For the cell counts a standard hemocytometer was used. Only those cells with a viability >95% were used for the experiments, as determined by trypan blue exclusion.

Cell Products

Peripheral blood mononuclear cells (PBMCs) were obtained from normal volunteers or subjects after consent was received and institutional review board (IRB) approval was granted, in compliance with guidelines by the Committee on the Use of Human Subjects in Research and in accordance with the Declaration of Helsinki. Cells were pelleted, lysed for red blood cells, cryopreserved in 10% DMSO/90% FBS and stored in liquid nitrogen.

Evaluation of Cytotoxicity and NK Cell Activation

Antibody-dependent cell-mediated cytotoxicity (ADCC) was measured in a flow cytometry assay by evaluating degranulation via CD107a (lysosomal-associated membrane protein LAMP-1) and intracellular IFN-γ production. Upon thawing, normal donor and subject derived PBMCs or ascites cells were rested overnight (37° C., 5% $CO_2$) in RPMI 1640 media supplemented with 10% fetal calf serum (RPMI-10). The next morning, they were and suspended with tumor target cells or media after washing twice with RPMI-10. Cells were then incubated with trispecific killer engager compounds or controls for 10 minutes at 37° C. Fluorescein isothiocyanate (FITC)-conjugated anti-human CD107a monoclonal antibody (BD Biosciences, San Jose, CA) was then added and incubated for one hour. After incubation, GOLGISTOP (1:1,500, BD Biosciences, San Jose, CA) and GOLGIPLUG (1:1,000, BD Biosciences, San Jose, CA) were added for three hours (37° C., 5% $CO_2$). After washing with phosphate buffered saline, the cells were stained with PE/Cy 7-conjugated anti-CD56 mAb, APC/Cy 7-conjugated anti-CD16 mAb, and PE-CF594-conjugated anti-CD3 mAb (BioLegend, Inc., San Diego, CA). Cells were incubated for 15 minutes at 4° C., washed, and fixed with 2% paraformaldehyde. Cells were then permeabilized using an intracellular perm buffer (BioLegend, Inc., San Diego, CA) to evaluate production of IFN-gamma (IFN-γ) through detection via aBV650 conjugated anti-human IFN-γ antibody (BioLegend, Inc., San Diego, CA). Samples were washed and the evaluated in an LSRII flow cytometer (BD Biosciences, San Jose, CA).

Real-Time Tumor Killing Assay

Tumor killing was evaluated in real-time using the INCUCYTE platform (Essen Biosciences, Inc., Ann Arbor, MI). Magnetic-bead-enriched 40,000 $CD3^{-}CD56^{+}$ NK effector cells were plated into 96-well ULA flat clear bottom polystyrene tissue-culture treated microplates (Corning, Flintshire, UK) along with GFP stably expressing OVCAR8 spheroids, 20,000 cells allowed to establish spheroids for three days prior to co-culture. Noted treatments were then added at a 30 nM concentration and the plate was placed in an INCUCYTE S3 platform (Essen Biosciences, Inc., Ann Arbor, MI) housed inside a cell incubator at 37° C./5% $CO_2$. Images from three technical replicates were taken every hour for 120 hours using a 4× objective lens and then analyzed using the INCUCYTE basic software (Essen Biosciences, Inc., Ann Arbor, MI). Graphed readouts represent integrated spheroid GFP fluorescence intensity, normalized to tumor alone at the starting (0 hr) time point.

Statistical Analysis

PRISM software (GraphPad Software, Inc., La Jolla, CA) was used to create all statistical tests. For all in vitro studies One-way ANOVA with repeated measures was used to calculate significance in comparisons to the cam1615B7H3 group. Bars represent mean±SEM. Statistical significance is displayed as *P<0.05, P<0.01, *P<0.001, and ****P<0.0001.

Example 2

A second-generation trispecific killer engager compound capable of both antibody-dependent cellular cytotoxicity (ADCC) and NK cell expansion was constructed by modifying a previously reported trispecific killer engager compound platform (Vallera et al., *Clin Cancer Res.* 2016; 22(14):3440-50. doi: 10.1158/1078-0432.CCR-15-2710. PubMed PMID: 26847056; PMCID: PMC4947440; US Patent Application Publication No. 2018/0282386 A1). In an exemplary construct, a wild-type human IL-15 crosslinker with two modified flanking regions was inserted between two antibody fragments: an N-terminal VHH humanized camelid anti-CD16 fragment and a C-terminal anti-B7H3 VHH, or single domain antibody, creating an anti-B7H3 trispecific killer engager, a schematic illustration of which is shown in FIG. 1.

To assess the ability of an exemplary anti-B7H3 protein—an sdAb—to target activity of a trispecific killer engager, an anti-B7H3 trispecific NK engager molecule was used to induce NK cell activity against B7H3-containing targets: prostate cancer cell lines, lung cancer cells lines, and ovarian cancer cell lines. Generally, trispecific NK engager molecules recruit and activate NK cells against a targeted cell population. NK activation can be measured, for example, using flow cytometric assays that measure natural killer (NK) cell degranulation (detecting $CD107a^+$ NK cells) and inflammatory cytokine production (e.g., IFN-γ).

Exemplary anti-B7H3 protein sequences were incorporated into a trispecific killer engager backbone and compared to a trispecific killer engager incorporating an anti-B7H3 scFv sequence. NK cell degranulation (measured as the percent $CD107a^+$ NK cells) and interferon gamma (IFN-γ) production (measured as the percent of IFN-$\gamma^+$ NK cells) were evaluated by flow cytometry as described in Example 1 in various cancer cell lines, and in the presence of various concentration of trispecific killer engager. Briefly, the trispecific killer engager compounds were incubated for five hours before NK cell degranulation and inflammatory cytokine production (IFN-γ) was measured by flow cytometry. The results presented reflect the average of N=3 independent experiments.

Figure 2B:
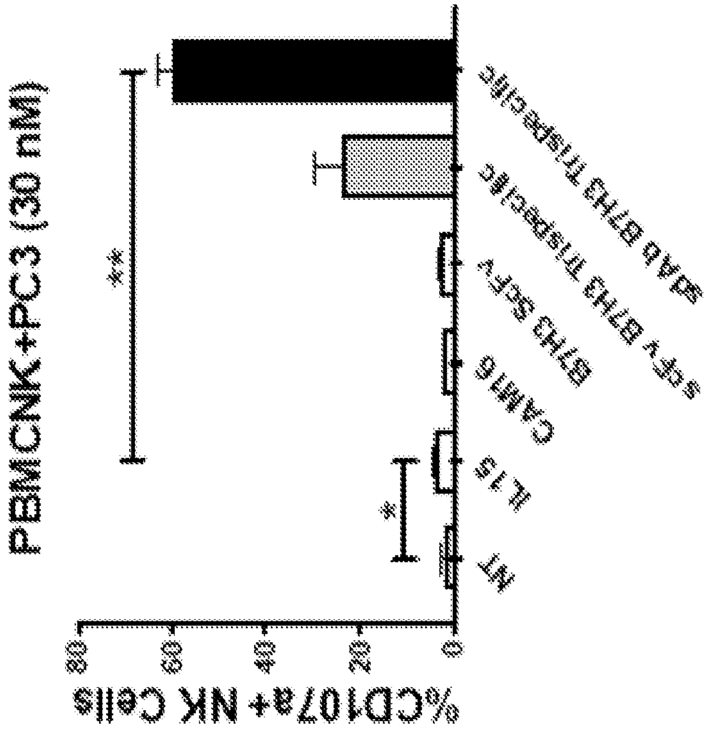
FIGS. 2A-2F illustrate NK cell degranulation and interferon gamma (IFN-7) production measured by flow cytometry.
Figure 2A:
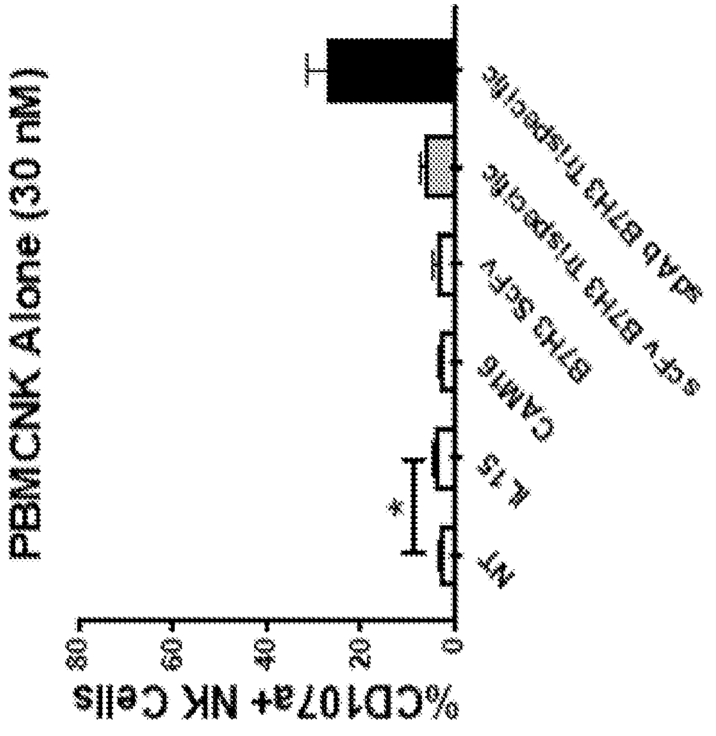
Figure 2D:
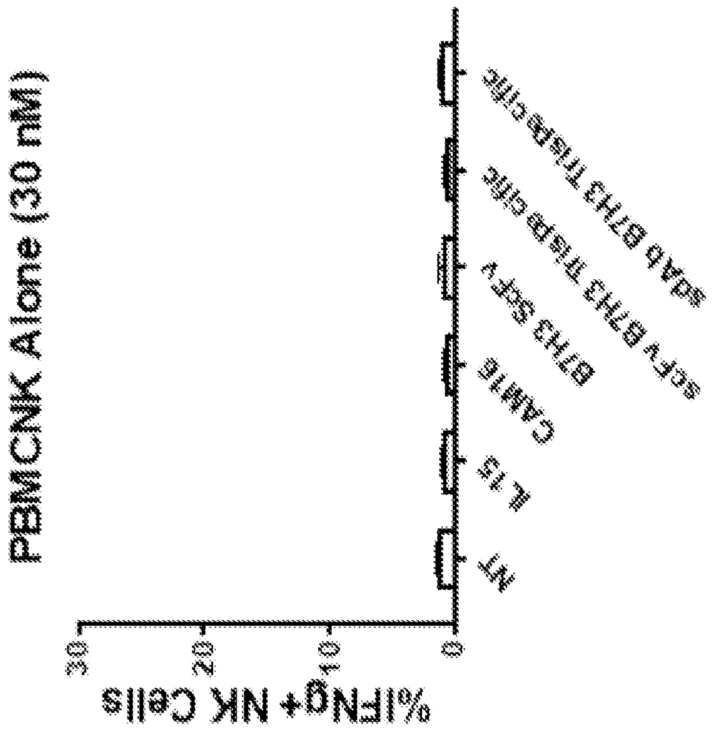
Figure 2C:
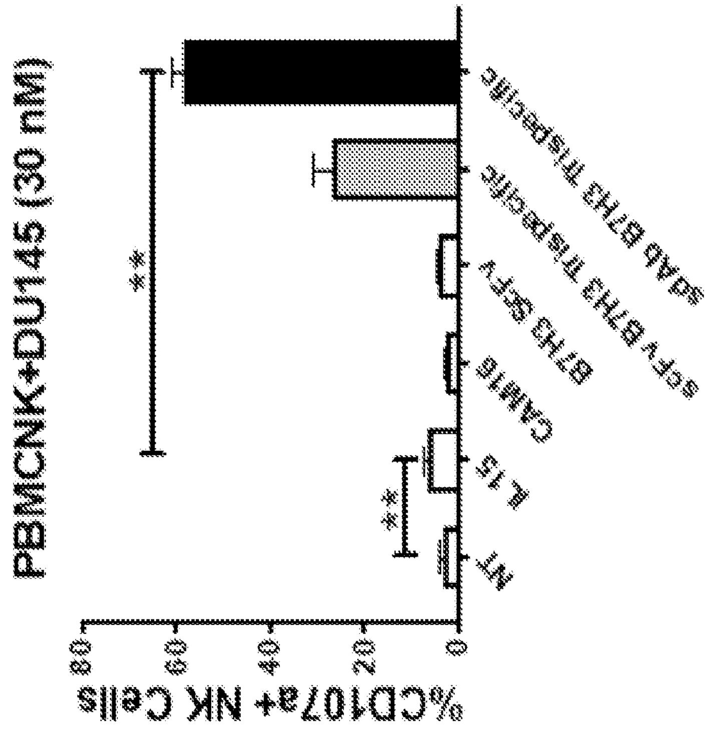
Figure 2E:
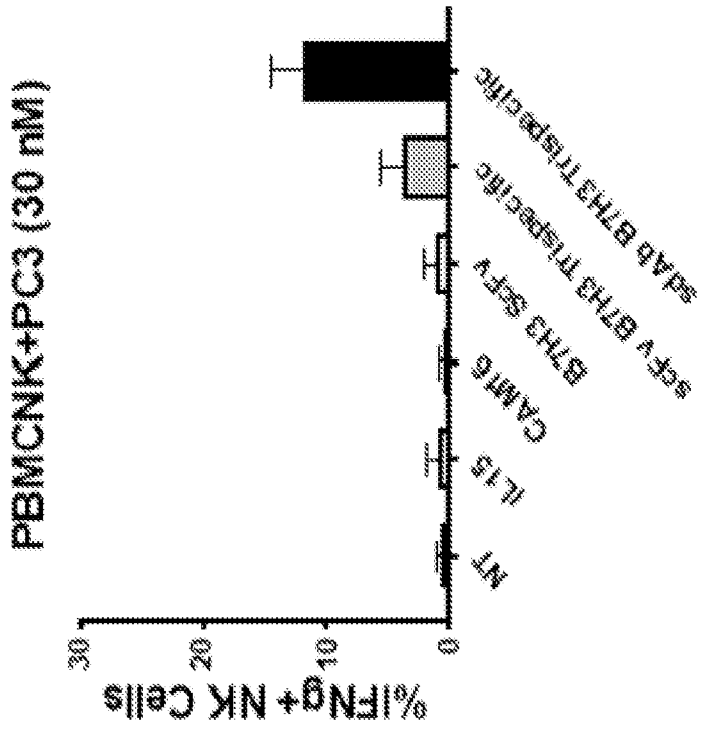
Figure 2F:
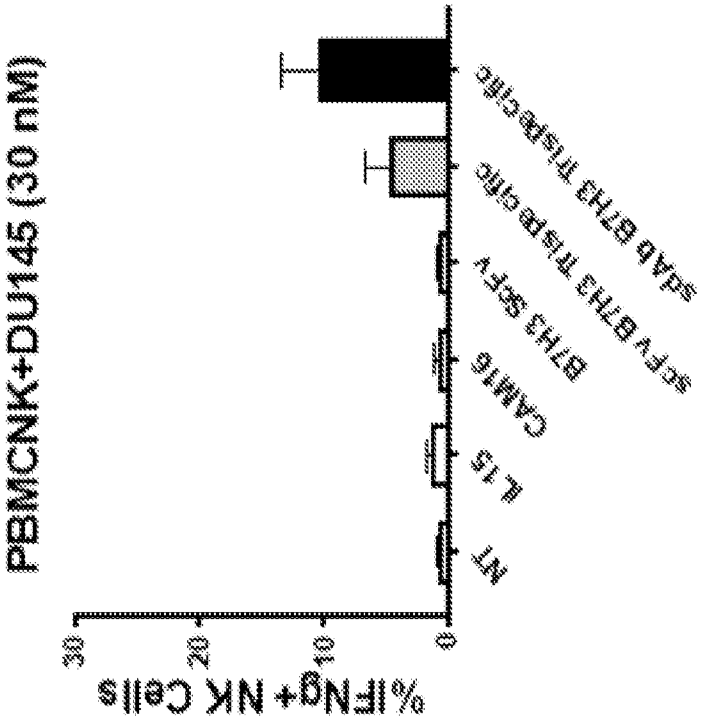
Figure 3B:
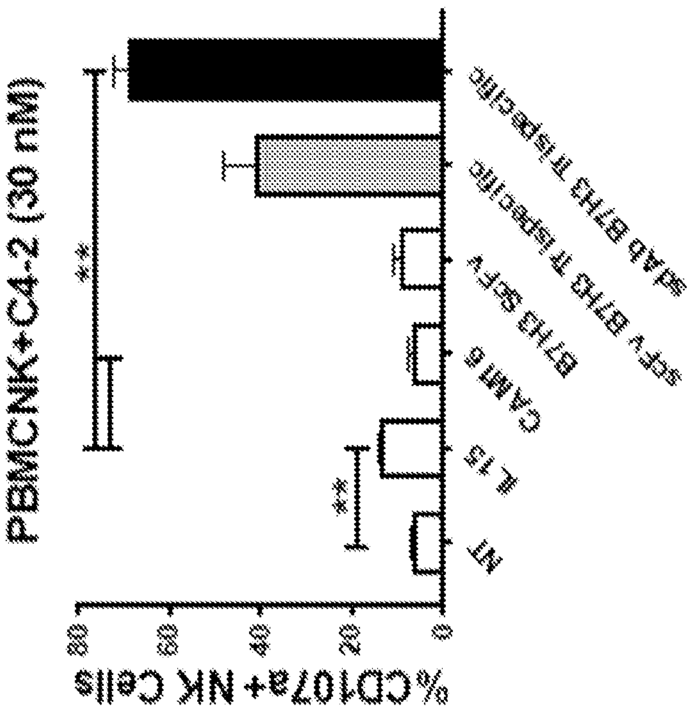
FIGS. 3A-3D illustrate NK cell degranulation and IFN-γ production measured by flow cytometry.
Figure 3A:
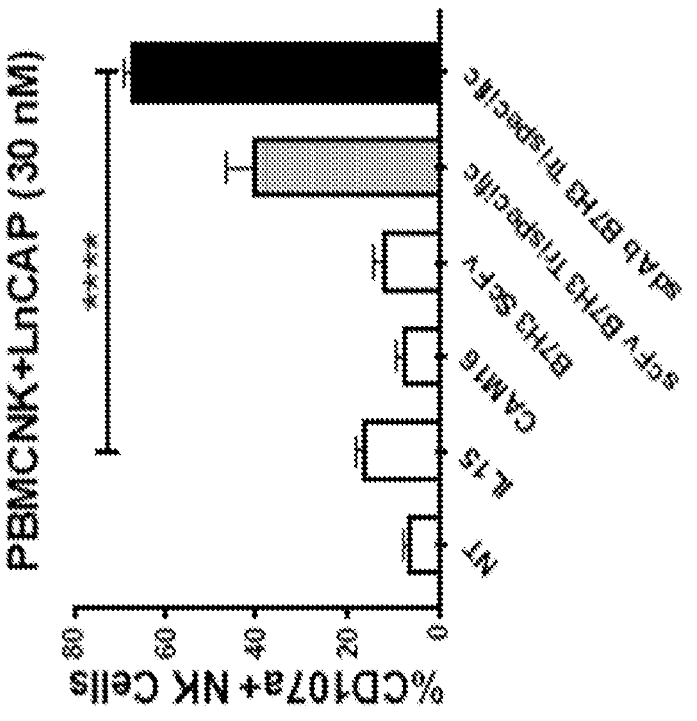
Figure 3C:
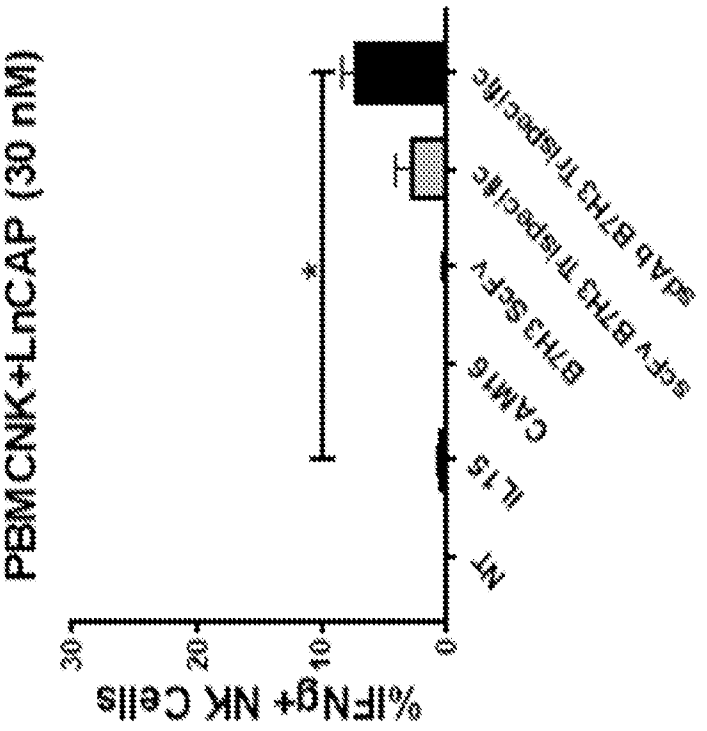
Figure 3D:
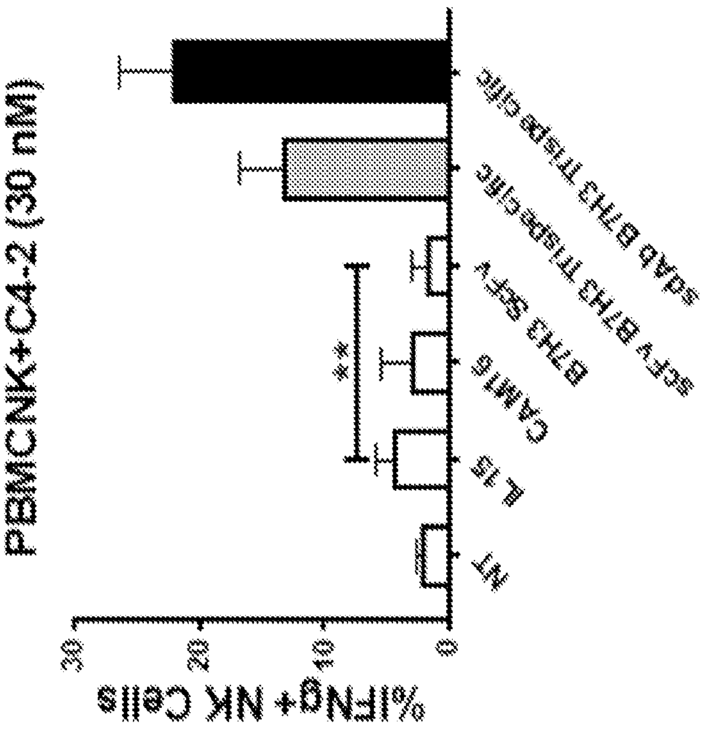

The exemplary anti-B7H3 proteins incorporated into trispecific killer engager molecules enhanced NK cell degranulation and IFN-γ production against prostate cancer cells, as demonstrated in PC3 and DU145 cells (see FIGS. 2B, 2C, 2E and 2F), and LnCAP and C4-2 cells (see FIGS. 3A, 3B, 3C and 3D), when co-cultured with peripheral blood mononuclear cells (PBMCs) at a 30 nM concentration; as compared to PBMCs incubated alone (see FIGS. 2A and 2D).

FIG. 2 and FIG. 3 provide data showing that trispecific NK engager molecules containing an exemplary anti-B7H3 sdAb protein induces activity of the NK cells against a B7H3-expressing target cell population. The anti-B7H3 trispecific NK engagers induced NK cell degranulation and NK cell inflammatory cytokine production against multiple prostate cancer cells lines. For both measurements of NK activation, the sdAb-containing trispecific NK engager (black bars) induced greater responses than an anti-B7H3 trispecific NK engager molecule containing an anti-B7H3 scFv (gray bars).

Figure 4B:
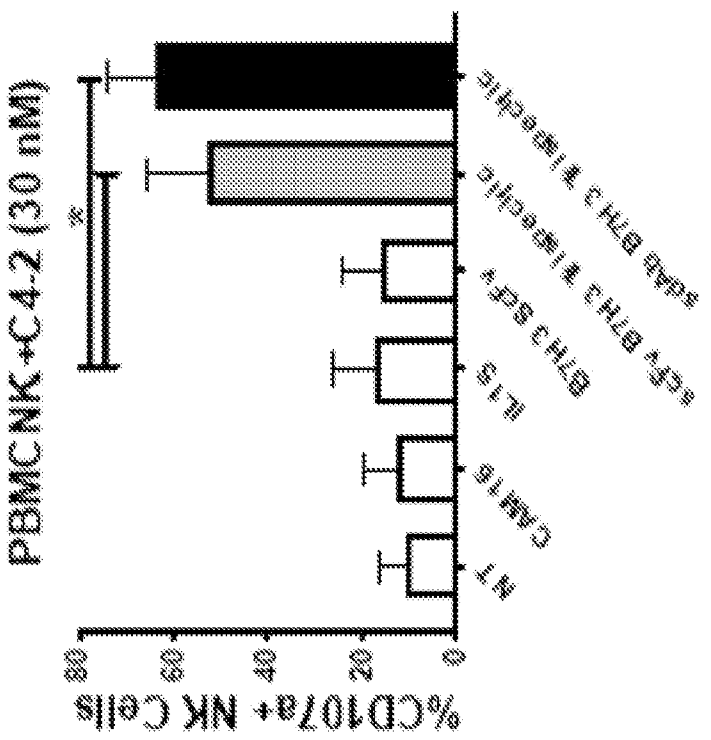
FIGS. 4A-4F illustrate NK cell degranulation and IFN-γ production measured by flow cytometry.
Figure 4A:
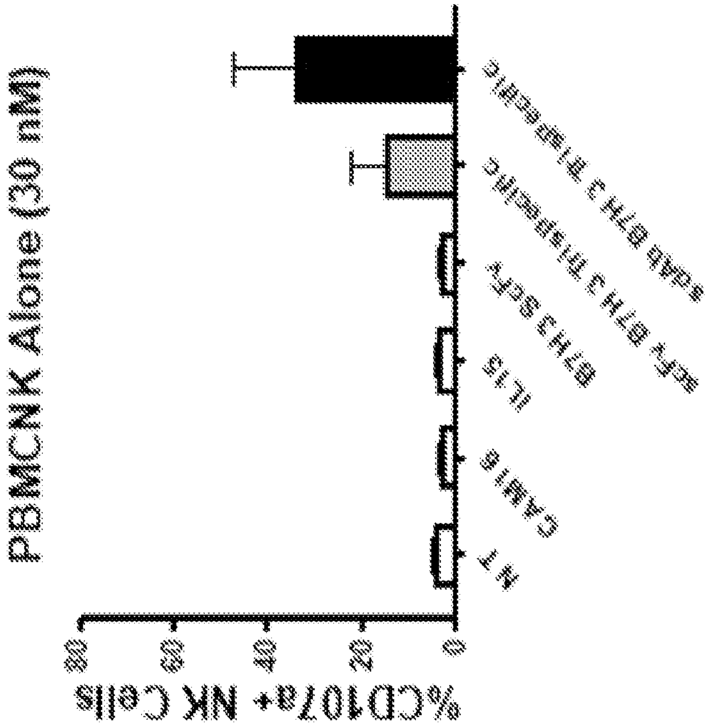
Figure 4D:
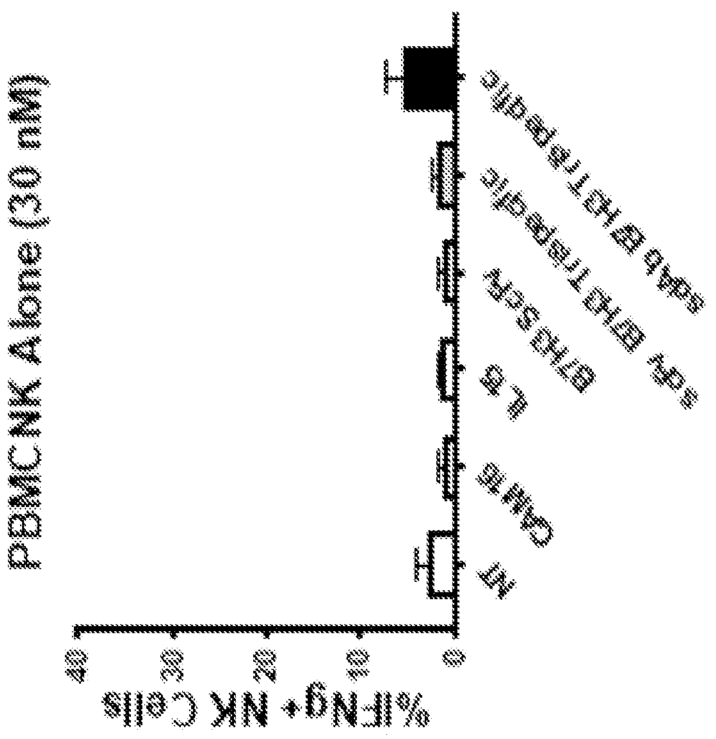
Figure 4C:
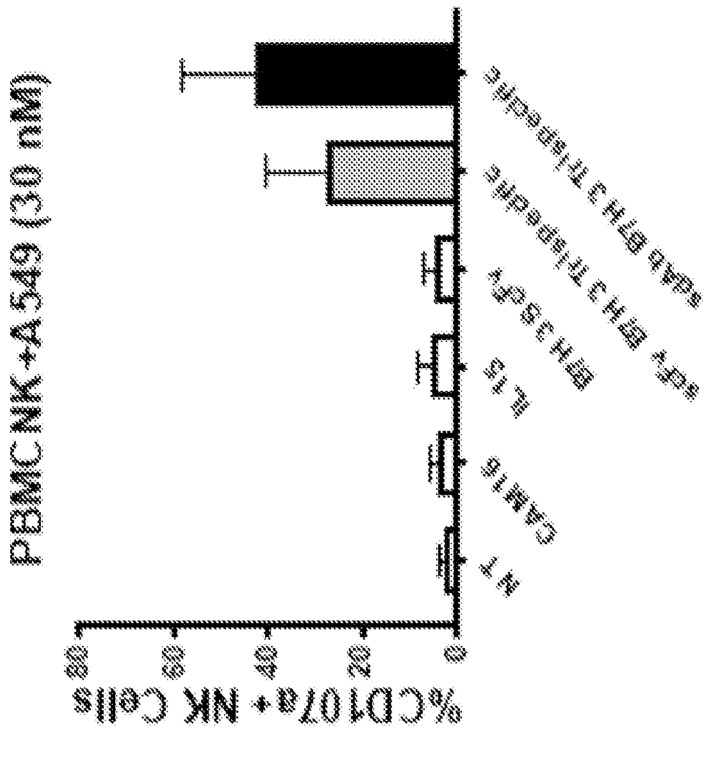
Figure 4E:
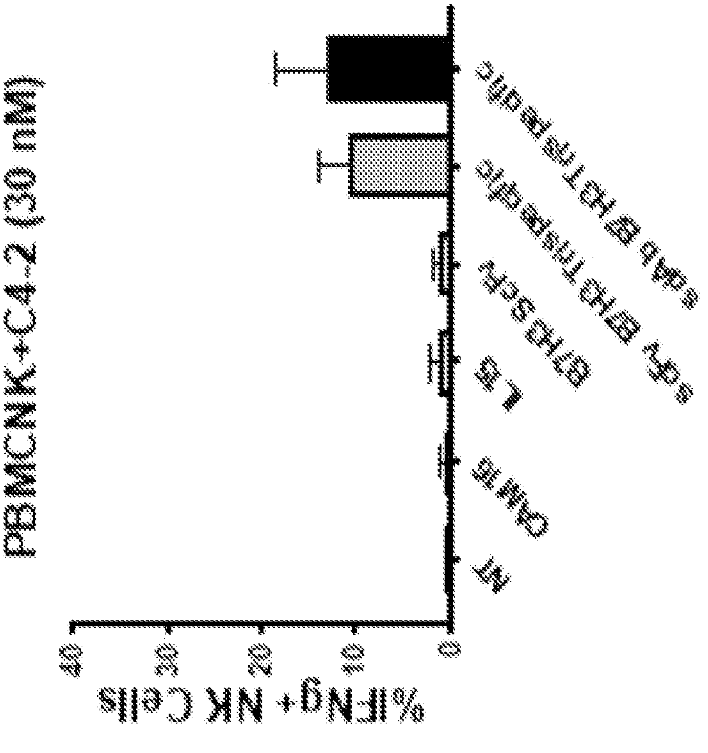
Figure 4F:
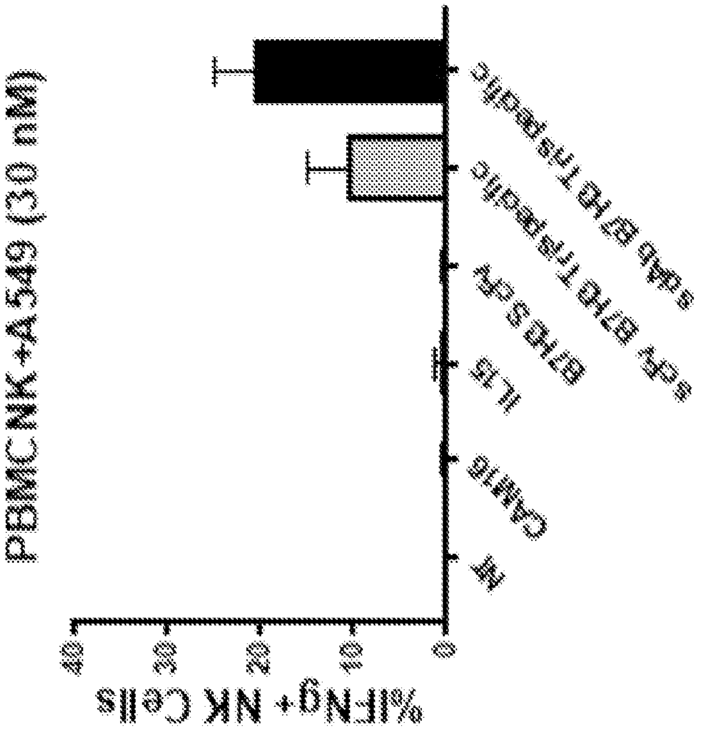
Figure 5A:
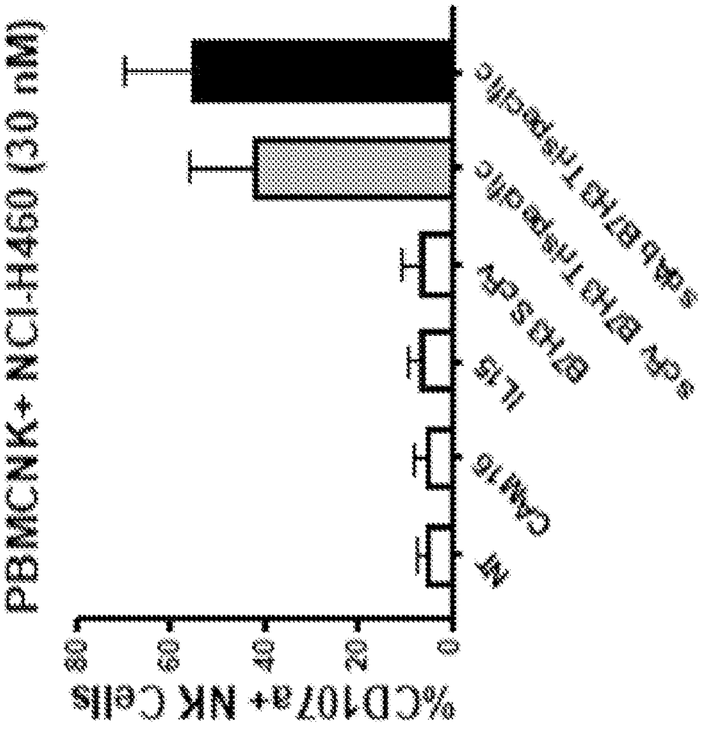
FIGS. 5A-5F illustrate NK cell degranulation and IFN-γ production measured by flow cytometry.
Figure 5B:
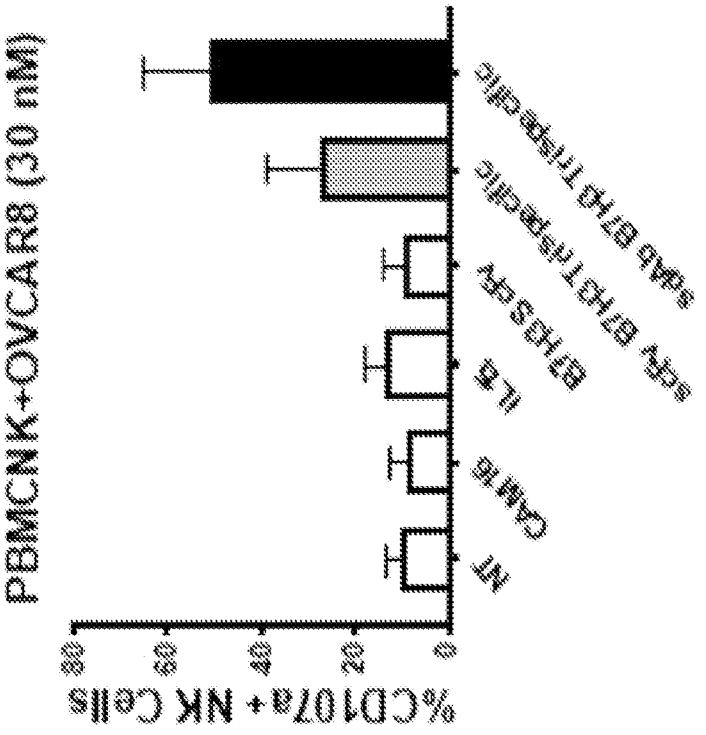
Figure 5D:
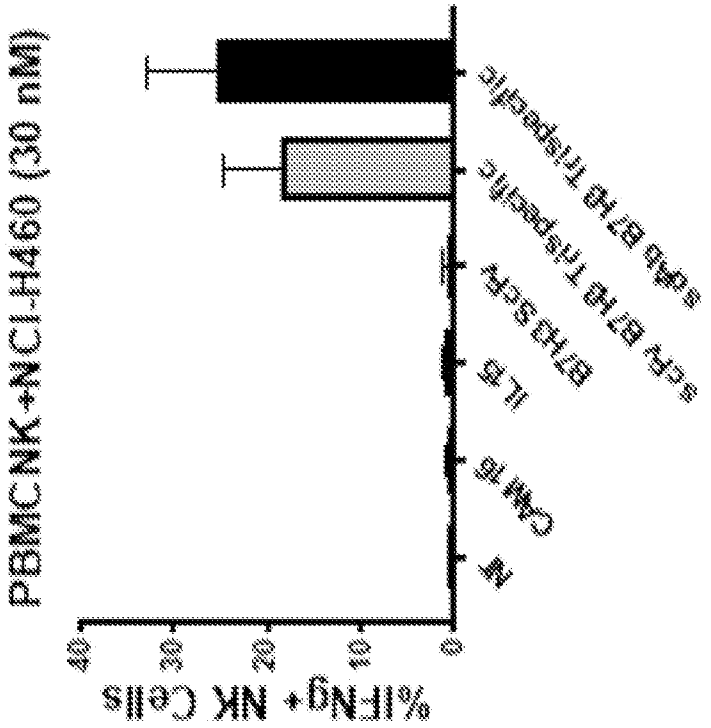
Figure 5C:
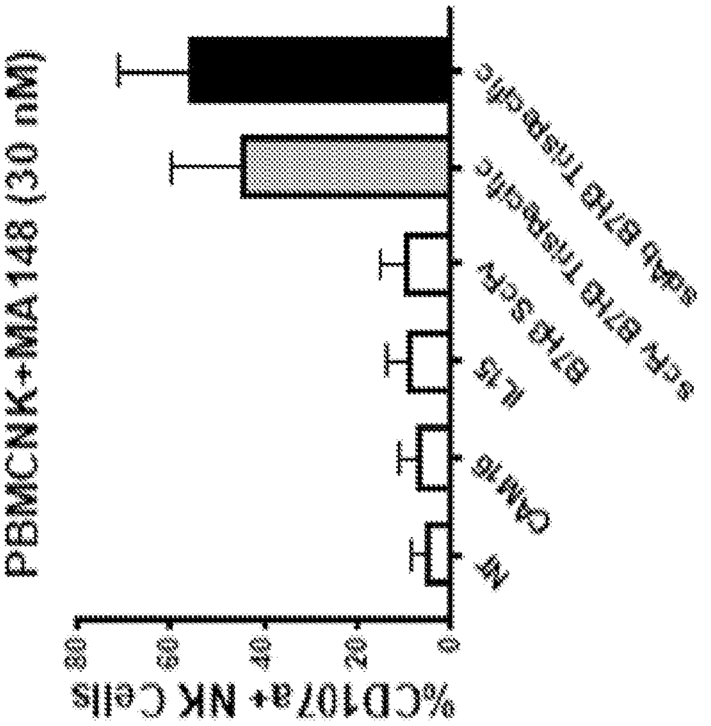
Figure 5F:
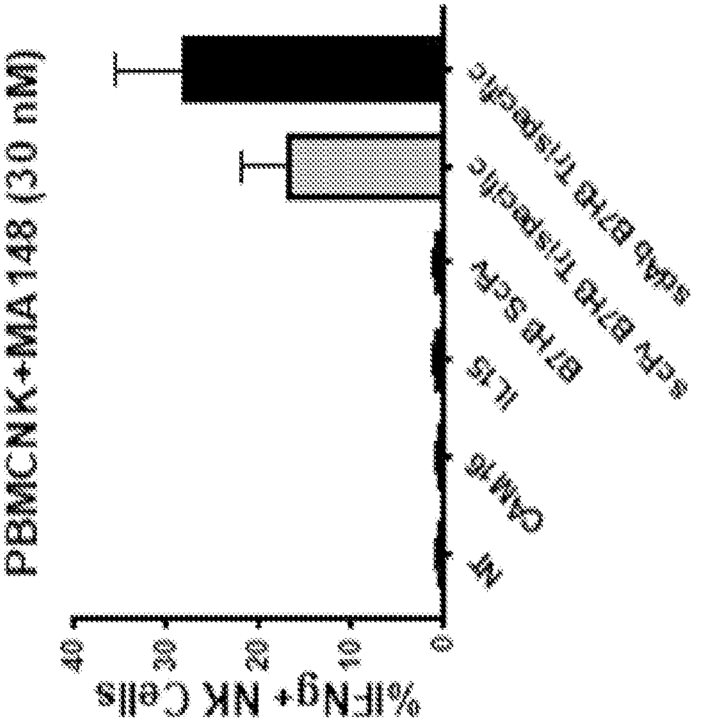
Figure 5E:
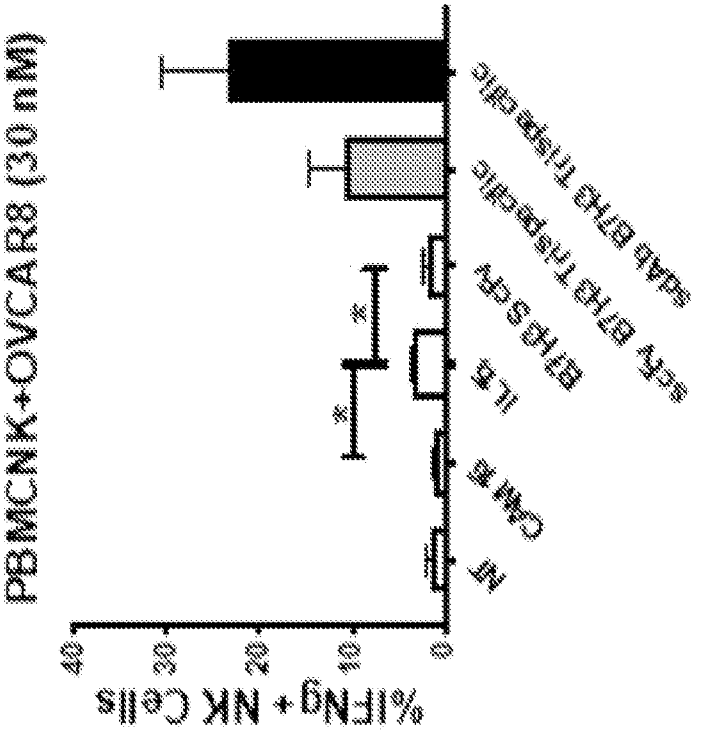

The exemplary anti-B7H3 proteins incorporated into trispecific killer engager molecules also enhanced NK cell degranulation and IFN-γ production against lung cancer cells, as demonstrated in A549 and NCI-H460 cells (see FIGS. 4C, 4F, 5A and 5D), and ovarian cancer cells, as demonstrated in OVCAR8 and MA148 (see FIGS. 5B, 5C, 5E and 5F) cells, when co-cultured with PBMCs at a 30 nM concentration; as compared to PBMCs incubated alone (see FIGS. 4A and 4D) or co-cultured with C4-2 cells (see FIGS. 4B and 4E).

FIG. 4 and FIG. 5 provide data showing that trispecific NK engager molecules containing an exemplary anti-B7H3 sdAb protein induces activity of the NK cells against additional B7H3-expressing target cell populations: prostate cancer cell line C4-2, lung cancer cell lines A549 and NCI-H460, and ovarian cancer cell lines OVCAR8 and MA148. Once again, the sdAb-containing trispecific NK engager (black bars) induced greater responses than an anti-B7H3 trispecific NK engager molecule containing an anti-B7H3 scFv (gray bars).

Figure 6A:
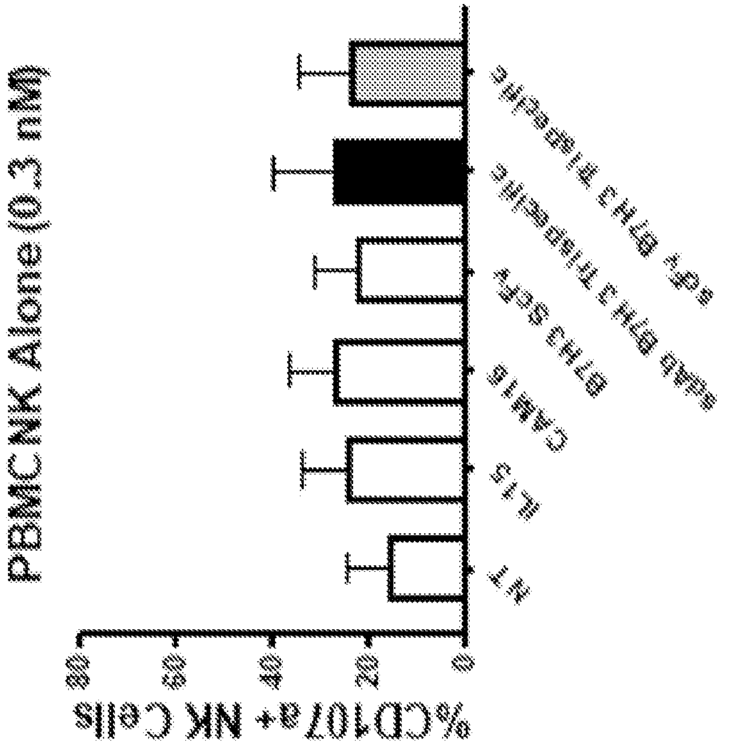
FIGS. 6A-6F illustrate NK cell degranulation measured by flow cytometry.
Figure 6B:
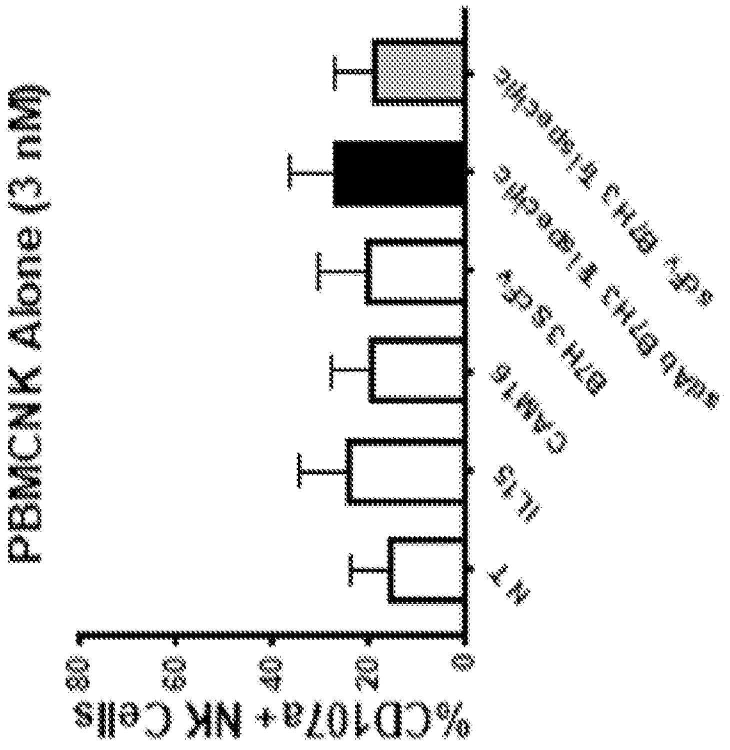
Figure 6D:
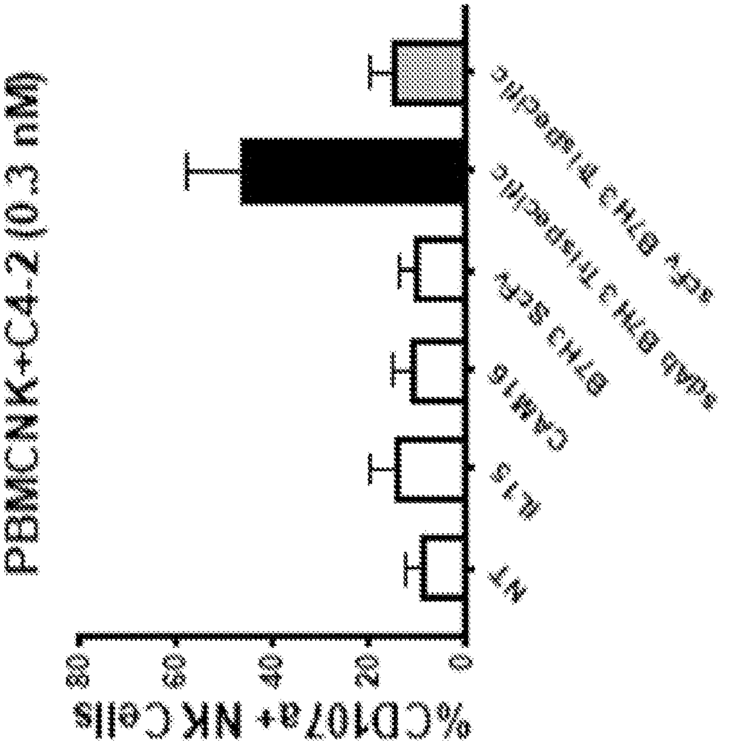
Figure 6C:
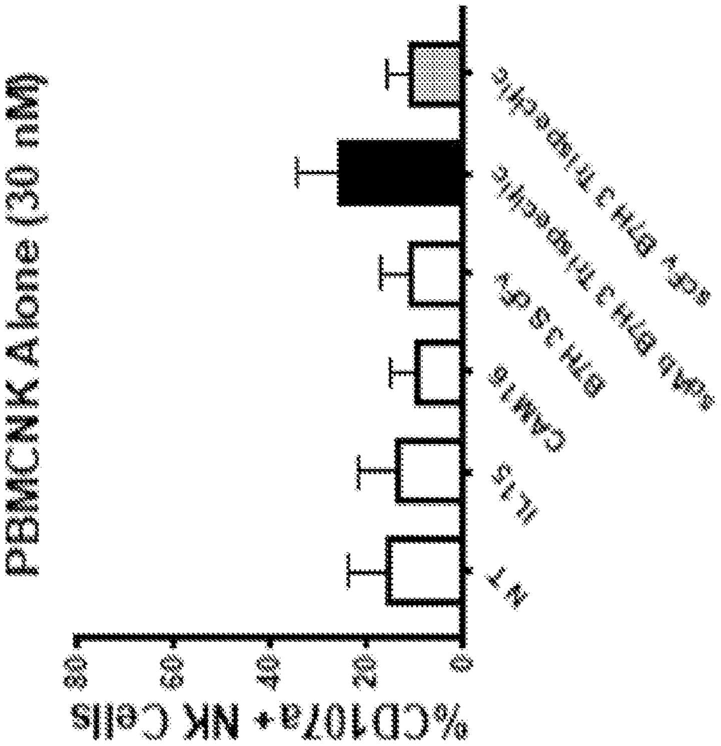
Figure 6F:
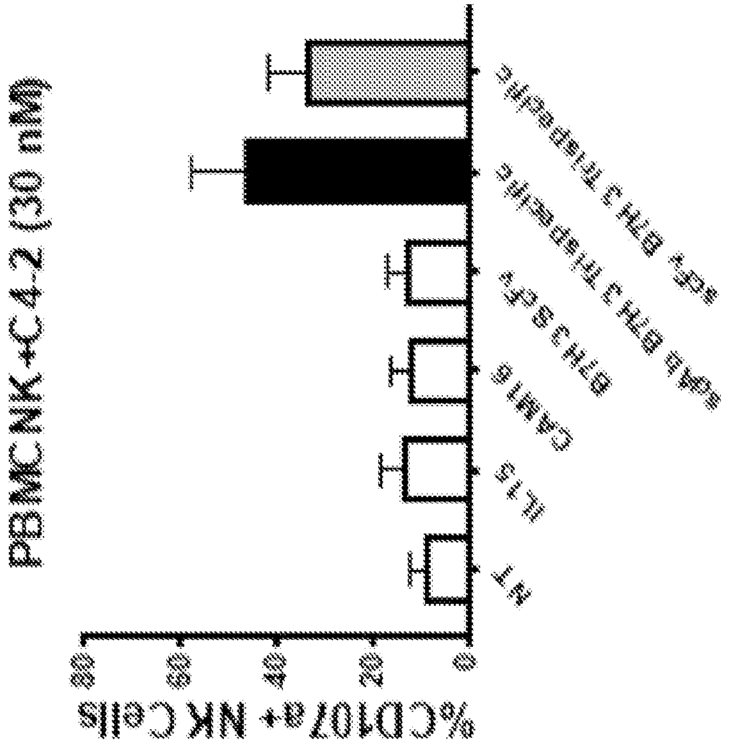
Figure 6E:
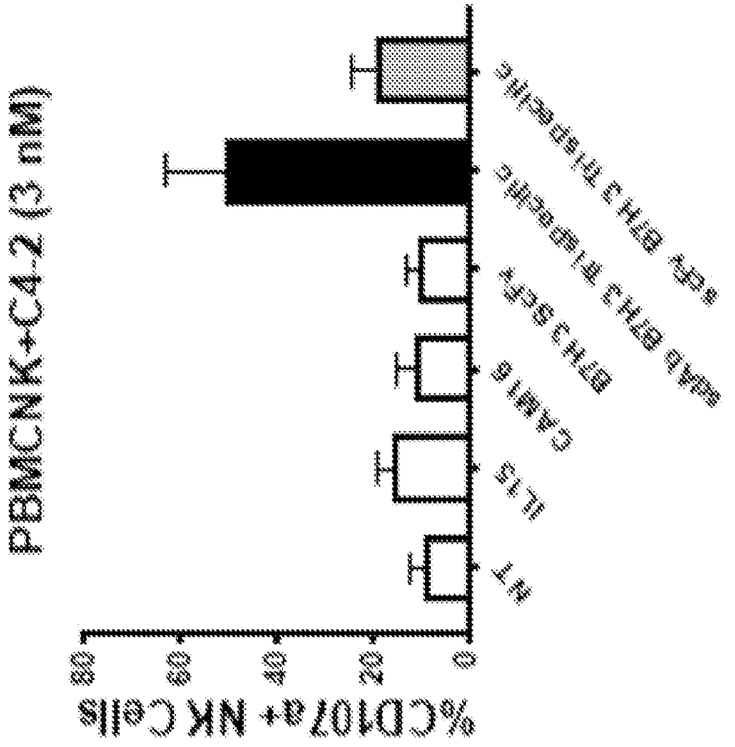

The exemplary anti-B7H3 proteins incorporated into trispecific killer engager molecules were demonstrated to enhance NK cell degranulation against prostate cancer, at three of the doses tested: 0.3; 3 and 30 nM (see FIGS. 6D, 6E and 6F) as compared to the absence of effect when incubated with PBMCs alone, independently of the dose (see FIGS. 6A, 6B and 6C).

Figure 7B:
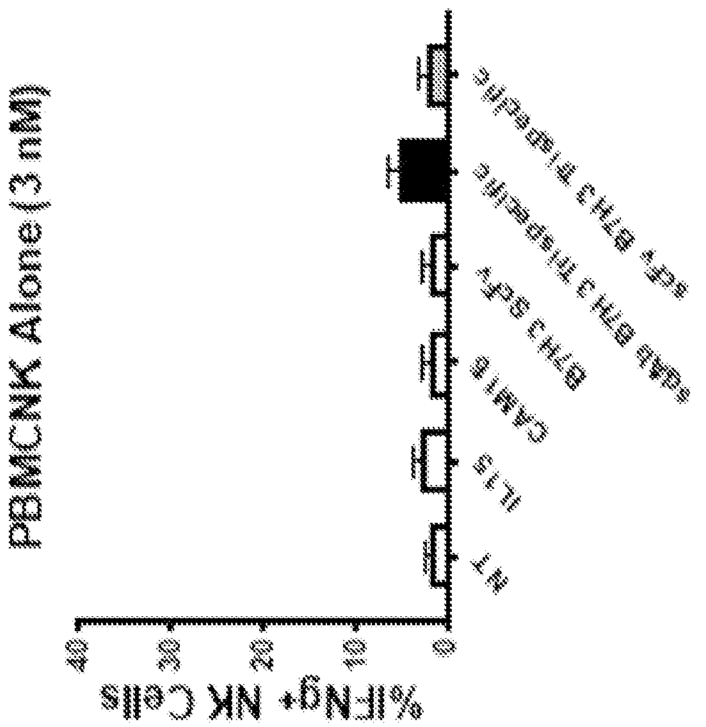
FIGS. 7A-7F illustrate IFN-γ production measured by flow cytometry.
Figure 7A:
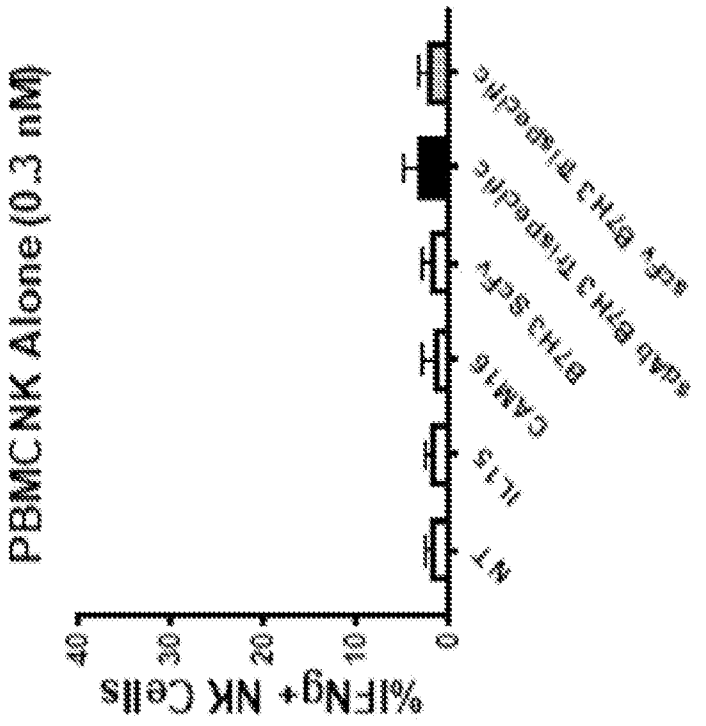
Figure 7D:
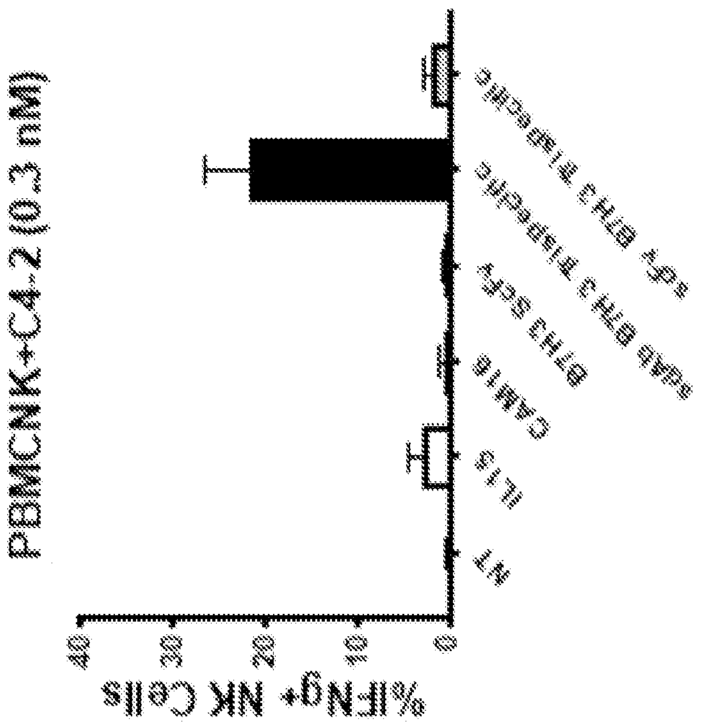
Figure 7C:
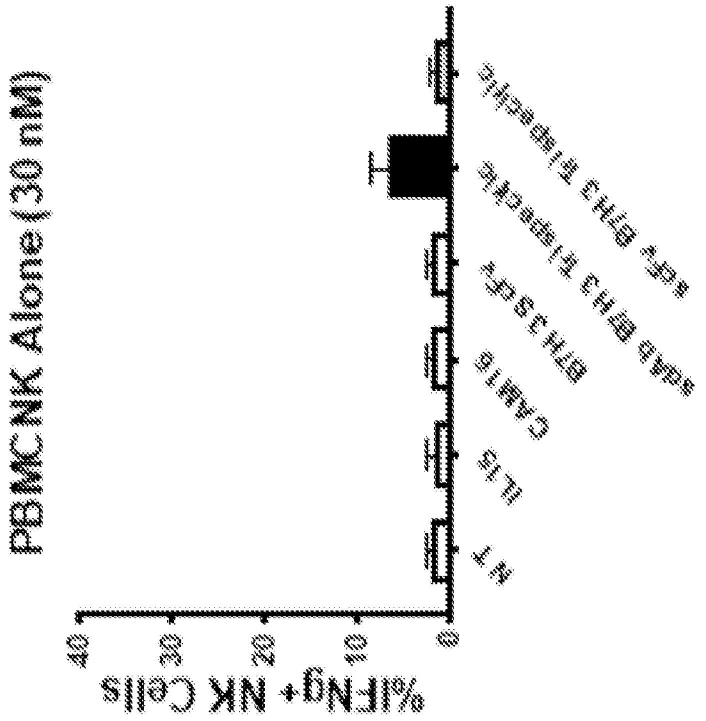
Figure 7F:
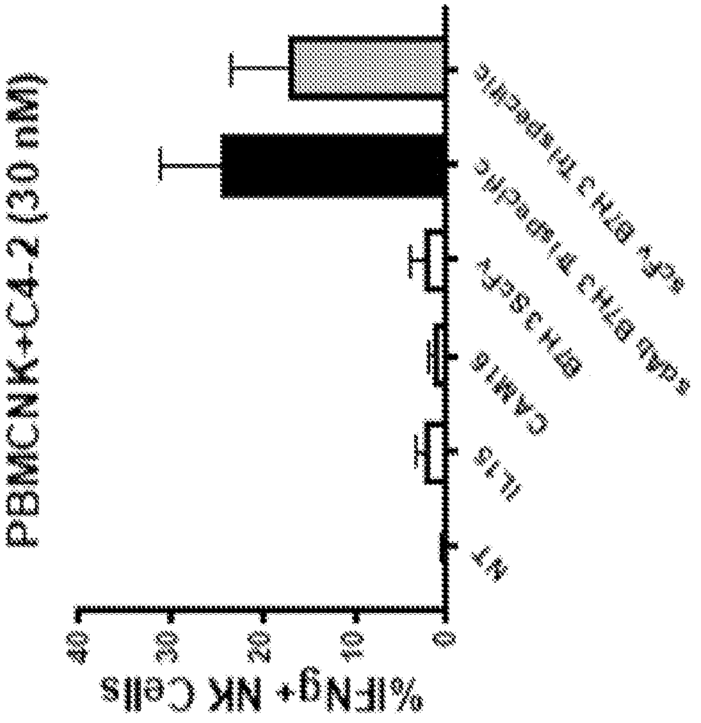
Figure 7E:
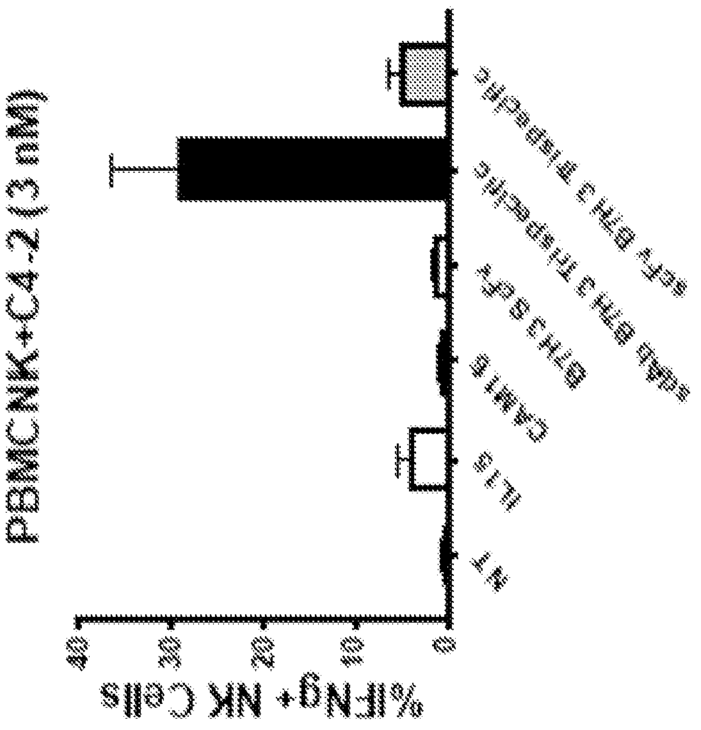

Similar effects were observed when IFN-γ production was assessed; the exemplary anti-B7H3 proteins incorporated into trispecific killer engager molecules enhanced IFN-γ production against prostate cancer, at the three doses tested: 0.3; 3 and 30 nM (see FIGS. 7D, 7E and 7F) as compared to the absence of effect when incubated with PBMCs alone, independently of the dose (see FIGS. 7A, 7B and 7C).

FIG. 6 and FIG. 7 provide data showing that trispecific NK engager activity is target dependent. Background NK activity is low in the absence of B7H3-expressing target cells. NK cell degranulation and IFN-γ production are induced when B7H3-expressing target cells are co-cultured with PBMC NK cells and anti-B7H3-containing trispecific engager molecules. Once again, the sdAb-containing trispecific NK engager (black bars) induced greater responses than an anti-B7H3 trispecific NK engager molecule containing an anti-B7H3 scFv (gray bars).

Figure 8:
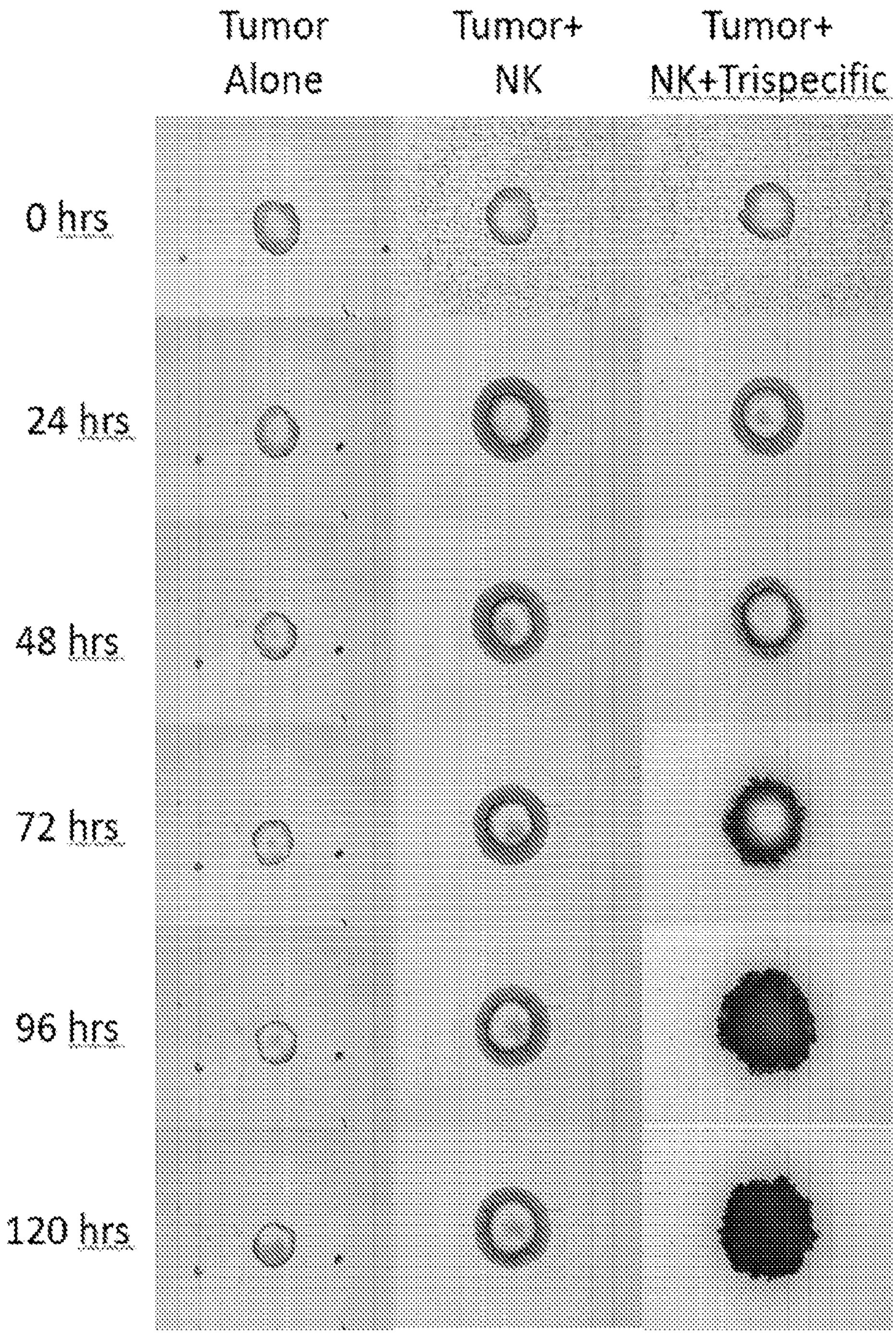
FIG. 8 shows photographs illustrating the enhancement by trispecific killer engager incorporating exemplary anti-B7H3 protein of cytolytic activity against ovarian cancer spheroids.

The ability of the trispecific killer engager incorporating exemplary anti-B7H3 protein to enhance cytolytic activity against ovarian cancer spheroids was then assessed in vitro, as described in Example 1. Briefly, an exemplary anti-B7H3 protein was incorporated into a trispecific killer engager backbone and its activity was compared to the activity of NK cells alone in a spheroid assay. 20,000 GFP-expressing OVCAR8 cells were plated in a well of a 96-well ULA plate and allowed to form for three days. 40,000 enriched NK cells were then added, either alone or with 30 nM trispecific killer engager. Pictures showing GFP intensity measurements were taken every hour for 120 hours. It is to be noted that cellular death induces a temporary increase in green fluorescence. Three technical replicates for each of the three biologic replicates were performed. As shown in FIG. 8, and as further quantified in FIG. 9, the trispecific killer engager incorporating exemplary anti-B7H3 protein enhanced cytolytic activity against ovarian cancer spheroids. As compared to the activity of NK cells alone.

Figure 9:
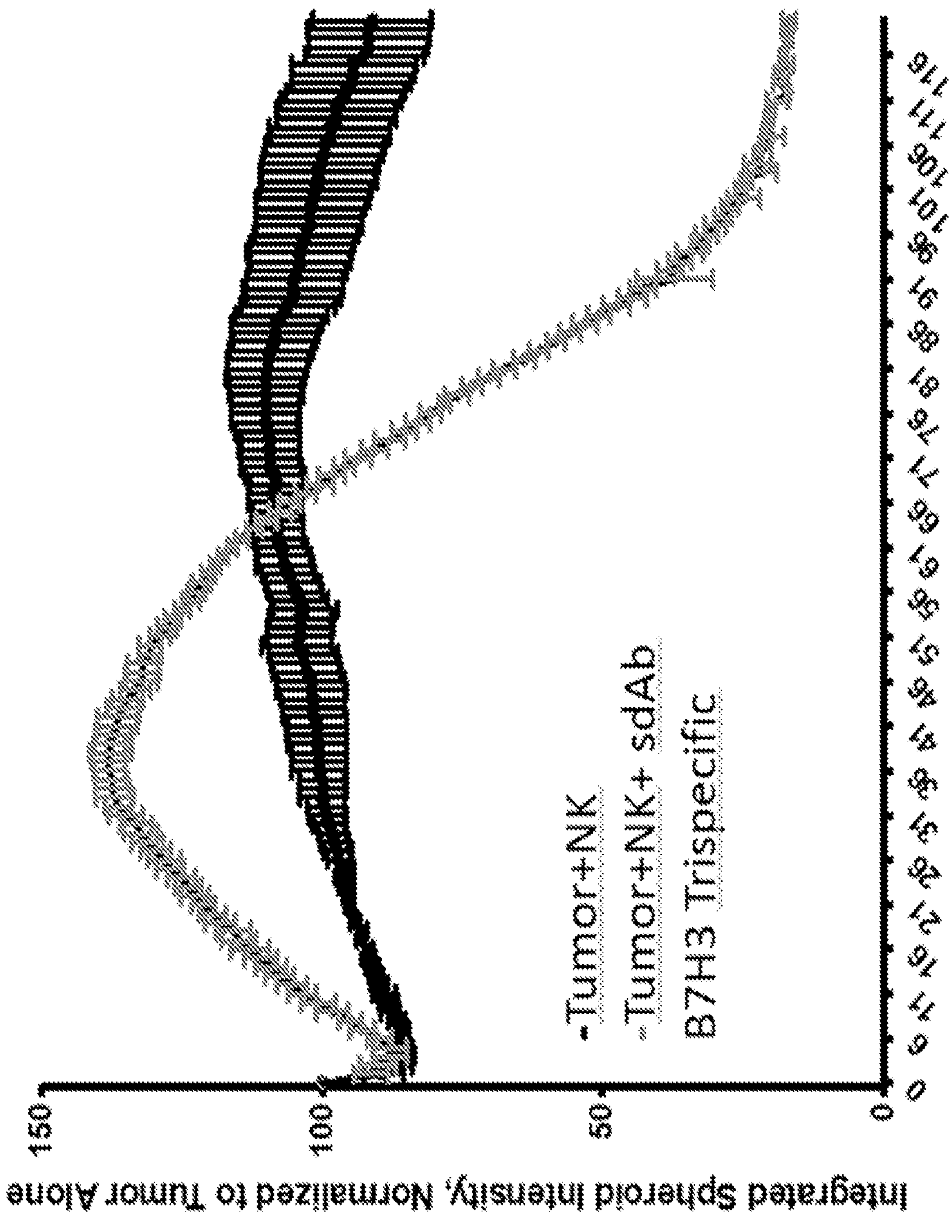
FIG. 9 is a graph illustrating the quantification of the enhancement by trispecific killer engager incorporating exemplary anti-B7H3 protein of cytolytic activity against ovarian cancer spheroids.

FIG. 8 and FIG. 9 provide data showing the ability of the anti-B7H3-sdAb-contining trispecific NK engager to kill ovarian cancer cells, using an advanced imaging based cytolytic assay. In this assay, 20,000 OVCAR8 ovarian cancer cells were stably transduced with a GFP cassette (to provide green fluorescence), then plated in an ultra-low adhesion (ULA) 96-well plate to allow spheroids to form over a three-day period. After three days, nothing (Tumor Alone), 40,000 NK cells with a small amount of cytokine to maintain survival (Tumor+NK), or 40,000 NK cells and 30 nM trispecific NK engager containing an anti-B7H3 sdAb are added. Spheroid killing, measured as loss of spheroid green-fluorescence intensity, is observed over a five-day (120 hours) period. When treated with the trispecific NK engager molecule containing the anti-B7H3 sdAb, the NK cells kill the spheroid much better than when no trispecific is present, showing that this trispecific can induce killing of three-dimensional tumor formations.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless defined otherwise, all technical and scientific terms used herein have the same meaning as commonly understood by one of ordinary skill in the art to which this invention belongs.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

Although the invention has been described with reference to the above examples, it will be understood that modifications and variations are encompassed within the spirit and scope of the invention. Accordingly, the invention is limited only by the following claims.

Sequence Listing Free Text

SEQ ID NO:1
HVQLVESGGG LVQPGRSLRL SCAASGFTFS SYWMYWVRQT PGKGLEWVST INRDGSATWY ADSVKGRFTI SRDNAKNTGY LQMNSLEPDD TAVYYCVSDP DNYSSDEMVP YWGQGTQVTV SS

SEQ ID NO:2
QVQLVESGGG LVQPGGSLRL SCAASGFTFS SYWMYWVRQT PGKGLEWVST INRDGSATWY ADSVKGRFTI SRDNAKNTGY LQMNSLKPDD TAVYYCVSDP DNYSSDEMVP YWGQGTQVTV SS

SEQ ID NO:3
XVQLVESGGG LVQPGXSLRL SCAASGFTFS SYWMYWVRQT PGKGLEWVST INRDGSATWY ADSVKGRFTI SRDNAKNTGY LQMNSLXPDD TAVYYCVSDP DNYSSDEMVP YWGQGTQVTV SS

SEQ ID NO:4
SYWMY

SEQ ID NO:5
INRDGSATWY ADSVKGRFT

SEQ ID NO:6
DPDNYSSDEM VPY

SEQ ID NO:7
MKWVTFISLL FLFSSAYS

SEQ ID NO:8
VDEHHHHHHH HHH

SEQ ID NO:9
MKWVTFISLL FLFSSAYSHV QLVESGGGLV QPGRSLRLSC AASGFTFSSY WMYWVRQTPG KGLEWVSTIN RDGSATWYAD SVKGRFTISR DNAKNTGYLQ MNSLEPDDTA VYYCVSDPDN YSSDEMVPYW GQGTQVTVSS VDEHHHHHHH HHH

SEQ ID NO:10
MKWVTFISLL FLFSSAYSQV QLVESGGGLV QPGGSLRLSC AASGFTFSSY WMYWVRQTPG KGLEWVSTIN RDGSATWYAD SVKGRFTISR DNAKNTGYLQ MNSLKPDDTA VYYCVSDPDN YSSDEMVPYW GQGTQVTVSS VDEHHHHHHH HHH

SEQ ID NO:11
NWVNVISDLK KIEDLIQSMH IDATLYTESD VHPSCKVTAM KCFLLELQVI SLESGDASIH DTVENLIILA NNSLSSNGNV TESGCKECEE LEEKNIKEFL QSFVHIVQMF INTS

SEQ ID NO:12
PSGQAGAAM S ESLFVSNHAY

SEQ ID NO: 13
EASGGP E

SEQ ID NO: 14
SGGGGSGGGG SGGGGSGGGG
SEQ ID NO:15
GSTSGSGKPG SGEGSTKG
SEQ ID NO:16
EPKSSDKTHT SPPSPEL
SEQ ID NO:17
RATPSHNSHQ VPSAGGPTAN SGTSG
SEQ ID NO:18
SSGGGGSGGG GGGSSRSSL
SEQ ID NO:19
QVQLVESGGG LVQPGGSLRL SCAASGLTFS SYNMGWFRQA PGQGLEAVAS ITWSGRDTFY ADSVKGRFTI SRDNSKNTLY LQMNSLRAED TAVYYCAANP WPVAAPRSGT YWGQGTLVTV SS
CDR1: amino acids 31-35
CDR2: amino acids 51-69
CDR3: amino acids 97-111
SEQ ID NO:20
MKWVTFISLL FLFSSAYSQV QLVESGGGLV QPGGSLRLSC AASGLTFSSY NMGWFRQAPG QGLEAVASIT WSGRDTFYAD SVKGRFTISR DNSKNTLYLQ MNSLRAEDTA VYYCAANPWP VAAPRSGTYW GQGTLVTVSS SGGGGSGGGG SGGGGSGGGG SGHVQLVESG GGLVQPGRSL RLSCAASGFT FSSYWMYWVR QTPGKGLEWV STINRDGSAT WYADSVKGRF TISRDNAKNT GYLQMNSLEP DDTAVYYCVS DPDNYSSDEM VPYWGQGTQV TVSSVDEHHH HHHHHHH
Amino acids 1-18: leader
Amino acids 19-140: humanized camCD16
Amino acids 141-162: linker
Amino Acids 163-284: anti-B7H3 clone 1
Amino acids 285-297: VDE linker, 10× His tag
SEQ ID NO:21
MKWVTFISLL FLFSSAYSQV QLVESGGGLV QPGGSLRLSC AASGLTFSSY NMGWFRQAPG QGLEAVASIT WSGRDTFYAD SVKGRFTISR DNSKNTLYLQ MNSLRAEDTA VYYCAANPWP VAAPRSGTYW GQGTLVTVSS SGGGGSGGGG SGGGGSGGGG SGQVQLVESG GGLVQPGGSL RLSCAASGFT FSSYWMYWVR QTPGKGLEWV STINRDGSAT WYADSVKGRF TISRDNAKNT GYLQMNSLKP DDTAVYYCVS DPDNYSSDEM VPYWGQGTQV TVSSVDEHHH HHHHHHH
Amino acids 1-18: leader
Amino acids 19-140: humanized camCD16
Amino acids 141-162: linker
Amino Acids 163-284: anti-B7H3 clone 2
Amino acids 285-297: VDE linker, 10× His tag
SEQ ID NO:22
QVQLVESGGG LVQPGGSLRL SCAASGLTFS SYNMGWFRQA PGQGLEAVAS ITWSGRDTFY ADSVKGRFTI SRDNSKNTLY LQMNSLRAED TAVYYCAANP WPVAAPRSGT YWGQGTLVTV SSSGGGGSGG GGSGGGGSGG GGSGNWVNVI SDLKKIEDLI QSMHIDATLY TESDVHPSCK VTAMKCFLLE LQVISLESGD ASIHDTVENL IILANNSLSS NGNVTESGCK ECEELEEKNI KEFLQSFVHI VQMFINTSGS TSGSGKPGSG EGSTKGHVQL VESGGGLVQP GRSLRLSCAA SGFTFSSYWM YWVRQTPGKG LEWVSTINRD GSATWYADSV KGRFTISRDN AKNTGYLQMN SLEPDDTAVY YCVSDPDNYS SDEMVPYWGQ GTQVTVSS
Amino acids 1-122: humanized camCD16
Amino acids 123-142: linker
Amino acids 143-258: IL-15 fragment
Amino acids 259-276: linker
Amino acids 277-498: camB7H3 clone 1
SEQ ID NO:23
QVQLVESGGG LVQPGGSLRL SCAASGLTFS SYNMGWFRQA PGQGLEAVAS ITWSGRDTFY ADSVKGRFTI SRDNSKNTLY LQMNSLRAED TAVYYCAANP WPVAAPRSGT YWGQGTLVTV SSSGGGGSGG GGSGGGGSGG GGSGNWVNVI SDLKKIEDLI QSMHIDATLY TESDVHPSCK VTAMKCFLLE LQVISLESGD ASIHDTVENL IILANNSLSS NGNVTESGCK ECEELEEKNI KEFLQSFVHI VQMFINTSGS TSGSGKPGSG EGSTKGQVQL VESGGGLVQP GGSLRLSCAA SGFTFSSYWM YWVRQTPGKG LEWVSTINRD GSATWYADSV KGRFTISRDN AKNTGYLQMN SLKPDDTAVY YCVSDPDNYS SDEMVPYWGQ GTQVTVSS
Amino acids 1-122: humanized camCD16
Amino acids 123-142: linker
Amino acids 143-258: IL-15 fragment
Amino acids 259-276: linker
Amino acids 277-398: camB7H3 clone 2
SEQ ID NO:24
MKWVTFISLL FLFSSAYSQV QLVESGGGLV QPGGSLRLSC AASGLTFSSY NMGWFRQAPG QGLEAVASIT WSGRDTFYAD SVKGRFTISR DNSKNTLYLQ MNSLRAEDTA VYYCAANPWP VAAPRSGTYW GQGTLVTVSS SGGGGSGGGG SGGGGSGGGG SGNWVNVISD LKKIEDLIQS MHIDATLYTE SDVHPSCKVT AMKCFLLELQ VISLESGDAS IHDTVENLII LANNSLSSNG NVTESGCKEC EELEEKNIKE FLQSFVHIVQ MFINTSGSTS GSGKPGSGEG STKGHVQLVE SGGGLVQPGR SLRLSCAASG FTFSSYWMYW VRQTPGKGLE WVSTINRDGS ATWYADSVKG RFTISRDNAK NTGYLQMNSL EPDDTAVYYC VSDPDNYSSD EMVPYWGQGT QVTVSSVDEH HHHHHHHHH
Amino acids 1-18: leader
Amino acids 19-140: humanized camCD16
Amino acids 141-162: linker
Amino acids 163-276: IL-15 fragment
Amino acids 277-294: linker
Amino acids 295-416: camB7H3 clone 1
Amino acids 417-429: VDE linker and 10× his tag
SEQ ID NO:25
MKWVTFISLL FLFSSAYSQV QLVESGGGLV QPGGSLRLSC AASGLTFSSY NMGWFRQAPG QGLEAVASIT WSGRDTFYAD SVKGRFTISR DNSKNTLYLQ MNSLRAEDTA VYYCAANPWP VAAPRSGTYW GQGTLVTVSS SGGGGSGGGG SGGGGSGGGG SGNWVNVISD LKKIEDLIQS MHIDATLYTE SDVHPSCKVT AMKCFLLELQ VISLESGDAS IHDTVENLII LANNSLSSNG NVTESGCKEC EELEEKNIKE FLQSFVHIVQ MFINTSGSTS GSGKPGSGEG STKGQVQLVE SGGGLVQPGG SLRLSCAASG FTFSSYWMYW VRQTPGKGLE WVSTINRDGS ATWYADSVKG RFTISRDNAK NTGYLQMNSL KPDDTAVYYC VSDPDNYSSD EMVPYWGQGT QVTVSSVDEH HHHHHHHHH
Amino acids 1-18: leader
Amino acids 19-140: humanized camCD16
Amino acids 141-162: linker
Amino acids 163-276: IL-15 fragment
Amino acids 277-294: linker Amino acids 295-416: camB7H3 clone 2
Amino acids 417-429: VDE linker and 10× his tag SEQ ID NO:26
CATGTGCAGCTGGTGGAGTC TGGGGCGAGGC TTGGTGCAGC CTGGGAGGTC TCTGAGACTC TCCTGTGCAG CCTCTGGATT CACCTTCAGT AGCTACTGGA TGTACTGGGT CCGCCAGACT CAGGGAAG-G GGCTCGAGTG GGTCTCAACT ATTAATC TG A GGTA-TGC CACATGGTAT GCA-GACTCAG TGAAGGGCCG ATTCACCATC TCAAGCAGAAC ACGCCAAGAA CACGGGGTAT CCTGCAAATA ACAG GGCCA ACCTGACGAC ACGGCCGTGT ATTACTGTGT GAGCGATCCG GACAACTACT CTAGCGATGA CATGGTCCC TACTGCGGCC AGGGGACCCA GGTCACCGTC TCCTCA SEQ ID NO:27
CAGGTGCAGC TGGTGGAGTC TGCGGAGGC TTGGTGC GCGGGGGGTC TACAGACTC TCCTGTGCAG CCTGGATT CACCTTCAGT AGC-TACTGgA TGACTGGGT CCGCCAGACT CCAGG-GAAGG GGCTCGAGTG GGTCTCAACT ATTAATCGTG ATGGTAGTGC CACATGGTAT GCAGACTCAG TGAAGGGCCG ATTCACCATC TCCAGAGACA ACGCCAAGAA CACGGGTAT CTGCAAATGA ACAGCCTGAA ACCTGACGAC ACGGCCGTGT ATTACTGTGT GAGCGATCCG GACAACTACT CTAGCGATGA GATGGTCCCT TACTGGGGCC AGGGGACCCA CGTCACCGTC TCCTCA SEQ ID NO:28
ATGAAGTGGG TAACCTTTAT TTCCCTTCTT TTTCTCTTTA GCTCGGCTTA TTCCCACGTT CAGCTCGTTG AATCAGGCGG TGGGCTCGTG CAGCCTGGAA GATCTCTCCG CTTGAGCTGC GCGGCTTCAG GCTTTACCTT TTCCAGTTAT TGGATGTATT GGGTCCGGCA GACGCCAGGA AAGGGGCTTG AATGGGTGTC AACGATCAAC CGGGACGGCA GCGCAACCTG GTATGCCGAC TCCGTTAAAG GGAGGTTCAC AATAAGCCGA GACAATGCGA AAAACACAGG ATACCTGCAA ATGAATAGCT TGGAGCCTGA TGATACGGCT GTATATTATT GCGTGTCTGA TCCCGACAAC TATAGTAGTG ACGAGATGGT CCCATATTGG GGGCAGGGAA CACAAGTCAC AGTCTCCAGC GTCGACGAGC ATCATCATCA TCACCACCAC CACCACCAC SEQ ID NO:29
ATGAAGTGGG TAACCTTTAT TTCCCTTCTT TTTCTCTTTA GCTCGGCTTA TTCCCAGGTG CAGCTGGTGG AGTCTGGGGG AGGCTTGGTG CAGCCTGGGG GGTCACTGAG ACTCTCCTGT GCAGCCTCTG GATTCACCTT CAGTAGCTAC TGGATGTACT GGGTCCGCCA GACTCCAGGG AAGGGGCTCG AGTGGGTATC AACTATTAAT CGTGATGGTA GTGCCACATG GTATGCAGAC TCAGTGAAGG GCCGATTCAC CATCTCCAGA GACAACGCCA AGAACACGGG GTATCTGCAA ATGAACAGCC TGAAACCTGA CGACACGGCC GTGTATTACT GTGTGAGCGA TCCGGACAAC TACTCTAGCG ATGAGATGGT CCCTTACTGG GGCCAGGGGA CCCAGGTCAC CGTCTCCTCA GTCGACGAGC ATCATCATCA TCACCACCAC CACCACCAC SEQ ID NO:30
GCCGCCACCA TGAAGTGGGT AACCTTTATT TCCCTTCTTT TTCTCTTTAG CTCGGCTTAT TCCCAGGTGC AGCTGGTGGA GTCTGGGGGA GGCTTGGTGC AGCCTGGGGG CTCTCTGAGA CTCTCCTGTG CAGCCTCTGG CCTCACCTTC AGTAGCTATA ACATGGGCTG GTTCCGCCAG GCTCCAGGGC AAGGCCTTGA GGCTGTAGCA TCTATTACCT GGAGTGGTCG GGACACATTC TATGCAGACT CCGTGAAGGG CCGATTCACC ATCTCCAGAG ACAACTCCAA GAACACTCTC TATCTGCAAA TGAACAGCCT GCGCGCGGAG GACACGGCCG TTTATTATTG TGCTGCAAAC CCCTGGCCAG TGGCGGCGCC ACGTAGTGGC ACCTACTGGG GCCAAGGGAC CCTGGTCACC GTCTCCTCAT CTGGCGGCGG CGGTTCTGGT GGAGGAGGTA GTGGGGGGGG AGGAAGCGGA GGGGGTGGCT CAGGGCACGT TCAGCTCGTT GAATCAGGCG GTGGGCTCGT GCAGCCTGGA AGATCTCTCC GCTTGAGCTG CGCGGCTTCA GGCTTTACCT TTTCCAGTTA TTGGATGTAT TGGGTCCGGC AGACGCCAGG AAAGGGGCTT GAATGGGTGT CAACGATCAA CCGGGACGGC AGCGCAACCT GGTATGCCGA CTCCGTTAAA GGGAGGTTCA CAATAAGCCG AGACAATGCG AAAAACACAG GATACCTGCA AATGAATAGC TTGGAGCCTG ATGATACGGC TGTATATTAT TGCGTGTCTG ATCCCGACAA CTATAGTAGT GACGAGATGG TCCCATATTG GGGGCAGGGA ACACAAGTCA CAGTCTCCAG CGTCGACGAG CATCATCATC ATCACCACCA CCACCACCAC nucleotides 1-9: Kozak sequence
nucleotides 10-900: encode SEQ ID NO:20

SEQ ID NO:31
GCCGCCACCA TGAAGTGGGT AACCTTTATT TCCCTTCTTT TTCTCTTTAG CTCGGCTTAT TCCCAGGTGC AGCTGGTGGA GTCTGGGGGA GGCTTGGTGC AGCCTGGGGG CTCTCTGAGA CTCTCCTGTG CAGCCTCTGG CCTCACCTTC AGTAGCTATA ACATGGGCTG GTTCCGCCAG GCTCCAGGGC AAGGCCTTGA GGCTGTAGCA TCTATTACCT GGAGTGGTCG GGACACATTC TATGCAGACT CCGTGAAGGG CCGATTCACC ATCTCCAGAG ACAACTCCAA GAACACTCTC TATCTGCAAA TGAACAGCCT GCGCGCGGAG GACACGGCCG TTTATTATTG TGCTGCAAAC CCCTGGCCAG TGGCGGCGCC ACGTAGTGGC ACCTACTGGG GCCAAGGGAC CCTGGTCACC GTCTCCTCAT CTGGCGGCGG CGGTTCTGGT GGAGGAGGTA GTGGGGGGGG AGGAAGCGGA GGGGGTGGCT CAGGGCAGGT GCAGCTGGTG GAGTCTGGGG GAGGCTTGGT GCAGCCTGGG GGGTCACTGA GACTCTCCTG TGCAGCCTCT GGATTCACCT TCAGTAGCTA CTGGATGTAC TGGGTCCGCC AGACTCCAGG GAAGGGGCTC GAGTGGGTAT CAACTATTAA TCGTGATGGT AGTGCCACAT GGTATGCAGA CTCAGTGAAG GGCCGATTCA CCATCTCCAG AGACAACGCC AAGAACACGG GGTATCTGCA AATGAACAGC CTGAAACCTG ACGACACGGC CGTGTATTAC TGTGTGAGCG ATCCGGACAA CTACTCTAGC GATGAGATGG TCCCTTACTG GGGCCAGGGG ACCCAGGTCA CCGTCTCCTC AGTCGACGAG CATCATCATC ATCACCACCA CCACCACCAC nucleotides 1-9: Kozak sequence
nucleotides 10-900: encode SEQ ID NO:21

SEQ ID NO:32
GCCGCCACCA TGAAGTGGGT AACCTTTATT TCCCTTCTTT TTCTCTTTAG CTCGGCTTAT TCCCAGGTGC AGCTGGTGGA GTCTGGGGGA

GGCTTGGTGC AGCCTGGGGG CTCTCTGAGA
CTCTCCTGTG CAGCCTCTGG CCTCACCTTC
AGTAGCTATA ACATGGGCTG GTTCCGCCAG
GCTCCAGGGC AAGGCCTTGA GGCTGTAGCA
TCTATTACCT GGAGTGGTCG GGACACATTC
TATGCAGACT CCGTGAAGGG CCGATTCACC
ATCTCCAGAG ACAACTCCAA GAACACTCTC
TATCTGCAAA TGAACAGCCT GCGCGCGGAG
GACACGGCCG TTTATTATTG TGCTGCAAAC
CCCTGGCCAG TGGCGGCGCC ACGTAGTGGC
ACCTACTGGG GCCAAGGGAC CCTGGTCACC
GTCTCCTCAT CTGGCGGCGG CGGTTCTGGT
GGAGGAGGTA GTGGGGGGGG AGGAAGCGGA
GGGGGTGGCT CAGGGAACTG GGTGAATGTA
ATAAGTGATT TGAAAAAAAT TGAAGATCTT
ATTCAATCTA TGCATATTGA TGCTACTTTA
TATACGGAAA GTGATGTTCA CCCCAGTTGC
AAAGTAACAG CAATGAAGTG CTTTCTCTTG
GAGTTACAAG TTATTTCACT TGAGTCCGGA
GATGCAAGTA TTCATGATAC AGTAGAAAAT
CTGATCATCC TAGCAAACAA CAGTTTGTCT
TCTAATGGGA ATGTAACAGA ATCTGGATGC
AAAGAATGTG AGGAACTGGA GGAAAAAAAT
ATTAAAGAAT TTTTGCAGAG TTTTGTACAT
ATTGTCCAAA TGTTCATCAA CACTTCTGGC
AGTACCAGCG GGTCAGGGAA ACCTGGCAGT
GGGGAAGGTT CCACAAAAGG TCACGTTCAG
CTCGTTGAAT CAGGCGGTGG GCTCGTGCAG
CCTGGAAGAT CTCTCCGCTT GAGCTGCGCG
GCTTCAGGCT TTACCTTTTC CAGTTATTGG
ATGTATTGGG TCCGGCAGAC GCCAGGAAAG
GGGCTTGAAT GGGTGTCAAC GATCAACCGG
GACGGCAGCG CAACCTGGTA TGCCGACTCC
GTTAAAGGGA GGTTCACAAT AAGCCGAGAC
AATGCGAAAA ACACAGGATA CCTGCAAATG
AATAGCTTGG AGCCTGATGA TACGGCTGTA
TATTATTGCG TGTCTGATCC CGACAACTAT
AGTAGTGACG AGATGGTCCC ATATTGGGGG
CAGGGAACAC AAGTCACAGT CTCCAGCGTC
GACGAGCATC ATCATCATCA CCACCACCAC
CACCAC nucleotides 1-9: Kozak sequence
nucleotides 10-1296: encode SEQ ID NO:24

SEQ ID NO:33

GCCGCCACCA TGAAGTGGGT AACCTTTATT
TCCCTTCTTT TTCTCTTTAG CTCGGCTTAT
TCCCAGGTGC AGCTGGTGGA GTCTGGGGGA
GGCTTGGTGC AGCCTGGGGG CTCTCTGAGA
CTCTCCTGTG CAGCCTCTGG CCTCACCTTC
AGTAGCTATA ACATGGGCTG GTTCCGCCAG
GCTCCAGGGC AAGGCCTTGA GGCTGTAGCA
TCTATTACCT GGAGTGGTCG GGACACATTC
TATGCAGACT CCGTGAAGGG CCGATTCACC
ATCTCCAGAG ACAACTCCAA GAACACTCTC
TATCTGCAAA TGAACAGCCT GCGCGCGGAG
GACACGGCCG TTTATTATTG TGCTGCAAAC
CCCTGGCCAG TGGCGGCGCC ACGTAGTGGC
ACCTACTGGG GCCAAGGGAC CCTGGTCACC
GTCTCCTCAT CTGGCGGCGG CGGTTCTGGT
GGAGGAGGTA GTGGGGGGGG AGGAAGCGGA
GGGGGTGGCT CAGGGAACTG GGTGAATGTA
ATAAGTGATT TGAAAAAAAT TGAAGATCTT
ATTCAATCTA TGCATATTGA TGCTACTTTA
TATACGGAAA GTGATGTTCA CCCCAGTTGC
AAAGTAACAG CAATGAAGTG CTTTCTCTTG
GAGTTACAAG TTATTTCACT TGAGTCCGGA
GATGCAAGTA TTCATGATAC AGTAGAAAAT
CTGATCATCC TAGCAAACAA CAGTTTGTCT
TCTAATGGGA ATGTAACAGA ATCTGGATGC
AAAGAATGTG AGGAACTGGA GGAAAAAAAT
ATTAAAGAAT TTTTGCAGAG TTTTGTACAT
ATTGTCCAAA TGTTCATCAA CACTTCTGGC
AGTACCAGCG GGTCAGGGAA ACCTGGCAGT
GGGGAAGGTT CCACAAAAGG TCAGGTGCAG
CTGGTGGAGT CTGGGGGAGG CTTGGTGCAG
CCTGGGGGGT CACTGAGACT CTCCTGTGCA
GCCTCTGGAT TCACCTTCAG TAGCTACTGG
ATGTACTGGG TCCGCCAGAC TCCAGGGAAG
GGGCTCGAGT GGGTATCAAC TATTAATCGT
GATGGTAGTG CCACATGGTA TGCAGACTCA
GTGAAGGGCC GATTCACCAT CTCCAGAGAC
AACGCCAAGA ACACGGGGTA TCTGCAAATG
AACAGCCTGA AACCTGACGA CACGGCCGTG
TATTACTGTG TGAGCGATCC GGACAACTAC
TCTAGCGATG AGATGGTCCC TTACTGGGGC
CAGGGGACCC AGGTCACCGT CTCCTCAGTC
GACGAGCATC ATCATCATCA CCACCACCAC
CACCAC nucleotides 1-9: Kozak sequence
nucleotides 10-1296: encode SEQ ID NO:25

The invention claimed is:

1. An anti-B7H3 polypeptide comprising:

SEQ ID NO:4, SEQ ID NO:5, and SEQ ID NO:6.

2. A compound comprising:

a targeting domain comprising an anti-B7H3 polypeptide, the anti-B7H3 polypeptide comprising:

SEQ ID NO:4,

SEQ ID NO:5, and

SEQ ID NO:6, and an immune cell engaging domain operably linked to the targeting domain.

3. The compound of claim 2, wherein the immune cell engaging domain engages a natural killer (NK) cell.

4. The compound of claim 3, wherein:

the immune cell engaging domain comprises a ligand or antibody that specifically binds to CD16.

5. The compound of claim 4, wherein the immune cell engaging domain comprises an scFv, a $F(ab)_2$, a Fab, or a single domain antibody (sdAb).

6. A compound comprising:

an immune cell engaging domain comprising SEQ ID NO:19; and a targeting domain comprising SEQ ID NO:1, SEQ ID NO:2, or SEQ ID NO:3.

7. The compound of claim 6, wherein the targeting domain and the immune cell engaging domain are linked by SEQ ID NO:14.

8. The compound of claim 6, wherein the compound further comprises amino acids 19-294 of SEQ ID NO:20 or amino acids 19-284 of SEQ ID NO:21.

9. The compound of claim 2, further comprising an immune cell activating domain.

10. The compound of claim 9, wherein:

the immune cell engaging domain engages an NK cell; and the immune cell activating domain comprises a cytokine or a functional portion thereof.

11. The compound of claim 10, wherein the cytokine is IL-15, or a functional variant thereof.

12. The compound of claim 9, wherein the compound comprises:

the targeting domain operably linked to the immune cell activating domain;

the immune cell engaging domain operably linked to the immune cell activating domain and comprising SEQ ID NO: 19; and the immune cell activating domain comprising:

SEQ ID NO:11 or a variant of SEQ ID NO:11 comprising an N72D or N72A amino acid substitution.

13. The compound of claim 12, wherein:

SEQ ID NO:19 and the immune cell activating domain are linked by SEQ ID NO:14; and the immune cell activating domain is linked to the targeting domain by SEQ ID NO:15.

14. The compound of claim 13, wherein the compound is as set forth in SEQ ID NO:22 or SEQ ID NO:23 or any amino acid sequence having 90% or greater identity thereto.

15. An isolated nucleic acid sequence encoding the compound of claim 2.

16. A protein comprising the amino acid sequence of SEQ ID NO:1, SEQ ID NO:2, SEQ ID NO:9, SEQ ID NO:10, SEQ ID NO:20, SEQ ID NO:21, SEQ ID NO:22, SEQ ID NO:23, SEQ ID NO:24, or SEQ ID NO:25.

17. A pharmaceutical composition comprising:

the compound of claim 2; and a pharmaceutically acceptable carrier.

18. A method comprising:

administering to a subject a multispecific compound in an amount effective to induce natural killer (NK)-mediated killing of a cell, the multispecific compound comprising:

a targeting domain comprising the anti-B7H3 polypeptide of claim 1; and an NK engaging domain operably linked to the targeting domain.

19. The method of claim 18, wherein the multispecific compound further comprises an immune cell activating domain comprising an IL-15, or a functional portion thereof, operably linked to the NK engaging domain.

20. A method of treating a subject having, or at risk of having cancer comprising:

administering to the subject an effective amount of a compound comprising:

a targeting domain comprising the anti-B7H3 polypeptide of claim 1; and an NK engaging domain operably linked to the anti-B7H3 polypeptide.

21. The method of claim 20, wherein the compound further comprises an immune cell activating domain comprising an IL-15, or a functional portion thereof, operably linked to the NK engaging domain.

22. The method of claim 20, wherein the cancer comprises prostate cancer, lung cancer, colon cancer, rectum cancer, urinary bladder cancer, melanoma, kidney cancer, renal cancer, oral cavity cancer, pharynx cancer, pancreas cancer, uterine cancer, thyroid cancer, skin cancer, head and neck cancer, cervical cancer, ovarian cancer, or hematopoietic cancer.

23. The method of claim 20, wherein the multispecific compound is administered prior to, simultaneously with, or following chemotherapy, surgical resection of a tumor, or radiation therapy.

* * * * *

SEQUENCE LISTING

```
<160> NUMBER OF SEQ ID NOS: 33

<210> SEQ ID NO 1
<211> LENGTH: 122
<212> TYPE: PRT
<213> ORGANISM: artificial
<220> FEATURE:
<223> OTHER INFORMATION: polypeptide

<400> SEQUENCE: 1

His Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Thr Pro Gly Lys Gly Leu Glu Trp Val
        35                  40                  45

Ser Thr Ile Asn Arg Asp Gly Ser Ala Thr Trp Tyr Ala Asp Ser Val
```

```
    50                  55                  60

Lys Gly Arg Phe Thr Ile Ser Arg Asp Asn Ala Lys Asn Thr Gly Tyr
65                  70                  75                  80

Leu Gln Met Asn Ser Leu Glu Pro Asp Asp Thr Ala Val Tyr Tyr Cys
                85                  90                  95

Val Ser Asp Pro Asp Asn Tyr Ser Ser Asp Glu Met Val Pro Tyr Trp
            100                 105                 110

Gly Gln Gly Thr Gln Val Thr Val Ser Ser
        115                 120


<210> SEQ ID NO 2
<211> LENGTH: 122
<212> TYPE: PRT
<213> ORGANISM: artificial
<220> FEATURE:
<223> OTHER INFORMATION: polypeptide

<400> SEQUENCE: 2

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Thr Pro Gly Lys Gly Leu Glu Trp Val
        35                  40                  45

Ser Thr Ile Asn Arg Asp Gly Ser Ala Thr Trp Tyr Ala Asp Ser Val
    50                  55                  60

Lys Gly Arg Phe Thr Ile Ser Arg Asp Asn Ala Lys Asn Thr Gly Tyr
65                  70                  75                  80

Leu Gln Met Asn Ser Leu Lys Pro Asp Asp Thr Ala Val Tyr Tyr Cys
                85                  90                  95

Val Ser Asp Pro Asp Asn Tyr Ser Ser Asp Glu Met Val Pro Tyr Trp
            100                 105                 110

Gly Gln Gly Thr Gln Val Thr Val Ser Ser
        115                 120


<210> SEQ ID NO 3
<211> LENGTH: 122
<212> TYPE: PRT
<213> ORGANISM: artificial
<220> FEATURE:
<223> OTHER INFORMATION: polypeptide
<220> FEATURE:
<221> NAME/KEY: MISC_FEATURE
<222> LOCATION: (1)..(122)
<223> OTHER INFORMATION: X is any amino acid

<400> SEQUENCE: 3

Xaa Val Gln Leu Val Glu Ser Gly Gly Gly Leu Val Gln Pro Gly Xaa
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Thr Pro Gly Lys Gly Leu Glu Trp Val
        35                  40                  45

Ser Thr Ile Asn Arg Asp Gly Ser Ala Thr Trp Tyr Ala Asp Ser Val
    50                  55                  60

Lys Gly Arg Phe Thr Ile Ser Arg Asp Asn Ala Lys Asn Thr Gly Tyr
65                  70                  75                  80

Leu Gln Met Asn Ser Leu Xaa Pro Asp Asp Thr Ala Val Tyr Tyr Cys
                85                  90                  95
```

```
Val Ser Asp Pro Asp Asn Tyr Ser Ser Asp Glu Met Val Pro Tyr Trp
            100                 105                 110

Gly Gln Gly Thr Gln Val Thr Val Ser Ser
        115                 120


<210> SEQ ID NO 4
<211> LENGTH: 5
<212> TYPE: PRT
<213> ORGANISM: artificial
<220> FEATURE:
<223> OTHER INFORMATION: polypeptide

<400> SEQUENCE: 4

Ser Tyr Trp Met Tyr
1               5


<210> SEQ ID NO 5
<211> LENGTH: 19
<212> TYPE: PRT
<213> ORGANISM: artificial
<220> FEATURE:
<223> OTHER INFORMATION: polypeptide

<400> SEQUENCE: 5

Ile Asn Arg Asp Gly Ser Ala Thr Trp Tyr Ala Asp Ser Val Lys Gly
1               5                   10                  15

Arg Phe Thr


<210> SEQ ID NO 6
<211> LENGTH: 13
<212> TYPE: PRT
<213> ORGANISM: artificial
<220> FEATURE:
<223> OTHER INFORMATION: polypeptide

<400> SEQUENCE: 6

Asp Pro Asp Asn Tyr Ser Ser Asp Glu Met Val Pro Tyr
1               5                   10


<210> SEQ ID NO 7
<211> LENGTH: 18
<212> TYPE: PRT
<213> ORGANISM: artificial
<220> FEATURE:
<223> OTHER INFORMATION: polypeptide

<400> SEQUENCE: 7

Met Lys Trp Val Thr Phe Ile Ser Leu Leu Phe Leu Phe Ser Ser Ala
1               5                   10                  15

Tyr Ser


<210> SEQ ID NO 8
<211> LENGTH: 13
<212> TYPE: PRT
<213> ORGANISM: artificial
<220> FEATURE:
<223> OTHER INFORMATION: polypeptide

<400> SEQUENCE: 8

Val Asp Glu His His His His His His His His His His
1               5                   10


<210> SEQ ID NO 9
<211> LENGTH: 153
```

<212> TYPE: PRT
<213> ORGANISM: artificial
<220> FEATURE:
<223> OTHER INFORMATION: polypeptide

<400> SEQUENCE: 9

Met Lys Trp Val Thr Phe Ile Ser Leu Leu Phe Leu Phe Ser Ser Ala
1 5 10 15

Tyr Ser His Val Gln Leu Val Glu Ser Gly Gly Gly Leu Val Gln Pro
20 25 30

Gly Arg Ser Leu Arg Leu Ser Cys Ala Ala Ser Gly Phe Thr Phe Ser
35 40 45

Ser Tyr Trp Met Tyr Trp Val Arg Gln Thr Pro Gly Lys Gly Leu Glu
50 55 60

Trp Val Ser Thr Ile Asn Arg Asp Gly Ser Ala Thr Trp Tyr Ala Asp
65 70 75 80

Ser Val Lys Gly Arg Phe Thr Ile Ser Arg Asp Asn Ala Lys Asn Thr
85 90 95

Gly Tyr Leu Gln Met Asn Ser Leu Glu Pro Asp Asp Thr Ala Val Tyr
100 105 110

Tyr Cys Val Ser Asp Pro Asp Asn Tyr Ser Ser Asp Glu Met Val Pro
115 120 125

Tyr Trp Gly Gln Gly Thr Gln Val Thr Val Ser Ser Val Asp Glu His
130 135 140

His His His His His His His His His
145 150

<210> SEQ ID NO 10
<211> LENGTH: 153
<212> TYPE: PRT
<213> ORGANISM: artificial
<220> FEATURE:
<223> OTHER INFORMATION: polypeptide

<400> SEQUENCE: 10

Met Lys Trp Val Thr Phe Ile Ser Leu Leu Phe Leu Phe Ser Ser Ala
1 5 10 15

Tyr Ser Gln Val Gln Leu Val Glu Ser Gly Gly Gly Leu Val Gln Pro
20 25 30

Gly Gly Ser Leu Arg Leu Ser Cys Ala Ala Ser Gly Phe Thr Phe Ser
35 40 45

Ser Tyr Trp Met Tyr Trp Val Arg Gln Thr Pro Gly Lys Gly Leu Glu
50 55 60

Trp Val Ser Thr Ile Asn Arg Asp Gly Ser Ala Thr Trp Tyr Ala Asp
65 70 75 80

Ser Val Lys Gly Arg Phe Thr Ile Ser Arg Asp Asn Ala Lys Asn Thr
85 90 95

Gly Tyr Leu Gln Met Asn Ser Leu Lys Pro Asp Asp Thr Ala Val Tyr
100 105 110

Tyr Cys Val Ser Asp Pro Asp Asn Tyr Ser Ser Asp Glu Met Val Pro
115 120 125

Tyr Trp Gly Gln Gly Thr Gln Val Thr Val Ser Ser Val Asp Glu His
130 135 140

His His His His His His His His His
145 150

<210> SEQ ID NO 11

<211> LENGTH: 114
<212> TYPE: PRT
<213> ORGANISM: artificial
<220> FEATURE:
<223> OTHER INFORMATION: polypeptide

<400> SEQUENCE: 11

Asn Trp Val Asn Val Ile Ser Asp Leu Lys Lys Ile Glu Asp Leu Ile
1 5 10 15

Gln Ser Met His Ile Asp Ala Thr Leu Tyr Thr Glu Ser Asp Val His
20 25 30

Pro Ser Cys Lys Val Thr Ala Met Lys Cys Phe Leu Leu Glu Leu Gln
35 40 45

Val Ile Ser Leu Glu Ser Gly Asp Ala Ser Ile His Asp Thr Val Glu
50 55 60

Asn Leu Ile Ile Leu Ala Asn Asn Ser Leu Ser Ser Asn Gly Asn Val
65 70 75 80

Thr Glu Ser Gly Cys Lys Glu Cys Glu Glu Leu Glu Glu Lys Asn Ile
85 90 95

Lys Glu Phe Leu Gln Ser Phe Val His Ile Val Gln Met Phe Ile Asn
100 105 110

Thr Ser

<210> SEQ ID NO 12
<211> LENGTH: 20
<212> TYPE: PRT
<213> ORGANISM: artificial
<220> FEATURE:
<223> OTHER INFORMATION: polypeptide

<400> SEQUENCE: 12

Pro Ser Gly Gln Ala Gly Ala Ala Ala Ser Glu Ser Leu Phe Val Ser
1 5 10 15

Asn His Ala Tyr
20

<210> SEQ ID NO 13
<211> LENGTH: 7
<212> TYPE: PRT
<213> ORGANISM: artificial
<220> FEATURE:
<223> OTHER INFORMATION: polypeptide

<400> SEQUENCE: 13

Glu Ala Ser Gly Gly Pro Glu
1 5

<210> SEQ ID NO 14
<211> LENGTH: 20
<212> TYPE: PRT
<213> ORGANISM: artificial
<220> FEATURE:
<223> OTHER INFORMATION: polypeptide

<400> SEQUENCE: 14

Ser Gly Gly Gly Gly Ser Gly Gly Gly Gly Ser Gly Gly Gly Gly Ser
1 5 10 15

Gly Gly Gly Gly
20

<210> SEQ ID NO 15
<211> LENGTH: 18

<212> TYPE: PRT
<213> ORGANISM: artificial
<220> FEATURE:
<223> OTHER INFORMATION: polypeptide

<400> SEQUENCE: 15

```
Gly Ser Thr Ser Gly Ser Gly Lys Pro Gly Ser Gly Glu Gly Ser Thr
1               5                   10                  15

Lys Gly
```

<210> SEQ ID NO 16
<211> LENGTH: 17
<212> TYPE: PRT
<213> ORGANISM: artificial
<220> FEATURE:
<223> OTHER INFORMATION: polypeptide

<400> SEQUENCE: 16

```
Glu Pro Lys Ser Ser Asp Lys Thr His Thr Ser Pro Pro Ser Pro Glu
1               5                   10                  15

Leu
```

<210> SEQ ID NO 17
<211> LENGTH: 25
<212> TYPE: PRT
<213> ORGANISM: artificial
<220> FEATURE:
<223> OTHER INFORMATION: polypeptide

<400> SEQUENCE: 17

```
Arg Ala Thr Pro Ser His Asn Ser His Gln Val Pro Ser Ala Gly Gly
1               5                   10                  15

Pro Thr Ala Asn Ser Gly Thr Ser Gly
            20                  25
```

<210> SEQ ID NO 18
<211> LENGTH: 19
<212> TYPE: PRT
<213> ORGANISM: artificial
<220> FEATURE:
<223> OTHER INFORMATION: polypeptide

<400> SEQUENCE: 18

```
Ser Ser Gly Gly Gly Gly Ser Gly Gly Gly Gly Gly Gly Ser Ser Arg
1               5                   10                  15

Ser Ser Leu
```

<210> SEQ ID NO 19
<211> LENGTH: 122
<212> TYPE: PRT
<213> ORGANISM: artificial
<220> FEATURE:
<223> OTHER INFORMATION: polypeptide

<400> SEQUENCE: 19

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Leu Thr Phe Ser Ser Tyr
            20                  25                  30

Asn Met Gly Trp Phe Arg Gln Ala Pro Gly Gln Gly Leu Glu Ala Val
        35                  40                  45

Ala Ser Ile Thr Trp Ser Gly Arg Asp Thr Phe Tyr Ala Asp Ser Val
    50                  55                  60
```

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Ala Asn Pro Trp Pro Val Ala Ala Pro Arg Ser Gly Thr Tyr Trp
100 105 110

Gly Gln Gly Thr Leu Val Thr Val Ser Ser
115 120

<210> SEQ ID NO 20
<211> LENGTH: 297
<212> TYPE: PRT
<213> ORGANISM: artificial
<220> FEATURE:
<223> OTHER INFORMATION: polypeptide

<400> SEQUENCE: 20

Met Lys Trp Val Thr Phe Ile Ser Leu Leu Phe Leu Phe Ser Ser Ala
1 5 10 15

Tyr Ser Gln Val Gln Leu Val Glu Ser Gly Gly Gly Leu Val Gln Pro
20 25 30

Gly Gly Ser Leu Arg Leu Ser Cys Ala Ala Ser Gly Leu Thr Phe Ser
35 40 45

Ser Tyr Asn Met Gly Trp Phe Arg Gln Ala Pro Gly Gln Gly Leu Glu
50 55 60

Ala Val Ala Ser Ile Thr Trp Ser Gly Arg Asp Thr Phe Tyr Ala Asp
65 70 75 80

Ser Val Lys Gly Arg Phe Thr Ile Ser Arg Asp Asn Ser Lys Asn Thr
85 90 95

Leu Tyr Leu Gln Met Asn Ser Leu Arg Ala Glu Asp Thr Ala Val Tyr
100 105 110

Tyr Cys Ala Ala Asn Pro Trp Pro Val Ala Ala Pro Arg Ser Gly Thr
115 120 125

Tyr Trp Gly Gln Gly Thr Leu Val Thr Val Ser Ser Ser Gly Gly Gly
130 135 140

Gly Ser Gly Gly Gly Gly Ser Gly Gly Gly Gly Ser Gly Gly Gly Gly
145 150 155 160

Ser Gly His Val Gln Leu Val Glu Ser Gly Gly Gly Leu Val Gln Pro
165 170 175

Gly Arg Ser Leu Arg Leu Ser Cys Ala Ala Ser Gly Phe Thr Phe Ser
180 185 190

Ser Tyr Trp Met Tyr Trp Val Arg Gln Thr Pro Gly Lys Gly Leu Glu
195 200 205

Trp Val Ser Thr Ile Asn Arg Asp Gly Ser Ala Thr Trp Tyr Ala Asp
210 215 220

Ser Val Lys Gly Arg Phe Thr Ile Ser Arg Asp Asn Ala Lys Asn Thr
225 230 235 240

Gly Tyr Leu Gln Met Asn Ser Leu Glu Pro Asp Asp Thr Ala Val Tyr
245 250 255

Tyr Cys Val Ser Asp Pro Asp Asn Tyr Ser Ser Asp Glu Met Val Pro
260 265 270

Tyr Trp Gly Gln Gly Thr Gln Val Thr Val Ser Ser Val Asp Glu His
275 280 285

His His His His His His His His His
290 295

<210> SEQ ID NO 21
<211> LENGTH: 297
<212> TYPE: PRT
<213> ORGANISM: artificial
<220> FEATURE:
<223> OTHER INFORMATION: polypeptide

<400> SEQUENCE: 21

```
Met Lys Trp Val Thr Phe Ile Ser Leu Leu Phe Leu Phe Ser Ser Ala
1               5                   10                  15

Tyr Ser Gln Val Gln Leu Val Glu Ser Gly Gly Gly Leu Val Gln Pro
            20                  25                  30

Gly Gly Ser Leu Arg Leu Ser Cys Ala Ala Ser Gly Leu Thr Phe Ser
        35                  40                  45

Ser Tyr Asn Met Gly Trp Phe Arg Gln Ala Pro Gly Gln Gly Leu Glu
    50                  55                  60

Ala Val Ala Ser Ile Thr Trp Ser Gly Arg Asp Thr Phe Tyr Ala Asp
65                  70                  75                  80

Ser Val Lys Gly Arg Phe Thr Ile Ser Arg Asp Asn Ser Lys Asn Thr
                85                  90                  95

Leu Tyr Leu Gln Met Asn Ser Leu Arg Ala Glu Asp Thr Ala Val Tyr
            100                 105                 110

Tyr Cys Ala Ala Asn Pro Trp Pro Val Ala Ala Pro Arg Ser Gly Thr
        115                 120                 125

Tyr Trp Gly Gln Gly Thr Leu Val Thr Val Ser Ser Ser Gly Gly Gly
    130                 135                 140

Gly Ser Gly Gly Gly Gly Ser Gly Gly Gly Gly Ser Gly Gly Gly Gly
145                 150                 155                 160

Ser Gly Gln Val Gln Leu Val Glu Ser Gly Gly Gly Leu Val Gln Pro
                165                 170                 175

Gly Gly Ser Leu Arg Leu Ser Cys Ala Ala Ser Gly Phe Thr Phe Ser
            180                 185                 190

Ser Tyr Trp Met Tyr Trp Val Arg Gln Thr Pro Gly Lys Gly Leu Glu
        195                 200                 205

Trp Val Ser Thr Ile Asn Arg Asp Gly Ser Ala Thr Trp Tyr Ala Asp
    210                 215                 220

Ser Val Lys Gly Arg Phe Thr Ile Ser Arg Asp Asn Ala Lys Asn Thr
225                 230                 235                 240

Gly Tyr Leu Gln Met Asn Ser Leu Lys Pro Asp Asp Thr Ala Val Tyr
                245                 250                 255

Tyr Cys Val Ser Asp Pro Asp Asn Tyr Ser Ser Asp Glu Met Val Pro
            260                 265                 270

Tyr Trp Gly Gln Gly Thr Gln Val Thr Val Ser Ser Val Asp Glu His
        275                 280                 285

His His His His His His His His His
    290                 295
```

<210> SEQ ID NO 22
<211> LENGTH: 398
<212> TYPE: PRT
<213> ORGANISM: artificial
<220> FEATURE:
<223> OTHER INFORMATION: polypeptide

<400> SEQUENCE: 22

```
Gln Val Gln Leu Val Glu Ser Gly Gly Gly Leu Val Gln Pro Gly Gly
```

-continued 1 5 10 15

Ser Leu Arg Leu Ser Cys Ala Ala Ser Gly Leu Thr Phe Ser Ser Tyr
20 25 30

Asn Met Gly Trp Phe Arg Gln Ala Pro Gly Gln Gly Leu Glu Ala Val
35 40 45

Ala Ser Ile Thr Trp Ser Gly Arg Asp Thr Phe Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Ala Asn Pro Trp Pro Val Ala Ala Pro Arg Ser Gly Thr Tyr Trp
100 105 110

Gly Gln Gly Thr Leu Val Thr Val Ser Ser Ser Gly Gly Gly Gly Ser
115 120 125

Gly Gly Gly Gly Ser Gly Gly Gly Gly Ser Gly Gly Gly Gly Ser Gly
130 135 140

Asn Trp Val Asn Val Ile Ser Asp Leu Lys Lys Ile Glu Asp Leu Ile
145 150 155 160

Gln Ser Met His Ile Asp Ala Thr Leu Tyr Thr Glu Ser Asp Val His
165 170 175

Pro Ser Cys Lys Val Thr Ala Met Lys Cys Phe Leu Leu Glu Leu Gln
180 185 190

Val Ile Ser Leu Glu Ser Gly Asp Ala Ser Ile His Asp Thr Val Glu
195 200 205

Asn Leu Ile Ile Leu Ala Asn Asn Ser Leu Ser Ser Asn Gly Asn Val
210 215 220

Thr Glu Ser Gly Cys Lys Glu Cys Glu Glu Leu Glu Glu Lys Asn Ile
225 230 235 240

Lys Glu Phe Leu Gln Ser Phe Val His Ile Val Gln Met Phe Ile Asn
245 250 255

Thr Ser Gly Ser Thr Ser Gly Ser Gly Lys Pro Gly Ser Gly Glu Gly
260 265 270

Ser Thr Lys Gly His Val Gln Leu Val Glu Ser Gly Gly Gly Leu Val
275 280 285

Gln Pro Gly Arg Ser Leu Arg Leu Ser Cys Ala Ala Ser Gly Phe Thr
290 295 300

Phe Ser Ser Tyr Trp Met Tyr Trp Val Arg Gln Thr Pro Gly Lys Gly
305 310 315 320

Leu Glu Trp Val Ser Thr Ile Asn Arg Asp Gly Ser Ala Thr Trp Tyr
325 330 335

Ala Asp Ser Val Lys Gly Arg Phe Thr Ile Ser Arg Asp Asn Ala Lys
340 345 350

Asn Thr Gly Tyr Leu Gln Met Asn Ser Leu Glu Pro Asp Asp Thr Ala
355 360 365

Val Tyr Tyr Cys Val Ser Asp Pro Asp Asn Tyr Ser Ser Asp Glu Met
370 375 380

Val Pro Tyr Trp Gly Gln Gly Thr Gln Val Thr Val Ser Ser
385 390 395

<210> SEQ ID NO 23
<211> LENGTH: 398
<212> TYPE: PRT
<213> ORGANISM: artificial

<220> FEATURE:
<223> OTHER INFORMATION: polypeptide

<400> SEQUENCE: 23

Gln Val Gln Leu Val Glu Ser Gly Gly Gly Leu Val Gln Pro Gly Gly
1 5 10 15

Ser Leu Arg Leu Ser Cys Ala Ala Ser Gly Leu Thr Phe Ser Ser Tyr
20 25 30

Asn Met Gly Trp Phe Arg Gln Ala Pro Gly Gln Gly Leu Glu Ala Val
35 40 45

Ala Ser Ile Thr Trp Ser Gly Arg Asp Thr Phe Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Ala Asn Pro Trp Pro Val Ala Ala Pro Arg Ser Gly Thr Tyr Trp
100 105 110

Gly Gln Gly Thr Leu Val Thr Val Ser Ser Ser Gly Gly Gly Gly Ser
115 120 125

Gly Gly Gly Gly Ser Gly Gly Gly Gly Ser Gly Gly Gly Gly Ser Gly
130 135 140

Asn Trp Val Asn Val Ile Ser Asp Leu Lys Lys Ile Glu Asp Leu Ile
145 150 155 160

Gln Ser Met His Ile Asp Ala Thr Leu Tyr Thr Glu Ser Asp Val His
165 170 175

Pro Ser Cys Lys Val Thr Ala Met Lys Cys Phe Leu Leu Glu Leu Gln
180 185 190

Val Ile Ser Leu Glu Ser Gly Asp Ala Ser Ile His Asp Thr Val Glu
195 200 205

Asn Leu Ile Ile Leu Ala Asn Asn Ser Leu Ser Ser Asn Gly Asn Val
210 215 220

Thr Glu Ser Gly Cys Lys Glu Cys Glu Glu Leu Glu Glu Lys Asn Ile
225 230 235 240

Lys Glu Phe Leu Gln Ser Phe Val His Ile Val Gln Met Phe Ile Asn
245 250 255

Thr Ser Gly Ser Thr Ser Gly Ser Gly Lys Pro Gly Ser Gly Glu Gly
260 265 270

Ser Thr Lys Gly Gln Val Gln Leu Val Glu Ser Gly Gly Gly Leu Val
275 280 285

Gln Pro Gly Gly Ser Leu Arg Leu Ser Cys Ala Ala Ser Gly Phe Thr
290 295 300

Phe Ser Ser Tyr Trp Met Tyr Trp Val Arg Gln Thr Pro Gly Lys Gly
305 310 315 320

Leu Glu Trp Val Ser Thr Ile Asn Arg Asp Gly Ser Ala Thr Trp Tyr
325 330 335

Ala Asp Ser Val Lys Gly Arg Phe Thr Ile Ser Arg Asp Asn Ala Lys
340 345 350

Asn Thr Gly Tyr Leu Gln Met Asn Ser Leu Lys Pro Asp Asp Thr Ala
355 360 365

Val Tyr Tyr Cys Val Ser Asp Pro Asp Asn Tyr Ser Ser Asp Glu Met
370 375 380

Val Pro Tyr Trp Gly Gln Gly Thr Gln Val Thr Val Ser Ser
385 390 395

<210> SEQ ID NO 24
<211> LENGTH: 429
<212> TYPE: PRT
<213> ORGANISM: artificial
<220> FEATURE:
<223> OTHER INFORMATION: polypeptide

<400> SEQUENCE: 24

Met Lys Trp Val Thr Phe Ile Ser Leu Leu Phe Leu Phe Ser Ser Ala
1               5                   10                  15

Tyr Ser Gln Val Gln Leu Val Glu Ser Gly Gly Gly Leu Val Gln Pro
            20                  25                  30

Gly Gly Ser Leu Arg Leu Ser Cys Ala Ala Ser Gly Leu Thr Phe Ser
        35                  40                  45

Ser Tyr Asn Met Gly Trp Phe Arg Gln Ala Pro Gly Gln Gly Leu Glu
    50                  55                  60

Ala Val Ala Ser Ile Thr Trp Ser Gly Arg Asp Thr Phe Tyr Ala Asp
65                  70                  75                  80

Ser Val Lys Gly Arg Phe Thr Ile Ser Arg Asp Asn Ser Lys Asn Thr
                85                  90                  95

Leu Tyr Leu Gln Met Asn Ser Leu Arg Ala Glu Asp Thr Ala Val Tyr
            100                 105                 110

Tyr Cys Ala Ala Asn Pro Trp Pro Val Ala Ala Pro Arg Ser Gly Thr
        115                 120                 125

Tyr Trp Gly Gln Gly Thr Leu Val Thr Val Ser Ser Ser Gly Gly Gly
    130                 135                 140

Gly Ser Gly Gly Gly Gly Ser Gly Gly Gly Gly Ser Gly Gly Gly Gly
145                 150                 155                 160

Ser Gly Asn Trp Val Asn Val Ile Ser Asp Leu Lys Lys Ile Glu Asp
                165                 170                 175

Leu Ile Gln Ser Met His Ile Asp Ala Thr Leu Tyr Thr Glu Ser Asp
            180                 185                 190

Val His Pro Ser Cys Lys Val Thr Ala Met Lys Cys Phe Leu Leu Glu
        195                 200                 205

Leu Gln Val Ile Ser Leu Glu Ser Gly Asp Ala Ser Ile His Asp Thr
    210                 215                 220

Val Glu Asn Leu Ile Ile Leu Ala Asn Asn Ser Leu Ser Ser Asn Gly
225                 230                 235                 240

Asn Val Thr Glu Ser Gly Cys Lys Glu Cys Glu Glu Leu Glu Glu Lys
                245                 250                 255

Asn Ile Lys Glu Phe Leu Gln Ser Phe Val His Ile Val Gln Met Phe
            260                 265                 270

Ile Asn Thr Ser Gly Ser Thr Ser Gly Ser Gly Lys Pro Gly Ser Gly
        275                 280                 285

Glu Gly Ser Thr Lys Gly His Val Gln Leu Val Glu Ser Gly Gly Gly
    290                 295                 300

Leu Val Gln Pro Gly Arg Ser Leu Arg Leu Ser Cys Ala Ala Ser Gly
305                 310                 315                 320

Phe Thr Phe Ser Ser Tyr Trp Met Tyr Trp Val Arg Gln Thr Pro Gly
                325                 330                 335

Lys Gly Leu Glu Trp Val Ser Thr Ile Asn Arg Asp Gly Ser Ala Thr
            340                 345                 350

Trp Tyr Ala Asp Ser Val Lys Gly Arg Phe Thr Ile Ser Arg Asp Asn
        355                 360                 365

Ala Lys Asn Thr Gly Tyr Leu Gln Met Asn Ser Leu Glu Pro Asp Asp
370 375 380

Thr Ala Val Tyr Tyr Cys Val Ser Asp Pro Asp Asn Tyr Ser Ser Asp
385 390 395 400

Glu Met Val Pro Tyr Trp Gly Gln Gly Thr Gln Val Thr Val Ser Ser
405 410 415

Val Asp Glu His His His His His His His His His His
420 425

<210> SEQ ID NO 25
<211> LENGTH: 429
<212> TYPE: PRT
<213> ORGANISM: artificial
<220> FEATURE:
<223> OTHER INFORMATION: polypeptide

<400> SEQUENCE: 25

Met Lys Trp Val Thr Phe Ile Ser Leu Leu Phe Leu Phe Ser Ser Ala
1 5 10 15

Tyr Ser Gln Val Gln Leu Val Glu Ser Gly Gly Gly Leu Val Gln Pro
20 25 30

Gly Gly Ser Leu Arg Leu Ser Cys Ala Ala Ser Gly Leu Thr Phe Ser
35 40 45

Ser Tyr Asn Met Gly Trp Phe Arg Gln Ala Pro Gly Gln Gly Leu Glu
50 55 60

Ala Val Ala Ser Ile Thr Trp Ser Gly Arg Asp Thr Phe Tyr Ala Asp
65 70 75 80

Ser Val Lys Gly Arg Phe Thr Ile Ser Arg Asp Asn Ser Lys Asn Thr
85 90 95

Leu Tyr Leu Gln Met Asn Ser Leu Arg Ala Glu Asp Thr Ala Val Tyr
100 105 110

Tyr Cys Ala Ala Asn Pro Trp Pro Val Ala Ala Pro Arg Ser Gly Thr
115 120 125

Tyr Trp Gly Gln Gly Thr Leu Val Thr Val Ser Ser Ser Gly Gly Gly
130 135 140

Gly Ser Gly Gly Gly Gly Ser Gly Gly Gly Gly Ser Gly Gly Gly Gly
145 150 155 160

Ser Gly Asn Trp Val Asn Val Ile Ser Asp Leu Lys Lys Ile Glu Asp
165 170 175

Leu Ile Gln Ser Met His Ile Asp Ala Thr Leu Tyr Thr Glu Ser Asp
180 185 190

Val His Pro Ser Cys Lys Val Thr Ala Met Lys Cys Phe Leu Leu Glu
195 200 205

Leu Gln Val Ile Ser Leu Glu Ser Gly Asp Ala Ser Ile His Asp Thr
210 215 220

Val Glu Asn Leu Ile Ile Leu Ala Asn Asn Ser Leu Ser Ser Asn Gly
225 230 235 240

Asn Val Thr Glu Ser Gly Cys Lys Glu Cys Glu Glu Leu Glu Glu Lys
245 250 255

Asn Ile Lys Glu Phe Leu Gln Ser Phe Val His Ile Val Gln Met Phe
260 265 270

Ile Asn Thr Ser Gly Ser Thr Ser Gly Ser Gly Lys Pro Gly Ser Gly
275 280 285

Glu Gly Ser Thr Lys Gly Gln Val Gln Leu Val Glu Ser Gly Gly Gly
290 295 300

Leu Val Gln Pro Gly Gly Ser Leu Arg Leu Ser Cys Ala Ala Ser Gly
305 310 315 320

Phe Thr Phe Ser Ser Tyr Trp Met Tyr Trp Val Arg Gln Thr Pro Gly
325 330 335

Lys Gly Leu Glu Trp Val Ser Thr Ile Asn Arg Asp Gly Ser Ala Thr
340 345 350

Trp Tyr Ala Asp Ser Val Lys Gly Arg Phe Thr Ile Ser Arg Asp Asn
355 360 365

Ala Lys Asn Thr Gly Tyr Leu Gln Met Asn Ser Leu Lys Pro Asp Asp
370 375 380

Thr Ala Val Tyr Tyr Cys Val Ser Asp Pro Asp Asn Tyr Ser Ser Asp
385 390 395 400

Glu Met Val Pro Tyr Trp Gly Gln Gly Thr Gln Val Thr Val Ser Ser
405 410 415

Val Asp Glu His His His His His His His His His His
420 425

<210> SEQ ID NO 26
<211> LENGTH: 366
<212> TYPE: DNA
<213> ORGANISM: artificial
<220> FEATURE:
<223> OTHER INFORMATION: polynucleotide

<400> SEQUENCE: 26
catgtgcagc tggtggagtc tgggggaggc ttggtgcagc ctgggaggtc tctgagactc 60
tcctgtgcag cctctggatt caccttcagt agctactgga tgtactgggt ccgccagact 120
ccagggaagg ggctcgagtg ggtctcaact attaatcgtg atggtagtgc cacatggtat 180
gcagactcag tgaagggccg attcaccatc tccagagaca acgccaagaa cacggggtat 240
ctgcaaatga acagcctgga acctgacgac acggccgtgt attactgtgt gagcgatccg 300
gacaactact ctagcgatga gatggtccct tactggggcc aggggaccca ggtcaccgtc 360
tcctca 366

<210> SEQ ID NO 27
<211> LENGTH: 366
<212> TYPE: DNA
<213> ORGANISM: artificial
<220> FEATURE:
<223> OTHER INFORMATION: polynucleotide

<400> SEQUENCE: 27
caggtgcagc tggtggagtc tgggggaggc ttggtgcagc ctggggggtc tctgagactc 60
tcctgtgcag cctctggatt caccttcagt agctactgga tgtactgggt ccgccagact 120
ccagggaagg ggctcgagtg ggtctcaact attaatcgtg atggtagtgc cacatggtat 180
gcagactcag tgaagggccg attcaccatc tccagagaca acgccaagaa cacggggtat 240
ctgcaaatga acagcctgaa acctgacgac acggccgtgt attactgtgt gagcgatccg 300
gacaactact ctagcgatga gatggtccct tactggggcc aggggaccca ggtcaccgtc 360
tcctca 366

<210> SEQ ID NO 28
<211> LENGTH: 459
<212> TYPE: DNA
<213> ORGANISM: artificial
<220> FEATURE:

<223> OTHER INFORMATION: polynucleotide

<400> SEQUENCE: 28
atgaagtggg taacctttat ttcccttctt tttctcttta gctcggctta ttcccacgtt 60
cagctcgttg aatcaggcgg tgggctcgtg cagcctggaa gatctctccg cttgagctgc 120
gcggcttcag gctttacctt ttccagttat tggatgtatt gggtccggca gacgccagga 180
aaggggcttg aatgggtgtc aacgatcaac cgggacggca gcgcaacctg gtatgccgac 240
tccgttaaag ggaggttcac aataagccga gacaatgcga aaaacacagg atacctgcaa 300
atgaatagct tggagcctga tgatacggct gtatattatt gcgtgtctga tcccgacaac 360
tatagtagtg acgagatggt cccatattgg gggcagggaa cacaagtcac agtctccagc 420
gtcgacgagc atcatcatca tcaccaccac caccaccac 459

<210> SEQ ID NO 29
<211> LENGTH: 459
<212> TYPE: DNA
<213> ORGANISM: artificial
<220> FEATURE:
<223> OTHER INFORMATION: polynucleotide

<400> SEQUENCE: 29
atgaagtggg taacctttat ttcccttctt tttctcttta gctcggctta ttcccaggtg 60
cagctggtgg agtctggggg aggcttggtg cagcctgggg ggtcactgag actctcctgt 120
gcagcctctg gattcacctt cagtagctac tggatgtact gggtccgcca gactccaggg 180
aaggggctcg agtgggtatc aactattaat cgtgatggta gtgccacatg gtatgcagac 240
tcagtgaagg gccgattcac catctccaga gacaacgcca agaacacggg gtatctgcaa 300
atgaacagcc tgaaacctga cgacacggcc gtgtattact gtgtgagcga tccggacaac 360
tactctagcg atgagatggt cccttactgg ggccagggga cccaggtcac cgtctcctca 420
gtcgacgagc atcatcatca tcaccaccac caccaccac 459

<210> SEQ ID NO 30
<211> LENGTH: 900
<212> TYPE: DNA
<213> ORGANISM: artificial
<220> FEATURE:
<223> OTHER INFORMATION: polynucleotide

<400> SEQUENCE: 30
gccgccacca tgaagtgggt aacctttatt tcccttcttt ttctctttag ctcggcttat 60
tcccaggtgc agctggtgga gtctggggga ggcttggtgc agcctggggg ctctctgaga 120
ctctcctgtg cagcctctgg cctcaccttc agtagctata acatgggctg gttccgccag 180
gctccagggc aaggccttga ggctgtagca tctattacct ggagtggtcg ggacacattc 240
tatgcagact ccgtgaaggg ccgattcacc atctccagag acaactccaa gaacactctc 300
tatctgcaaa tgaacagcct gcgcgcggag gacacggccg tttattattg tgctgcaaac 360
ccctggccag tggcggcgcc acgtagtggc acctactggg gccaagggac cctggtcacc 420
gtctcctcat ctggcggcgg cggttctggt ggaggaggta gtgggggggg aggaagcgga 480
gggggtggct cagggcacgt tcagctcgtt gaatcaggcg gtgggctcgt gcagcctgga 540
agatctctcc gcttgagctg cgcggcttca ggctttacct tttccagtta ttggatgtat 600
tgggtccggc agacgccagg aaaggggctt gaatgggtgt caacgatcaa ccgggacggc 660
agcgcaacct ggtatgccga ctccgttaaa gggaggttca caataagccg agacaatgcg 720
aaaaacacag gatacctgca aatgaatagc ttggagcctg atgatacggc tgtatattat 780
tgcgtgtctg atcccgacaa ctatagtagt gacgagatgg tcccatattg ggggcaggga 840
acacaagtca cagtctccag cgtcgacgag catcatcatc atcaccacca ccaccaccac 900

<210> SEQ ID NO 31
<211> LENGTH: 900
<212> TYPE: DNA
<213> ORGANISM: artificial
<220> FEATURE:
<223> OTHER INFORMATION: polynucleotide

<400> SEQUENCE: 31
gccgccacca tgaagtgggt aacctttatt tcccttcttt ttctctttag ctcggcttat 60
tcccaggtgc agctggtgga gtctggggga ggcttggtgc agcctggggg ctctctgaga 120
ctctcctgtg cagcctctgg cctcaccttc agtagctata acatgggctg gttccgccag 180
gctccagggc aaggccttga ggctgtagca tctattacct ggagtggtcg ggacacattc 240
tatgcagact ccgtgaaggg ccgattcacc atctccagag acaactccaa gaacactctc 300
tatctgcaaa tgaacagcct gcgcgcggag gacacggccg tttattattg tgctgcaaac 360
ccctggccag tggcggcgcc acgtagtggc acctactggg gccaagggac cctggtcacc 420
gtctcctcat ctggcggcgg cggttctggt ggaggaggta gtgggggggg aggaagcgga 480
gggggtggct cagggcaggt gcagctggtg gagtctgggg gaggcttggt gcagcctggg 540
gggtcactga gactctcctg tgcagcctct ggattcacct tcagtagcta ctggatgtac 600
tgggtccgcc agactccagg gaaggggctc gagtgggtat caactattaa tcgtgatggt 660
agtgccacat ggtatgcaga ctcagtgaag ggccgattca ccatctccag agacaacgcc 720
aagaacacgg ggtatctgca aatgaacagc ctgaaacctg acgacacggc cgtgtattac 780
tgtgtgagcg atccggacaa ctactctagc gatgagatgg tcccttactg gggccagggg 840
acccaggtca ccgtctcctc agtcgacgag catcatcatc atcaccacca ccaccaccac 900

<210> SEQ ID NO 32
<211> LENGTH: 1296
<212> TYPE: DNA
<213> ORGANISM: artificial
<220> FEATURE:
<223> OTHER INFORMATION: polynucleotide

<400> SEQUENCE: 32
gccgccacca tgaagtgggt aacctttatt tcccttcttt ttctctttag ctcggcttat 60
tcccaggtgc agctggtgga gtctggggga ggcttggtgc agcctggggg ctctctgaga 120
ctctcctgtg cagcctctgg cctcaccttc agtagctata acatgggctg gttccgccag 180
gctccagggc aaggccttga ggctgtagca tctattacct ggagtggtcg ggacacattc 240
tatgcagact ccgtgaaggg ccgattcacc atctccagag acaactccaa gaacactctc 300
tatctgcaaa tgaacagcct gcgcgcggag gacacggccg tttattattg tgctgcaaac 360
ccctggccag tggcggcgcc acgtagtggc acctactggg gccaagggac cctggtcacc 420
gtctcctcat ctggcggcgg cggttctggt ggaggaggta gtgggggggg aggaagcgga 480
gggggtggct cagggaactg ggtgaatgta ataagtgatt tgaaaaaaat tgaagatctt 540
attcaatcta tgcatattga tgctacttta tatacggaaa gtgatgttca ccccagttgc 600
aaagtaacag caatgaagtg ctttctcttg gagttacaag ttatttcact tgagtccgga 660

```
gatgcaagta ttcatgatac agtagaaaat ctgatcatcc tagcaaacaa cagtttgtct    720

tctaatggga atgtaacaga atctggatgc aaagaatgtg aggaactgga ggaaaaaaat    780

attaaagaat tttgcagag ttttgtacat attgtccaaa tgttcatcaa cacttctggc    840

agtaccagcg ggtcagggaa acctggcagt ggggaaggtt ccacaaaagg tcacgttcag    900

ctcgttgaat caggcggtgg gctcgtgcag cctggaagat ctctccgctt gagctgcgcg    960

gcttcaggct ttaccttttc cagttattgg atgtattggg tccggcagac gccaggaaag   1020

gggcttgaat gggtgtcaac gatcaaccgg gacggcagcg caacctggta tgccgactcc   1080

gttaaaggga ggttcacaat aagccgagac aatgcgaaaa acacaggata cctgcaaatg   1140

aatagcttgg agcctgatga tacggctgta tattattgcg tgtctgatcc cgacaactat   1200

agtagtgacg agatggtccc atattggggg cagggaacac aagtcacagt ctccagcgtc   1260

gacgagcatc atcatcatca ccaccaccac caccac                             1296
```

<210> SEQ ID NO 33
<211> LENGTH: 1296
<212> TYPE: DNA
<213> ORGANISM: artificial
<220> FEATURE:
<223> OTHER INFORMATION: polynucleotide

<400> SEQUENCE: 33

```
gccgccacca tgaagtgggt aacctttatt tcccttcttt ttctctttag ctcggcttat     60

tcccaggtgc agctggtgga gtctggggga ggcttggtgc agcctggggg ctctctgaga    120

ctctcctgtg cagcctctgg cctcaccttc agtagctata acatgggctg gttccgccag    180

gctccagggc aaggccttga ggctgtagca tctattacct ggagtggtcg ggacacattc    240

tatgcagact ccgtgaaggg ccgattcacc atctccagag acaactccaa gaacactctc    300

tatctgcaaa tgaacagcct gcgcgcggag gacacggccg tttattattg tgctgcaaac    360

ccctggccag tggcggcgcc acgtagtggc acctactggg gccaagggac cctggtcacc    420

gtctcctcat ctggcggcgg cggttctggt ggaggaggta gtgggggggg aggaagcgga    480

gggggtggct cagggaactg ggtgaatgta ataagtgatt tgaaaaaaat tgaagatctt    540

attcaatcta tgcatattga tgctacttta tatacggaaa gtgatgttca ccccagttgc    600

aaagtaacag caatgaagtg ctttctcttg gagttacaag ttatttcact tgagtccgga    660

gatgcaagta ttcatgatac agtagaaaat ctgatcatcc tagcaaacaa cagtttgtct    720

tctaatggga atgtaacaga atctggatgc aaagaatgtg aggaactgga ggaaaaaaat    780

attaaagaat tttgcagag ttttgtacat attgtccaaa tgttcatcaa cacttctggc    840

agtaccagcg ggtcagggaa acctggcagt ggggaaggtt ccacaaaagg tcaggtgcag    900

ctggtggagt ctgggggagg cttggtgcag cctgggggt cactgagact ctcctgtgca    960

gcctctggat tcaccttcag tagctactgg atgtactggg tccgccagac tccagggaag   1020

gggctcgagt gggtatcaac tattaatcgt gatggtagtg ccacatggta tgcagactca   1080

gtgaagggcc gattcaccat ctccagagac aacgccaaga acacggggta tctgcaaatg   1140

aacagcctga aacctgacga cacggccgtg tattactgtg tgagcgatcc ggacaactac   1200

tctagcgatg agatggtccc ttactggggc caggggaccc aggtcaccgt ctcctcagtc   1260

gacgagcatc atcatcatca ccaccaccac caccac                             1296
```